United States Patent
Campana et al.

(10) Patent No.: US 10,829,737 B2
(45) Date of Patent: *Nov. 10, 2020

(54) CHIMERIC RECEPTOR WITH NKG2D SPECIFICITY FOR USE IN CELL THERAPY AGAINST CANCER AND INFECTIOUS DISEASE

(71) Applicants: ST. JUDE CHILDREN'S RESEARCH HOSPITAL, INC., Memphis, TN (US); NATIONAL UNIVERSITY OF SINGAPORE, Singapore (SG)

(72) Inventors: Dario Campana, Singapore (SG); Yu-Hsiang Chang, Kaohsiung (TW)

(73) Assignees: ST. JUDE CHILDREN'S RESEARCH HOSPITAL, INC., Memphis, TN (US); NATIONAL UNIVERSITY OF SINGAPORE, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/857,268

(22) Filed: Dec. 28, 2017

(65) Prior Publication Data
US 2018/0135015 A1 May 17, 2018

Related U.S. Application Data

(63) Continuation of application No. 15/337,854, filed on Oct. 28, 2016, now Pat. No. 10,538,739, which is a continuation of application No. 14/764,070, filed as application No. PCT/US2014/013292 on Jan. 28, 2014, now Pat. No. 9,511,092.

(60) Provisional application No. 61/757,481, filed on Jan. 28, 2013.

(51) Int. Cl.
| | |
|---|---|
| C12N 5/0783 | (2010.01) |
| A61K 38/00 | (2006.01) |
| C07K 14/725 | (2006.01) |
| C07K 14/705 | (2006.01) |
| A61K 35/17 | (2015.01) |
| C12N 5/00 | (2006.01) |

(52) U.S. Cl.
CPC .......... *C12N 5/0646* (2013.01); *A61K 35/17* (2013.01); *A61K 38/00* (2013.01); *C07K 14/705* (2013.01); *C07K 14/7051* (2013.01); *C07K 14/7056* (2013.01); *C12N 5/0087* (2013.01); *C07K 2319/00* (2013.01); *C07K 2319/70* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,902,733 | A | 5/1999 | Hirt et al. |
| 6,261,839 | B1 | 7/2001 | Multhoff et al. |
| 7,435,596 | B2 | 10/2008 | Campana et al. |
| 7,994,298 | B2 | 8/2011 | Zhang et al. |
| 8,026,097 | B2 | 9/2011 | Campana et al. |
| 8,399,645 | B2 | 3/2013 | Campana et al. |
| 9,511,092 | B2 | 12/2016 | Campana et al. |
| 9,605,049 | B2 | 3/2017 | Campana et al. |
| 9,834,590 | B2 | 12/2017 | Campana et al. |
| 9,856,322 | B2 | 1/2018 | Campana et al. |
| 2003/0157713 | A1 | 8/2003 | Ohno et al. |
| 2005/0113564 | A1 | 5/2005 | Campana et al. |
| 2008/0299137 | A1 | 12/2008 | Svendsen et al. |
| 2009/0202501 | A1 | 8/2009 | Zhang et al. |
| 2016/0000828 | A1 | 1/2016 | Campana |
| 2017/0283482 | A1 | 10/2017 | Campana et al. |

FOREIGN PATENT DOCUMENTS

| | | |
|---|---|---|
| EP | 0952213 A2 | 10/1999 |
| EP | 0830599 B1 | 4/2000 |
| EP | 1231262 A1 | 8/2002 |
| EP | 1306427 A1 | 5/2003 |
| EP | 1053301 B1 | 4/2004 |
| EP | 1233058 B1 | 12/2006 |
| EP | 1820017 AO | 8/2007 |
| EP | 2411507 | 2/2012 |
| EP | 2493485 | 9/2012 |
| EP | 2493486 | 9/2012 |
| EP | 2141997 B1 | 10/2012 |
| EP | 2593542 | 5/2013 |
| EP | 2614151 | 7/2013 |
| EP | 2756521 | 7/2014 |
| EP | 2537416 B1 | 11/2014 |

(Continued)

OTHER PUBLICATIONS

Muller et al, Cancer Immunol Immunother., 2008, vol. 57: pp. 411-423.*
Pende, D. et al., Cancer Res., 2002, vol. 62: pp. 6178-6186.*
Milone, M.C. et al., "Chimeric Receptors Containing CD137 Signal Transduction Domains Mediate Enhanced Survival of T Cells and Increased Antileukemic Efficacy In Vivo" Molecular Therapy, 2009, vol. 17, No. 8, pp. 1453-1464.
Song, D.G. et al., "In vivo persistence, tumor localization and anti-tumor activity of CAR engineered T cells is enhanced by costimulatory signaling through CD137 (4-1BB)" Cancer Res., 2011, vol. 71, No. 13, pp. 4617-4627.

(Continued)

*Primary Examiner* — Michael D Burkhart
(74) *Attorney, Agent, or Firm* — Troutman Pepper Hamilton Sanders LLP

(57) ABSTRACT

The invention provides a chimeric receptor comprising NKG2D, DAP10 and CD3 zeta. Also disclosed is a composition comprising this chimeric receptor and methods for making and using it to enhance the cytotoxicity and antitumor capacity of NK cells. The invention also encompasses methods for use of NKG2D-DAP10-CD3 zeta polypeptides, vectors and cells in methods for treating cancer and other proliferative disorders, as well as infectious diseases.

24 Claims, 7 Drawing Sheets

Figure 2A:
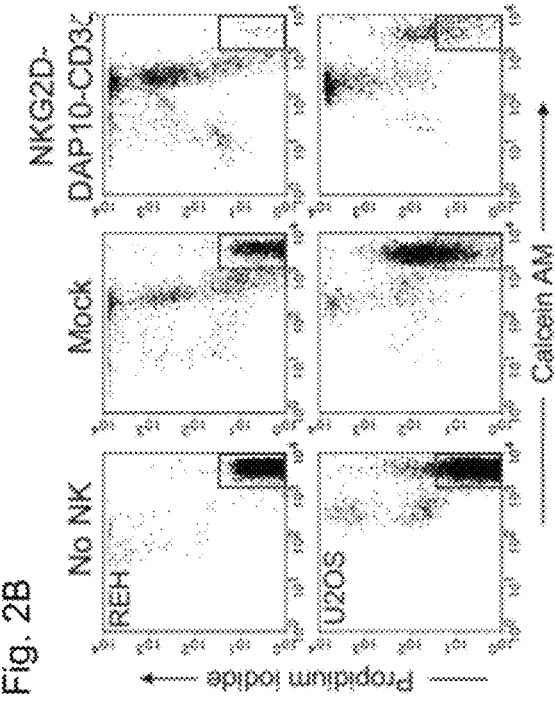
Figure 2B:
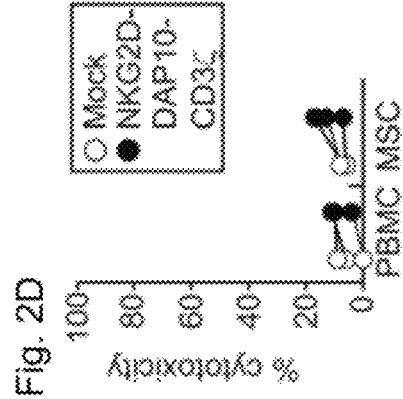

Specification includes a Sequence Listing.

(56) References Cited

FOREIGN PATENT DOCUMENTS

| | | |
|---|---|---|
| EP | 2856876 A1 | 4/2015 |
| EP | 2866834 | 5/2015 |
| EP | 2903637 | 8/2015 |
| EP | 2904106 | 8/2015 |
| EP | 2948544 | 12/2015 |
| EP | 2956175 | 12/2015 |
| EP | 2961831 | 1/2016 |
| EP | 2964753 | 1/2016 |
| EP | 2968601 | 1/2016 |
| EP | 2970426 | 1/2016 |
| EP | 2986636 | 2/2016 |
| EP | 3008173 | 4/2016 |
| EP | 3012268 A1 | 4/2016 |
| EP | 2614077 B1 | 8/2016 |
| EP | 3057986 | 8/2016 |
| EP | 3063175 | 9/2016 |
| EP | 3071221 | 9/2016 |
| EP | 3071222 | 9/2016 |
| EP | 3071223 | 9/2016 |
| EP | 3083671 | 10/2016 |
| EP | 3083691 | 10/2016 |
| EP | 3094653 | 11/2016 |
| EP | 3105318 | 12/2016 |
| EP | 3105335 | 12/2016 |
| EP | 3115373 A1 | 1/2017 |
| EP | 3119425 | 1/2017 |
| EP | 3126380 | 2/2017 |
| EP | 3134432 | 3/2017 |
| EP | 3180359 | 6/2017 |
| EP | 3189132 | 7/2017 |
| WO | 9641163 A1 | 12/1996 |
| WO | 1999006557 A2 | 2/1999 |
| WO | 9938954 A1 | 8/1999 |
| WO | 0129191 A1 | 4/2001 |
| WO | 0138494 A1 | 5/2001 |
| WO | 0210350 A1 | 2/2002 |
| WO | 2003089616 A2 | 10/2003 |
| WO | 2004027036 A2 | 4/2004 |
| WO | 2006036445 A2 | 4/2006 |
| WO | 2006052534 A2 | 5/2006 |
| WO | 2006061626 A2 | 6/2006 |
| WO | 2008121420 A1 | 10/2008 |
| WO | 2009117566 A1 | 9/2009 |
| WO | 2010110734 A1 | 9/2010 |
| WO | 2012136231 | 10/2010 |
| WO | 2011053321 A1 | 5/2011 |
| WO | 2011053322 A1 | 5/2011 |
| WO | 2011150976 A1 | 12/2011 |
| WO | 2012009422 A1 | 1/2012 |
| WO | 2012031744 A1 | 3/2012 |
| WO | 2012071411 A2 | 8/2012 |
| WO | 2013040557 A2 | 3/2013 |
| WO | 2013126720 A2 | 8/2013 |
| WO | 2013126726 A1 | 8/2013 |
| WO | 2014005072 A1 | 1/2014 |
| WO | 2014011993 A2 | 1/2014 |
| WO | 2014055413 A2 | 4/2014 |
| WO | 2014055442 A2 | 4/2014 |
| WO | 2014055668 A1 | 4/2014 |
| WO | 2014099671 A1 | 6/2014 |
| WO | 2014117121 A1 | 7/2014 |
| WO | 2014127261 A1 | 8/2014 |
| WO | 2014134165 A1 | 9/2014 |
| WO | 2014138704 A1 | 9/2014 |
| WO | 2014145252 A2 | 9/2014 |
| WO | 2014164554 A1 | 10/2014 |
| WO | 2014172584 | 10/2014 |
| WO | 2014186469 A2 | 11/2014 |
| WO | 2014201021 A2 | 12/2014 |
| WO | 2015058018 A1 | 4/2015 |
| WO | 2015066551 A1 | 5/2015 |
| WO | 2015075468 A1 | 5/2015 |
| WO | 2015075469 A1 | 5/2015 |
| WO | 2015075470 A1 | 5/2015 |
| WO | 2015092024 A2 | 6/2015 |
| WO | 2015095895 A1 | 6/2015 |
| WO | 2015105522 A1 | 7/2015 |
| WO | 2015120421 A1 | 8/2015 |
| WO | 2015123642 A1 | 8/2015 |
| WO | 2015142314 A1 | 9/2015 |
| WO | 2015142661 A1 | 9/2015 |
| WO | 2015150771 A1 | 10/2015 |
| WO | 2015154012 A1 | 10/2015 |
| WO | 2015164759 A2 | 10/2015 |
| WO | 2016011210 A2 | 1/2016 |
| WO | 2016025880 | 2/2016 |
| WO | 2016030691 A1 | 3/2016 |
| WO | 2016033331 A1 | 3/2016 |
| WO | 2016033690 | 3/2016 |
| WO | 2016040441 A1 | 3/2016 |
| WO | 2016042041 A1 | 3/2016 |
| WO | 2016042461 A1 | 3/2016 |
| WO | 2016061574 A1 | 4/2016 |
| WO | 2016069607 A1 | 5/2016 |
| WO | 2016073602 A2 | 5/2016 |
| WO | 2016073629 A1 | 5/2016 |
| WO | 2016073755 A2 | 5/2016 |
| WO | 2016100985 A2 | 6/2016 |
| WO | 2016109661 A1 | 7/2016 |
| WO | 2016115482 A1 | 7/2016 |
| WO | 2016123122 A1 | 8/2016 |
| WO | 2016123333 A1 | 8/2016 |
| WO | 2016124765 A1 | 8/2016 |
| WO | 2016124930 A1 | 8/2016 |
| WO | 2016126608 A1 | 8/2016 |
| WO | 2016141357 A1 | 9/2016 |
| WO | 2016149254 A1 | 9/2016 |
| WO | 2016151315 A1 | 9/2016 |
| WO | 2016154055 A1 | 9/2016 |
| WO | 2016011210 A2 | 10/2016 |
| WO | 2016172537 A1 | 10/2016 |
| WO | 2016172583 A1 | 10/2016 |
| WO | 2016174405 A1 | 11/2016 |
| WO | 2016174406 A1 | 11/2016 |
| WO | 2016174407 A1 | 11/2016 |
| WO | 2016174461 A1 | 11/2016 |
| WO | 2016174652 A1 | 11/2016 |
| WO | 2016191587 A1 | 12/2016 |
| WO | 2016191755 A1 | 12/2016 |
| WO | 2016196388 A1 | 12/2016 |
| WO | 2016197108 A1 | 12/2016 |
| WO | 2016210293 A1 | 12/2016 |
| WO | 2017004150 A1 | 1/2017 |
| WO | 2017011804 A1 | 1/2017 |
| WO | 2017021701 A1 | 2/2017 |
| WO | 2017023859 A1 | 2/2017 |
| WO | 2017029511 A1 | 2/2017 |
| WO | 2017032777 A1 | 3/2017 |
| WO | 2017034615 A1 | 3/2017 |
| WO | 2017041749 A1 | 3/2017 |
| WO | 2017049166 A1 | 3/2017 |
| WO | 2017058752 A1 | 4/2017 |
| WO | 2017058753 A1 | 4/2017 |
| WO | 2017079705 A1 | 5/2017 |
| WO | 2017127729 A1 | 5/2017 |

OTHER PUBLICATIONS

Song, D.G. et al., "Chimeric NKG2D CAR-Expressing T Cell-Mediated Attack of Human Ovarian Cancer is Enhanced by Histone Deacetylase Inhibition" Human Gene Therapy, 2013, vol. 24, pp. 295-305.

Aguera-Gonzalez et al., "Palmitoylation of MICA, a Ligand for NKG2D, Mediates its Recruitment to Membrane Microdomaines and Promotes its Shedding," Eur. J. Immunol. (2011), vol. 41, pp. 3667-3676.

Barber et al., "Chimeric NKG2D Receptor-Bearing T cells as Imunotherapy for Ovarian Cancer," Cander Res. (2007), vol. 67, No. 10, pp. 5003-5008.

Barber et al., "Immunotherapy with Chimeric NKG2D Receptors Leads to Long-term Tumor-Free Survival and Development of Host

(56) References Cited

OTHER PUBLICATIONS

Antitumor Immunity in Murine Ovarian Cancer," J. Immunol. (2008) vol. 180, pp. 72-78.
Barber et al., "Chimeric NKG2D T Cells Require Both T Cells- and Host-Derived Cytokine Secretion and Perforin Expression to Increase Tumor Antigen Presentation and Systemic Immunity", J Immunol (2009), vol. 183, pp. 2365-2372.
Barber et al, "Chimeric NKG2D Expressing T Cells Eliminate Immunosuppression and Activate Immunity within the Ovarian Tumor Microenvironment", J Immunol (2009), vol. 183, pp. 6939-6947.
Barber et al, "Treatment of Multiple Myetoma with Adoptively Transferred Chimeric NKG2D Receptor-Expressing T Cells", Gene Therapy (2011), vol. 18, pp. 509-516.
Barber et al., "Chimeric NKG2D Receptor-Expressing T Cells as an Immunotherapy for Multiple Myeloma", Exp. Hematol. ( 2008), vol. 36, pp. 1318-1328.
Billadeau D.O. et al., "NKG2D-DAP10 triggers human NK cell-mediated killing via a Syk-independent regulatory pathway", Nature Immunology (2003), vol. 4, No. 6, pp. 557-564.
Chang et al., "A Chimeric Receptor with NKG2D Specificity Enhances Natural Killer Cell Activation and Killing of Tumor Cells", Cancer Res. (2013), vol. 73, No. 6, pp. 1777-1786.
Diefenbach et al., Selective Associations with Signaling Proteins Determine Stimulatory Versus Costimulatory Activity of NKG2D, Nature Immunology (2002), vol. 3, pp. 1142-1149.
Doubrovina et al, Evasion from NK Cell Immunity by MHC Class I Chain-Related Molecules Expressing colon Adenocarcinoma, J Immunol (2003), vol. 171, No. 12, pp. 6891-6999.
Extended European Search Report and Written Opinion dated Jul. 5, 2016, issued by the European Patent Office in European Patent Application No. 14743792.5, 6 pages.
Fujisaki et al., "Expansion of Highly Cytotoxic Human Natural Killer Cells for Cancer Cell Therapy", Cancer Res. (2009), vol. 59, pp. 4010-4017.
Garrity et al., "The Activating NKG2D Receptor Assembles in the Membrane with Two Signaling Dimers Into a Hexameric Structure", Proc. Natl. Acad. Sci. USA (2005), vol. 102, pp. 7641-7646.
Gilfillan S. et al., "NKG2D recruits two distinct adapters to trigger NK cell activation and costimulation", Nature Immunology, (2002), vol. 3, No. 12, pp. 1150-1155.
Hayashi. T. et al., "Identification of the NKG2D Haplotypes Associated with Natural Cytotoxic Activity of Peripheral Blood Lymphocytes and Cancer immuriosurvelliance", Cancer Research (2006), vol. 66, No. 01, pp. 563-570.
Horng et al., "NKG2D Signaling is Coupled to the Interleukin 15 Receptor Signaling Pathway", Nat. Immunol. (2007), vol. 8, pp. 1345-1352.
Imai et al., "Chimeric Receptors with 4-1BB Signaling Capacity Provoke Potent Cytotoxicity Against Acute Lymphoblastic Leukemia", Leukemia (2004), vol. 18, pp. 676-684.
International Preliminary Report on Patentability dated Jul. 28, 2015, issued in corresponding PCT application No. PCT/US2014/013292.
International Search Report dated Apr. 28, 2014, issued in corresponding PCT application No. PCT/US2014/013292.
Kohn et al., "CARs on Track in the Clinic, Molecular Therapy", The Journal of the American Society of Gene Therapy ( 2011), vol. 19, pp. 432-438.
Lehner et al., "Redirecting T Cells to Ewing's Sarcoma Family of Tumors by a Chimeric NKG2D Receptor Expressed by Lentiviral Transduction or mRNA Transfection", PLoS One (2012), vol. 7:e31210.
Martinez et al., Cutting Edge: NKG2D-Dependent Cytotoxicity is Controlled by Ligand Distribution in the Target Cell Membrane, J Immunol (2011), vol. 186, pp. 5538-5542.
Miller et al., "Successful Adoptive Transfer and In Vivo Expansion of Human Haploidentical NK Cells in Patients with Cancer", Blood (2005), vol. 105, pp. 3051-3057.

Nu et al., 1999, An Activating Immunoreceptor Complex Formed by NKG2D and DAP10, Science 285:730-732.
Park et al., Complex Regulation of Human NKG2D-DAP10 Cell Surface Expression: Opposing Roles of the γc Cytokines and TGF-Beta1, Blood (2011), vol. 118, pp. 3019-3027.
Roszak, A. et al., "Prevalence of the NKG2D Thr72Ala Polymorphism in Patients with Cervical Carcinoma", Genetic Testing and Molecular Biomarkers (2012), vol. 16, No. 08, pp. 841-845.
Rubnitz et al., "NKAML: A Pilot Study to Determine the Safety and Feasibility of Haploidentical Natural Killer Cell Transplantation in Childhood Acute Myeloid Leukemia", J Clin Oncol. (2010), vol. 28, pp. 955-959.
Salih et al., "Cutting Edge: Down-Regulation of MICA on Human Tumors by Proteolytic Shedding", J. Immunol. (2002), vol. 169, pp. 4098-4102.
Search Report and Written Opinion dated Apr. 27, 2016 and May 11, 2016, issued from the Intellectual Property Office of Singapore in Singapore Patent Application No. 11201505858V; 8 pages.
Sentman, et al, "NKG2D CARs as Cell Therapy for Cancer", The Cancer Journal (2014), vol. 20, No. 2, pp. 156-159.
Shimasaki et al., "A Clinically Adaptable Method to Enhance the Cytotoxicity of Natural Killer Cells Against B-cell Malignancies", Cytotherapy (2012), vol. 14, pp. 830-840.
Spear et al., "Chimeric Antigen Receptor T Cells Shape Myeloid Cell Function within the Tumor Microenvironment Through IFN-γ and GM-CSF", J Immunol (2012), vol. 188, pp. 6389-6398.
Spear et al., "NKG2D CAR T-Cell Therapy Inhibits the Growth of NKG2D Ligand Heterogeneous Tumors", Immunology and Cell Biology (2013), vol. 91, pp. 435-440.
Spear et al., "Collaboration of Chimeric Antigen Receptor (CAR)-expressing T Cells for Optimal Elimination of Established Ovarian Tumors", OncoImmunology (2013), vol. 2, No. 4, pp. e23564-1-e23564-12.
Upshaw et al., "NKG2D-Mediated Signaling Requires a DAP10-Bound Grb2-Vav1 Intermediate and Phosphatidylinositol-3-kinase in Human Natural Killer Cells", Nat. Immunol. (2006), vol. 7, pp. 524-532.
Wu et al., An Activating Immunoreceptor Complex Formed by NKG2D and DAP10, Science (1999), vol. 285, pp. 730-732.
Written Opinion dated Apr. 8, 2014, Issued in PCT/US20141013292 11 pages.
Zhang et al, "Generation of Antitumor Responses by Genetic Modification of Primary Human T Cells with a Chimeric NKG2D Receptor", Cancer Res (2006), vol. 66, No. 11, pp. 5927-5933.
Zhang et al, "Mouse Tumor Vasculature Expresses NKG2D Ligands and Can Be Targeted by Chimeric NKG2D-Modified T Cells", J Immunol (2013), vol. 190, pp. 2455-2463.
Zhang et al., "Chimeric NK-Receptor-Bearing T Cells Mediate Antitumor Immunotherapy", Blood (2005), vol. 106, No. 5, pp. 1544-1551.
Zhang et al., "Chimeric NKG2D-Modified T Cells Inhibit Systemic T-Cell Lymphoma Growth in a Manner Involving Multiple Cytokines and Cytotoxic Pathways", Cancer Res (2007), vol. 67, pp. 11029-11036.
Antony, G.K. et al., "Interleukin 2 in Cancer Therapy", Current Medicinal Chemistry (2010), vol. 17, pp. 3297-3302.
Baek, H. et al., "Ex Vivo Expansion of Natural Killer Cells Using Cryopreserved Irradiated Feeder Cells", Anticancer Research (2013), vol. 33, pp. 2011-2019.
Berger, C. et al., "Saftey and immunologic effects of IL-15 administration in nonhuman primates", Blood (2009), vol. 114, No. 12, pp. 2417-2426.
Boyman, O. et al., "The role of interleukin-2 during homeostasis and activation of the immune system", Nature Reviews; (2012), vol. 12, pp. 180-190.
Budagian, V. et al., "IL-15/IL-15 receptor biology: A guided tour through an expanding universe", Cytokine & Growth Factor Reviews (2006), vol. 17, pp. 259-280.
Burkett, P. et al., "Coordinate Expression and Trans Presentation of Interleukin (IL)-15R alpha and IL-15 Supports Natural Killer Cell and Memory CD8+ T Cell Homeostasis", The Journal of Experimental Medicine (2004), vol. 200, No. 7, pp. 825-834.

(56) References Cited

OTHER PUBLICATIONS

Carlsten, M. et al., "Genetic manipulation of NK cells for cancer immunotherapy: techniques and clinical implications", Frontiers in Immunology (2015), vol. 6, article 266, 9 pages.

Carson, W. E. et al., "A Potential Role for Interleukin-15 in the Regulation of Human Natural Killer Cell Survival", Journal of Clinical Investigation (1997), vol. 99, No. 5, pp. 937-943.

Chang, Y. et al., "A Chimeric Receptor with NKG2D Specificity Enhances Natural Killer Cell Activation and Killing of Tumor Cells", Cancer Research (2013), vol. 73, No. 6, pp. 1777-1786.

Chao, D. T. et al., "BCL-2 Family: Regulators of Cell Death", Annu. Rev. Immunol. (1998), vol. 16, pp. 395-419.

Chertova, E. et al., "Characterization and Favorable in Vivo Properties of Heterodimeric Soluble IL-15:IL-15R Alpha Cytokine Compared to IL-15 Monomer", The Journal of Biological Chemistry (2013), vol. 288, No. 25, pp. 18093-18103.

Cho, D. et al., "Expansion and Activation of Natural Killer Cells for Cancer Immunotherapy", Korean J. Lab Med; 2009), vol. 29, pp. 89-96.

Cooley, S. et al., "Donor selection for natural killer cell receptor genes leads to superior survival after unrelated transplantation for acute myelogenous leukemia", Blood (2010), vol. 116, No. 14, pp. 2411-2419.

Cooper, M. A. et al., "In vivo evidence for a dependence on interleukin 15 for survival of natural killer cells", Blood (2002), vol. 100, No. 10, pp. 3633-3638.

Curti, A. et al., "Successful transfer of alloreactive haploidentical KIR ligand-mismatched natural killer cells after infusion in elderly high risk acute myeloid leukemia patients", Blood (2011), vol. 118, No. 12, pp. 3273-3279.

Delahaye, N. F. et al., "Alternatively spliced NKp30 isoforms affect the prognosis of gastrointestinal stromal tumors", Nature Medicine (2011), vol. 17, No. 6, pp. 700-708.

Dubois, S. et al., "IL-15R alpha Recycles and Presents IL-15 in trans to Neighboring Cells", Immunity (2002), vol. 17, pp. 537-547.

Dubois, S. et al., "Preassociation of IL-15 with IL-15R alpha-IgG1-Fc Enhances Its Activity on Proliferation of NK and CD8-F/CD44high T Cells and Its Antitumor Action", The Journal of Immunology (2008), vol. 180, pp. 2099-2106.

Fehniger, T. A. et al., "Interleukin 15: biology and relevance to human disease", Blood (2001), vol. 97, No. 1, pp. 14-32.

Fernandez-Messina, L. et al., "Human NKG2D-ligands: cell biology strategies to ensure immune recognition", Frontiers in Immunology (2012), vol. 3, article 299, 9 pages.

Ferlazzo, G. et al., "Distinct roles of IL-12 and IL-15 in human natural killer cell activation by dendritic cells from secondary lymphoid organs", PNAS (2004), vol. 101, No. 47, pp. 16606-16611.

Ferris, R. L. et al., "Tumor Antigen-Targeted, Monoclonal Antibody-Based Immunotherapy: Clinical Response, Cellular Immunity and Immunoescape", Journal of Clinical Oncology (2010), vol. 28, No. 28, pp. 4390-4399.

International Search Report and Written Opinion Issued in International Application No. PCT/SG2015/050111, dated Aug. 17, 2015, 12 pages.

Kabalak, G. et al., "Association of an NKG2D gene variant with systemic lupus erythematosus in two populations", Human Immunology (2010), vol. 71, pp. 74-78.

Parkhurst, M. R. et al., "Adoptive Transfer of Autologous Natural Killer Cells Leads to High Levels of Circulating Natural Killer Cells but Does Not Mediate Tumor Regression", Clinical Cancer Research (2011), vol. 17, No. 19, pp. 6287-6297.

Qian, Li et al., "Construction of a plasmid for co-expression of mouse membrane-bound form of IL-15 and RAE-1(e) and its biological activity", Plasmid (2011), vol. 65, pp. 239-245.

Rosenstein, M. et al., "Extravasation of Intravascular Fluid Mediated by the Systemic Administration of Recombinant Interleukin 2", The Journal of Immunology (1986), vol. 137, No. 5, pp. 1735-1742.

Rowley, J. et al., "Expression of IL-15RA or an IL-15/1L-15RA fusion on CD8+ T cells modifies adoptively transferred T-cell function in cis", Eur. J. Immunol. (2009), vol. 39, pp. 491-506.

Rubnitz, J. E. et al., "NKAML: A Pilot Study to Determine the Safety and Feasibility of Haploidentical Natural Killer Cell Transplantation in Childhood Acute Myeloid Leukemia", Journal of Clinical Oncology (2010), vol. 28, No. 6, pp. 955-959.

Ruggeri, L. et al., "Effectiveness of Donor Natural Killer Cell Alloreactivity in Mismatched Hematopoietic Transplants", Science (2002), vol. 295, pp. 2097-2100.

Scott, A. M. et al., "Antibody therapy of cancer", Nature Reviews (2012), vol. 12, pp. 278-287.

Sentman, C. L. et al., "NK Cell Receptors as Tools in Cancer Immunotherapy", Advances in Cancer Research (2006), pp. 249-292.

Sentman, C. L., et al., "NKG2D CARs as Cell Therapy for Cancer", The Cancer Journal (2014), vol. 20, No. 2, pp. 156-159.

Sheard, M. A. et al., "Membrane-bound TRAIL Supplements Natural Killer Cell Cytotoxicity Against Neuroblastoma Cells", J. Immunother. (2013), vol. 36, No. 5, pp. 319-329.

Shimasaki, N. et al., "A clinically adaptable method to enhance the cytotoxicity of natural killer cells against B-cell malignancies", Cytotherapy (2012), vol. 14, pp. 830-840.

Shum, B. P. et al., "Conservation and Variation in Human and Common Chimpanzee CD94 and NKG2 Genes", The Journal of Immunology (2002), vol. 168, pp. 240-252.

Sneller, M. C. et al., "IL-15 administered by continuous infusion to rhesus macaques induces massive expansion of CD8+ T effector memory population in peripheral blood", Blood (2011), vol. 118, No. 26, pp. 6845-6848.

Somanchi, S. S. et al., "Expansion, Purification, and Functional Assessment of Human Peripheral Blood NK Cells", Journal of Visualized Experiments (2011), vol. 48, 5 pages.

Tagaya, Y. et al., "IL-15: A Pleiotropic Cytokine with Diverse Receptor/Signaling Pathways Whose Expression is Controlled at Multiple Levels", Immunity (1996), vol. 4, pp. 329-336.

Tsukamoto, K. et al., "Juxtacrine function of interleukin-15/interleukin-15 receptor system in tumour derived human B-cell lines", Clinical and Experimental Immunology (2006), vol. 146, pp. 559-566.

Vivier, E. et al., "Innate or Adaptive Immunity? The Example of Natural Killer Cells", Science (2011), vol. 331, pp. 44-49.

Vujanovic, L. et al, Virally infected and matured human dendritic cells activate natural killer cells via cooperative activity of plasma membrane-bound TNF and IL-15, Blood (2010), vol. 116, No. 4, pp. 575-583.

Waldmann, T. A. et al., "Saftey (toxicity), pharmacokinetics, immunogenicity, and impact on elements of the normal immune system of recombinant human IL-15 in rhesus macaques", Blood (2011), vol. 117, No. 18, pp. 4787-4795.

Watzl, C. et al., "Signal Transduction During Activation and Inhibition of Natural Killer Cells", Curr. Protoc. Immunol.; (2010), 19 pages. doi:10.1002/0471142735.im1109bs90.

Wittnebel, S. et al., "Membrane-Bound Interleukin (IL)-15 on Renal Tumor Cells Rescues Natural Killer Cells from IL-2 Starvation-Induced Apoptosis", Cancer Research (2007), vol. 67, No. 12, pp. 5594-5599.

Zanoni, I. et al., "IL-15 cis Presentation is Required for Optimal NK Cell Activation in Lipopolysaccharide-Mediated Inflammatory Conditions", Cell Reports (2013), vol. 3, pp. 1235-1249.

Zhang, J. et al., "Characterization of interleukin-15 gene-modified human natural killer cells: implications for adoptive cellular immunotherapy", Haematologica (2004), vol. 89, No. 3, pp. 338-347.

Giuliani, M. et al., "Generation of a Novel Regulatory NK Cell Subset from Peripheral Blood CD34+ Progenitors Promoted by Membrane-Bound IL-15", PLOS One (2008), vol. 3, Issue 5, p. e2241.

Hsu, C. et al., "Cytokine-independent growth and clonal expansion of a primary human CD8+ T-cell clone following retroviral transduction with the IL-15 gene", Blood (2007), vol. 109, No. 12, pp. 5168-5177.

(56) References Cited

OTHER PUBLICATIONS

Hsu, K. C. et al., "Improved outcome in HLA-identical sibling hematopoietic stem-cell transplantation for acute myelogenous leukemia predicted by KIR and HLA genotypes", Blood (2005), vol. 105, No. 12, pp. 4878-4884.
Imai, C. et al., "Genetic modification of primary natural killer cells overcomes inhibitory signals and induces specific killing of leukemic cells", Blood (2005), vol. 106, No. 1, pp. 376-383.
Imamura, M. et al., "Autonomous growth and increased cytotoxicity of natural killer cells expressing membrane-bound interleukin-15", Blood (2014), vol. 124, No. 7, pp. 1081-1088.
Ishii, H. et al., "Monocytes enhance cell proliferation and LMP1 expression of nasal natural killer/T-cell lymphoma cells by cell contact-dependent interaction through membrane-bound IL-15", Int. J. of Cancer (2012), vol. 130, pp. 48-58.
Jiang, W., et al., "hIL-15 gene-modified human natural killer cells (NKL-IL15) augments the anti-human hepatocellular carcinoma effect in vivo", Immunobiology (2014), vol. 219, pp. 547-553.
Kitaya, K. et al., "IL-15 Expression at Human Endometrium and Decidua", Biology of Reproduction (2000), vol. 63, pp. 683-687.
Kitaya, K. et al., "Regulatory Role of Membrane-Bound Form Interleukin-15 on Human Uterine Microvascular Endothelial Cells in Circulating CD16(-) Natural Killer Cell Extravasation into Human Endometrium", Biology of Reproduction (2013), vol. 89(3):70, pp. 1-7.
Kobayashi, H. et al., "Role of trans-cellular IL-15 presentation in the activation of NK cell-mediated killing, which leads to enhanced tumor immunosurveillance", Blood (2005), vol. 105, No. 2, pp. 721-727.
Koka, R. et al., "Cutting Edge: Murine Dendritic Cells Require IL-15Ralpha to prime NK Cells", The Journal of Immunology (2004), vol. 173, pp. 3594-3598.
Kurokawa, M. et al., "Caspases and Kinases in a Death Grip", Cell (2009), vol. 138, pp. 838-854.
Lapteva, N. et al., "Large-scale ex vivo expansion and characterization of natural killer cells for clinical applications", Cytotherapy (2012), vol. 14, pp. 1131-1143.
Leung, W. et al., "Determinants of Antileukemia Effects of Allogeneic NK Cells1", The Journal of Immunology (2004), vol. 172, pp. 644-650.
Liao, W. et al., "Interleukin-2 at the Crossroads of Effector Responses, Tolerance, and Immunotherapy", Immunity (2013) vol. 38, pp. 13-25.
Lugli, E. et al., "Transient and presistent effects of IL-15 on lymphocyte homeostasis in nonhuman primates", Blood (2010) vol. 116, No. 17, pp. 3238-3248.
Miller, J. S., et al., "Therapeutic applications: natural killer cells in the clinic", Hematology (2013), pp. 247-253.
Miller, J. S. et al., "Successful adoptive transfer and in vivo expansion of human haploidentical NK cells in patients with cancer", Blood (2005), vol. 105, No. 8, pp. 3051-3057.
Mishra, A. et al., "Aberrant Overexpression of IL-15 Initiates Large Granular Lymphocyte Leukemia through Chromosomal Instability and DNA Hypermethylation", Cancer Cell (2012), vol. 22, pp. 645-655.
Morandi, B. et al., "NK cells provide helper signal for CD8+ T cells by inducing the expression of membrane-bound IL-15 on DCs", Int. Immunology (2009), vol. 21, No. 5, pp. 599-606.
Mortier, E. et al., "IL-15Ralpha chaperones IL-15 to stable dendritic cell membrane complexes that activate NK cells via trans presentation", JEM (2008), pp. 1213-1225.
Musso, T. et al., "Human Monocytes Constitutively Express Membrane-Bound, Biologically Active, and Interferon-sigma-Upregulated Interleukin-15", Blood (1999), vol. 93, vol. 10, pp. 3531-3539.
Negrini, S. et al., "Membrane-bound IL-15 stimulation on peripheral blood natural kiler progenitors leads to the generation of an adherent subset co-expressing dendritic cells and natural kiler functional markers", Haematologica (2011), vol. 96(5), pp. 762-766.

Olsen, S. et al., "Crystal Structure of the Inteleukin-15-Interleukin-15 Receptor alpha complex", The Journal of Biological Chemistry (2007), vol. 282, No. 51, pp. 37191-37204.
Fujisaki, H. et al., "Expansion of Highly Cytotoxic Human Natural Killer Cells for Cancer Cell Therapy", Cancer Research (2009), vol. 69, No. 9, pp. 4010-4017.
Fujisaki, H. et al., "Replicative potential of human natural killer cells", British Journal of Haematology (2009), vol. 145, pp. 606-613.
Giebel, S. et al., "Survival advantage with KIR ligand incompatibility in hematopoietic stem cell transplantation from unrelated donors", Blood (2003), vol. 102, No. 3, pp. 814-819.
Communication Pursuant to Article 94(3) EPC issued in European Patent Application No. 14743792.5, dated Jun. 9, 2017, 4 pages.
Hara, Ryujiro et al., "NKG2D gene polymorphisms are associate with disease control of chronic myeloid leudemia by dasatinib", Int. J. Hematol (2017), 9 pages.
GenBank Accession No. NM_007360.3, "Homo sapiens killer cell lectin like receptor K1 (KLRK1), mRNA", Sequence ID 315221123, Jan. 12, 2013.
Singapore Second Written Opinion dated Jun. 22, 2017, Issued in Singapore Patent Application No. 11201505858V, 5 pages.
Ho, E.L. et al., "Murine Nkg2d and Cd94 are Clustered within the Natural Killer Complex and are Expressed Independently in Natural Killer Cells" Proceedings of the National Academy of Sciences (1998) vol. 95, No. 11, pp. 6320-6325.
Sattler, S. et al., "Evolution of the C-Type Lectin-Like Receptor Genes of the DECTIN-1 Cluster in the NK Gene Complex" The Scientific World Journal (2012) vol. 2012, 11 pages total.
Tassev, DV et al., "Retargeting NK9s Cells Using an HLA-A2-Restricted, EBNA3C-Specific Chimeric Antigen Receptor" Cancer Gene Therapy (2011) vol. 19, pp. 84-100.
Yim, D. et al., "Molecular Cloning and Characterization of Pig Immunoreceptor DAP10 and NKG2D" Immunogenetics (2001) vol. 53, pp. 243-249.
International Preliminary Report on Patentability for PCT/US2014/013292, cited in European Patent Application 14743792.5, dated Aug. 11, 2015, 12 pages total.
European filed Amendment for European Patent Application No. 14743792.5, dated Mar. 16, 2016, 5 pages total.
European Phase Request in European Patent Application No. 14743792.5, dated Aug. 27, 2015, 10 pages total.
European Response to Search Opinion/Written Opinion/IPER in European Patent Application No. 14743792.5, dated Jan. 26, 2017, 9 pages total.
GenBank Accession No. AF072844.1, "Homo sapiens membrane protein DAP10 (DAP10) mRNA, complete cds", Aug. 4, 1999, 2 pages total.
Lanier, L.L., "DAP10- and DAP12-Associated Receptors in Innate Immunity" Immunological Reviews (2009) vol. 227, pp. 150-160.
Licursi, M. et al., "In Vitro and In Vivo Comparison of Viral and Cellular Internal Ribosome Entry Sites for Bicistronic Vector Expression" Gene Therapy (2011) vol. 18, pp. 631-636.
NCBI Reference Sequence NM_007360.2, "Homo sapiens killer cell lectin-like receptor subfamily K, member 1 (KLRK1), mRNA", Dec. 5, 2010, 10 pages total.
NCBI Reference Sequence NM_198053, "Homo sapiens CD247 molecule (CD247), transcript variant 1, mRNA", Jan. 20, 2008, 11 pages total.
Rabinovich, P.M. et al., "Synthetic Messenger RNA as a Tool for Gene Therapy" Human Gene Therapy (2006) vol. 17, pages 1027-1035.
Request for Ex Parte Reexamination of U.S. Pat. No. 9,511,092 which has been assigned U.S. Appl. No. 90/014,175, filed Aug. 1, 2018, 49 pages total.
Office Action issued by the United State Patent and Trademark Office in U.S. Appl. No. 90/014,175 (Ex Parte Reexamination of U.S. Pat. No. 9,511,092), dated Jan. 29, 2019, 17 pages total.
Cooley, S. et al., "Adoptive Therapy with T Cells/NK Cells" Biology of Blood and Marrow Transplantation (2007) vol. 13, pp. 33-42.

(56) References Cited

OTHER PUBLICATIONS

European Communication (Communication Pursuant to Article 94(3) EPC) issued by the European Patent Office in European Patent Application No. 14743792.5, dated Nov. 20, 2018, 4 pages total.
Singapore Examination Report dated Dec. 10, 2018, issued in Singapore Patent Application No. 11201505858V, 7 pages total.
Boissel L. et al., "Transfection with mRNA for CD19 Specific Chimeric Antigen Receptor Restores NK Cell Mediated Killing of CLL Cells" Leuk Res. (2009) vol. 33, No. 9, pp. 1255-1259.
Kruschinski A. et al., "Engineering Antigen-Specific Primary Human NK Cells Against HER-2 Positive Carcinomas" Proc Natl Acad Sci USA (2008) vol. 105, No. 45, pp. 17481-17486.
Mistry, A.R. et al., "Regulation of Ligands for the Activating Receptor NKG2D" Immunology (2007) vol. 121, pp. 439-447.
Nkarta Therapeutics, "Press Release: NKARTA Therapeutics Announces Exclusive License to Natural Killer Cell Technology from National University of Singapore and St. Jude Children's Research Hospital" (2018) (available at https://www.nkartatx.com/news/061118/), 2 pages total.
Communication (Final Office Action) issued by the United State Patent and Trademark Office in U.S. Appl. No. 90/014,175, dated Jun. 5, 2019, 20 pages total.

\* cited by examiner

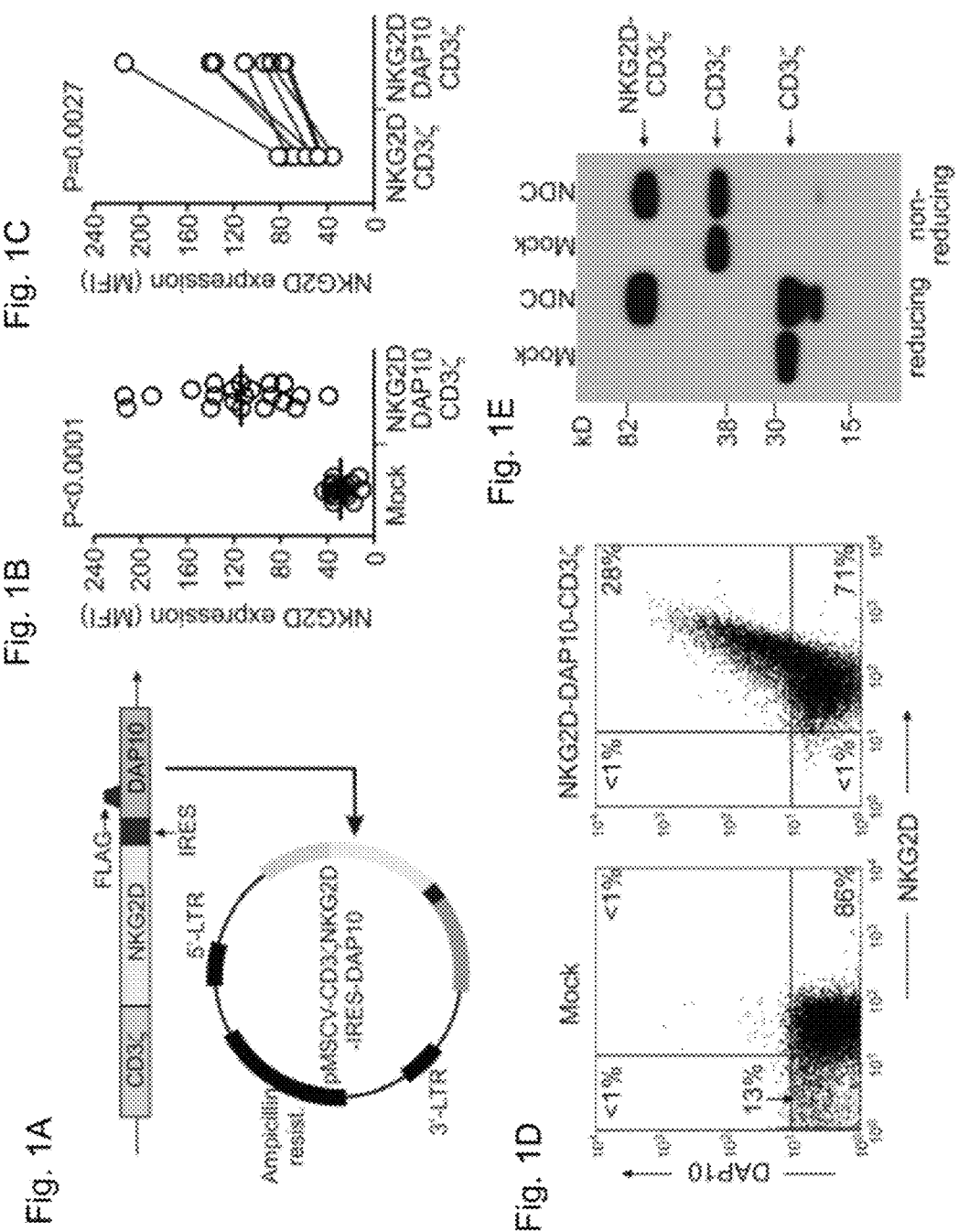

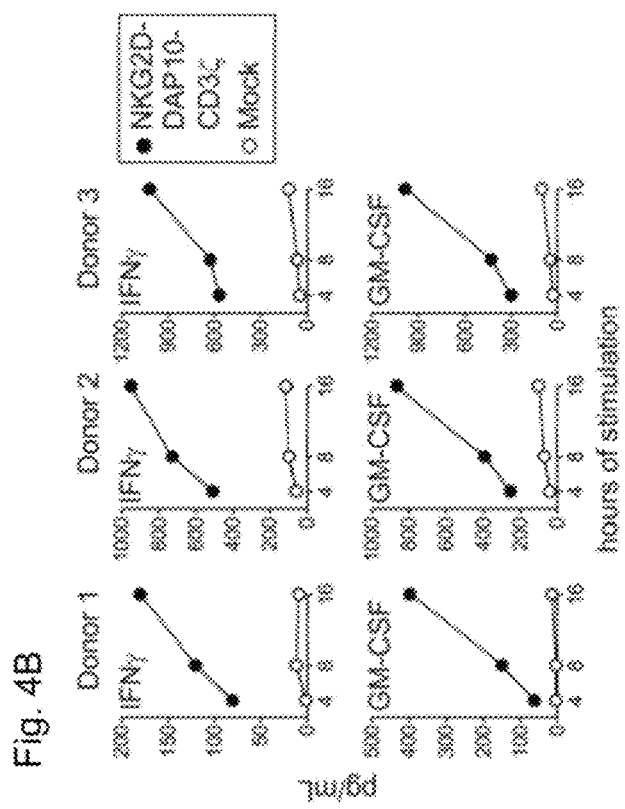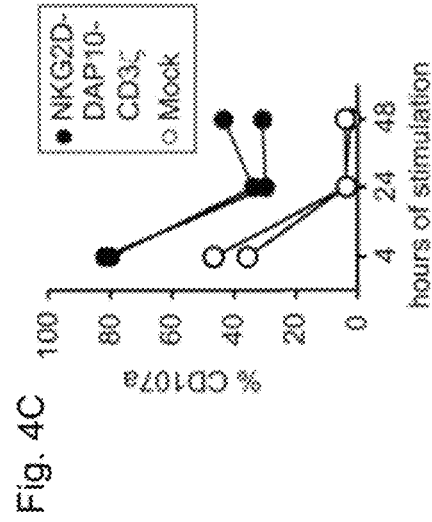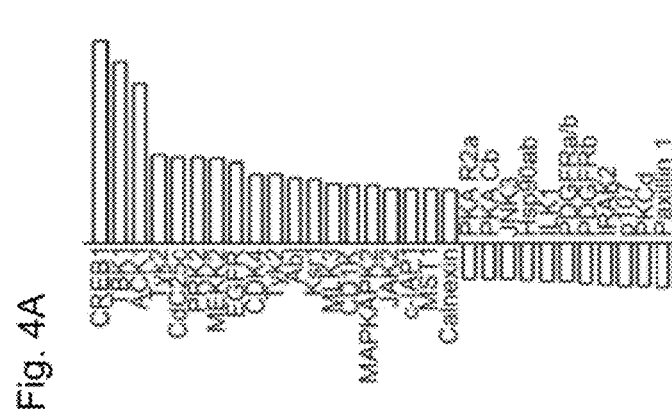

SEQUENCE LISTING

```
<160> NUMBER OF SEQ ID NOS: 26

<210> SEQ ID NO 1
<211> LENGTH: 41
<212> TYPE: DNA
<213> ORGANISM: Artificial Sequence
<220> FEATURE:
<223> OTHER INFORMATION: forward primer for the cloning of
      the cytoplasmic domain of human CD3 zeta

<400> SEQUENCE: 1
atatatgaat cgccgccac catgagagtg aagttcagca g                    41

<210> SEQ ID NO 2
<211> LENGTH: 40
<212> TYPE: DNA
<213> ORGANISM: Artificial Sequence
<220> FEATURE:
<223> OTHER INFORMATION: reverse primer for the cloning of
      the cytoplasmic domain of human CD3 zeta

<400> SEQUENCE: 2
ccgaccacga atccacccgc gagggggcag ggcctgcatg                      40

<210> SEQ ID NO 3
<211> LENGTH: 40
<212> TYPE: DNA
<213> ORGANISM: Artificial Sequence
<220> FEATURE:
<223> OTHER INFORMATION: forward primer for the cloning of
      human NKG2D

<400> SEQUENCE: 3
catgcaggcc ctgcccctc gcgggtggat tcgtggtcgg                       40

<210> SEQ ID NO 4
<211> LENGTH: 32
<212> TYPE: DNA
<213> ORGANISM: Artificial Sequence
<220> FEATURE:
<223> OTHER INFORMATION: reverse primer for the cloning of
      human NKG2D

<400> SEQUENCE: 4
```

-continued

```
tatatagaat tcttacacag tcctttgcat gc                                  32
```

<210> SEQ ID NO 5
<211> LENGTH: 110
<212> TYPE: DNA
<213> ORGANISM: Artificial Sequence
<220> FEATURE:
<223> OTHER INFORMATION: forward primer for the cloning of
      human DAP10 and the FLAG-tag

<400> SEQUENCE: 5

```
atatatccat ggatgatcca tctgggtcac atcctcttcc tgcttttgct cccagtggct    60
gcagctgact acaaagacga tgacgacaag cagacgactc aggagagag               110
```

<210> SEQ ID NO 6
<211> LENGTH: 33
<212> TYPE: DNA
<213> ORGANISM: Artificial Sequence
<220> FEATURE:
<223> OTHER INFORMATION: reverse primer for the cloning of
      human DAP10 and the FLAG-tag

<400> SEQUENCE: 6

```
tatatagcgg ccgctcagcc cctgcctggc atg                                 33
```

<210> SEQ ID NO 7

<400> SEQUENCE: 7

000

<210> SEQ ID NO 8

<400> SEQUENCE: 8

000

<210> SEQ ID NO 9
<211> LENGTH: 342
<212> TYPE: DNA
<213> ORGANISM: Artificial Sequence
<220> FEATURE:
<223> OTHER INFORMATION: cDNA encoding the cytoplasmic domain of human
      CD3 zeta of the chimeric receptor

<400> SEQUENCE: 9

```
atgagagtga agttcagcag gagcgcagac gcccccgcgt accagcaggg ccagaaccag    60
ctctataacg agctcaatct aggacgaaga gaggagtacg atgttttgga caagagacgt   120
ggccgggacc ctgagatggg gggaaagccg cagagaagga agaaccctca ggaaggcctg   180
tacaatgaac tgcagaaaga taagatggcg gaggcctaca gtgagattgg gatgaaaggc   240
gagcgccgga ggggcaaggg gcacgatggc ctttaccagg gtctcagtac agccaccaag   300
gacacctacg acgcccttca catgcaggcc ctgccccctc gc                      342
```

<210> SEQ ID NO 10
<211> LENGTH: 114
<212> TYPE: PRT
<213> ORGANISM: Artificial Sequence
<220> FEATURE:
<223> OTHER INFORMATION: amino acid sequence of the cytoplasmic domain
      of human CD3 zeta of the chimeric receptor

<400> SEQUENCE: 10

Met Arg Val Lys Phe Ser Arg Ser Ala Asp Ala Pro Ala Tyr Gln Gln

```
                1               5                  10                  15
            Gly Gln Asn Gln Leu Tyr Asn Glu Leu Asn Leu Gly Arg Arg Glu Glu
                               20                  25                  30
            Tyr Asp Val Leu Asp Lys Arg Arg Gly Arg Asp Pro Glu Met Gly Gly
                               35                  40                  45
            Lys Pro Gln Arg Arg Lys Asn Pro Gln Glu Gly Leu Tyr Asn Glu Leu
                50                  55                  60
            Gln Lys Asp Lys Met Ala Glu Ala Tyr Ser Glu Ile Gly Met Lys Gly
            65                  70                  75                  80
            Glu Arg Arg Arg Gly Lys Gly His Asp Gly Leu Tyr Gln Gly Leu Ser
                               85                  90                  95
            Thr Ala Thr Lys Asp Thr Tyr Asp Ala Leu His Met Gln Ala Leu Pro
                               100                 105                 110
            Pro Arg

<210> SEQ ID NO 11
<211> LENGTH: 648
<212> TYPE: DNA
<213> ORGANISM: Artificial Sequence
<220> FEATURE:
<223> OTHER INFORMATION: cDNA encoding human NKG2D of the chimeric
      receptor

<400> SEQUENCE: 11
gggtggattc gtggtcggag gtctcgacac agctgggaga tgagtgaatt tcataattat      60
aacttggatc tgaagaagag tgattttttca cacgatggc aaaagcaaag atgtccagta     120
gtcaaaagca aatgtagaga aaatgcatct ccattttttt tctgctgctt catcgctgta     180
gccatgggaa tccgtttcat tattatggta acaatatgga gtgctgtatt cctaaactca     240
ttattcaacc aagaagttca aattcccttg accgaaagtt actgtggccc atgtcctaaa     300
aactggatat gttacaaaaa taactgctac caatttttg atgagagtaa aaactggtat      360
gagagccagg cttcttgtat gtctcaaaat gccagccttc tgaaagtata cagcaaagag     420
gaccaggatt tacttaaact ggtgaagtca tcattgga tgggactagt acacattcca       480
acaaatggat cttggcagtg ggaagatggc tccattctct cacccaacct actaacaata    540
attgaaatgc agaagggaga ctgtgcactc tatgcctcga gctttaaagg ctatatagaa    600
aactgttcaa ctccaaatac gtacatctgc atgcaaagga ctgtgtaa                 648

<210> SEQ ID NO 12
<211> LENGTH: 215
<212> TYPE: PRT
<213> ORGANISM: Artificial Sequence
<220> FEATURE:
<223> OTHER INFORMATION: amino acid sequence of human NKG2D of the
      chiremic receptor

<400> SEQUENCE: 12

Gly Trp Ile Arg Gly Arg Ser Arg His Ser Trp Glu Met Ser Glu
            1               5                   10                  15

Phe His Asn Tyr Asn Leu Asp Leu Lys Lys Ser Asp Phe Ser Thr Arg
                               20                  25                  30

Trp Gln Lys Gln Arg Cys Pro Val Lys Ser Lys Cys Arg Glu Asn
                               35                  40                  45

Ala Ser Pro Phe Phe Phe Cys Cys Phe Ile Ala Val Ala Met Gly Ile
                50                  55                  60

Arg Phe Ile Ile Met Val Thr Ile Trp Ser Ala Val Phe Leu Asn Ser
```

```
                65                  70                  75                  80
Leu Phe Asn Gln Glu Val Gln Ile Pro Leu Thr Glu Ser Tyr Cys Gly
                    85                  90                  95

Pro Cys Pro Lys Asn Trp Ile Cys Tyr Lys Asn Asn Cys Tyr Gln Phe
                100                 105                 110

Phe Asp Glu Ser Lys Asn Trp Tyr Glu Ser Gln Ala Ser Cys Met Ser
            115                 120                 125

Gln Asn Ala Ser Leu Leu Lys Val Tyr Ser Lys Glu Asp Gln Asp Leu
        130                 135                 140

Leu Lys Leu Val Lys Ser Tyr His Trp Met Gly Leu Val His Ile Pro
145                 150                 155                 160

Thr Asn Gly Ser Trp Gln Trp Glu Asp Gly Ser Ile Leu Ser Pro Asn
                165                 170                 175

Leu Leu Thr Ile Ile Glu Met Gln Lys Gly Asp Cys Ala Leu Tyr Ala
            180                 185                 190

Ser Ser Phe Lys Gly Tyr Ile Glu Asn Cys Ser Thr Pro Asn Thr Tyr
        195                 200                 205

Ile Cys Met Gln Arg Thr Val
    210                 215

<210> SEQ ID NO 13
<211> LENGTH: 279
<212> TYPE: DNA
<213> ORGANISM: Artificial Sequence
<220> FEATURE:
<223> OTHER INFORMATION: human DAP10 cDNA

<400> SEQUENCE: 13
atgatccatc tgggtcacat cctcttcctg cttttgctcc cagtggctgc agctcagacg      60
actccaggag agagatcatc actccctgcc ttttaccctg gcacttcagg ctcttgttcc     120
ggatgtgggt ccctctctct gccgctcctg gcaggcctcg tggctgctga tgcggtggca     180
tcgctgctca tcgtgggggc ggtgttcctg tgcgcacgcc acgccgcag ccccgcccaa     240 gatggcaaag tctacatcaa catgccaggc aggggctga                            279

<210> SEQ ID NO 14
<211> LENGTH: 92
<212> TYPE: PRT
<213> ORGANISM: Artificial Sequence
<220> FEATURE:
<223> OTHER INFORMATION: amino acid sequence of human DAP10

<400> SEQUENCE: 14

Met Ile His Leu Gly His Ile Leu Phe Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80

Asp Gly Lys Val Tyr Ile Asn Met Pro Gly Arg Gly
                85                  90

<210> SEQ ID NO 15
```

```
<211> LENGTH: 24
<212> TYPE: DNA
<213> ORGANISM: Artificial Sequence
<220> FEATURE:
<223> OTHER INFORMATION: FLAG-tag

<400> SEQUENCE: 15
gactacaaag acgatgacga caag                                           24

<210> SEQ ID NO 16
<211> LENGTH: 8
<212> TYPE: PRT
<213> ORGANISM: Artificial Sequence
<220> FEATURE:
<223> OTHER INFORMATION: amino acid sequence of FLAG-tag

<400> SEQUENCE: 16

Asp Tyr Lys Asp Asp Asp Asp Lys
1               5

<210> SEQ ID NO 17
<211> LENGTH: 303
<212> TYPE: DNA
<213> ORGANISM: Artificial Sequence
<220> FEATURE:
<223> OTHER INFORMATION: DAP10-FLAG-tag

<400> SEQUENCE: 17
atgatccatc tgggtcacat cctcttcctg cttttgctcc cagtggctgc agctgactac    60
aaagacgatg acgacaagca gacgactcca ggagagagat catcactccc tgccttttac   120
cctggcactt caggctcttg ttccggatgt gggtccctct ctctgccgct cctggcaggc   180
ctcgtggctg ctgatgcggt ggcatcgctg ctcatcgtgg gggcggtgtt cctgtgcgca   240
cgcccacgcc gcagccccgc ccaagatggc aaagtctaca tcaacatgcc aggcaggggc   300
tga                                                                 303

<210> SEQ ID NO 18
<211> LENGTH: 100
<212> TYPE: PRT
<213> ORGANISM: Artificial Sequence
<220> FEATURE:
<223> OTHER INFORMATION: amino acid sequence of DAP10-FLAG-tag

<400> SEQUENCE: 18

Met Ile His Leu Gly His Ile Leu Phe Leu Leu Leu Pro Val Ala
1               5                   10                  15

Ala Ala Asp Tyr Lys Asp Asp Asp Lys Gln Thr Thr Pro Gly Glu
                20                  25                  30

Arg Ser Ser Leu Pro Ala Phe Tyr Pro Gly Thr Ser Gly Ser Cys Ser
            35                  40                  45

Gly Cys Gly Ser Leu Ser Leu Pro Leu Leu Ala Gly Leu Val Ala Ala
        50                  55                  60

Asp Ala Val Ala Ser Leu Leu Ile Val Gly Ala Val Phe Leu Cys Ala
65                  70                  75                  80

Arg Pro Arg Arg Ser Pro Ala Gln Asp Gly Lys Val Tyr Ile Asn Met
                85                  90                  95

Pro Gly Arg Gly
            100

<210> SEQ ID NO 19
<211> LENGTH: 1891
```

```
<212> TYPE: DNA
<213> ORGANISM: Artificial Sequence
<220> FEATURE:
<223> OTHER INFORMATION: CD3zeta-NKG2D-IRES-DAP10-FLAG-tag

<400> SEQUENCE: 19
atgagagtga agttcagcag gagcgcagac gcccccgcgt accagcaggg ccagaaccag      60
ctctataacg agctcaatct aggacgaaga gaggagtacg atgttttgga caagagacgt     120
ggccgggacc ctgagatggg gggaaagccg cagagaagga agaaccctca ggaaggcctg     180
tacaatgaac tgcagaaaga taagatggcg gaggcctaca gtgagattgg gatgaaaggc     240
gagcgccgga ggggcaaggg gcacgatggc ctttaccagg gtctcagtac agccaccaag     300
gacacctacg acgcccttca catgcaggcc ctgcccctc gcgggtggat cgtggtcgg      360 aggtctcgac acagctggga gatgagtgaa tttcataatt ataacttgga tctgaagaag     420
agtgattttt caacacgatg gcaaaagcaa agatgtccag tagtcaaaag caaatgtaga     480
gaaaatgcat ctccattttt tttctgctgc ttcatcgctg tagccatggg aatccgtttc     540
attattatgg taacaatatg gagtgctgta ttcctaaact cattattcaa ccaagaagtt     600
caaattccct tgaccgaaag ttactgtggc ccatgtccta aaaactggat atgttacaaa     660 ataactgct accaattttt tgatgagagt aaaaactggt atgagagcca ggcttcttgt     720
atgtctcaaa atgccagcct tctgaaagta tacagcaaag aggaccagga tttacttaaa     780
ctggtgaagt catatcattg gatgggacta gtacacattc aacaaatgg atcttggcag     840 tgggaagatg gctccattct ctcacccaac ctactaacaa taattgaaat gcagaaggga     900
gactgtgcac tctatgcctc gagctttaaa ggctatatag aaaactgttc aactccaaat     960
acgtacatct gcatgcaaag gactgtgtaa gaattcgtta acctcgagcg ggatcaattc    1020
cgcccccccc ctaacgttac tggccgaagc cgcttggaat aaggccggtg tgcgtttgtc    1080
tatatgttat tttccaccat attgccgtct tttggcaatg tgagggcccg gaaacctggc    1140
cctgtcttct tgacgagcat tcctaggggt ctttcccctc tcgccaaagg aatgcaaggt    1200
ctgttgaatg tcgtgaagga agcagttcct ctggaagctt cttgaagaca acaacgtct    1260 gtagcgaccc tttgcaggca gcggaacccc ccacctggcg acaggtgcct ctgcggccaa    1320
aagccacgtg tataagatac acctgcaaag gcggcacaac cccagtgcca cgttgtgagt    1380
tggatagttg tggaaagagt caaatggctc tcctcaagcg tattcaacaa ggggctgaag    1440
gatgcccaga aggtaccca ttgtatggga tctgatctgg ggcctcggtg cacatgcttt    1500
acatgtgttt agtcgaggtt aaaaaaacgt ctaggccccc cgaaccacgg ggacgtggtt    1560
ttcctttgaa aaacacgata taccatgat gatccatctg ggtcacatcc tcttcctgct    1620
tttgctccca gtggctgcag ctgactacaa agacgatgac gacaagcaga cgactccagg    1680
agagagatca tcactccctg cctttttaccc tggcacttca ggctcttgtt ccggatgtgg    1740
gtccctctct ctgccgctcc tggcaggcct cgtggctgct gatgcggtgg catcgctgct    1800
catcgtgggg gcggtgttcc tgtgcgcacg cccacgccgc agccccgccc aagatggcaa    1860
agtctacatc aacatgccag gcaggggctg a                                   1891

<210> SEQ ID NO 20
<211> LENGTH: 1867
<212> TYPE: DNA
<213> ORGANISM: Artificial Sequence
<220> FEATURE:
<223> OTHER INFORMATION: CD3zeta-NKG2D-IRES-DAP10
```

<400> SEQUENCE: 20

```
atgagagtga agttcagcag gagcgcagac gcccccgcgt accagcaggg ccagaaccag    60
ctctataacg agctcaatct aggacgaaga gaggagtacg atgttttgga caagagacgt   120
ggccgggacc ctgagatggg gggaaagccg cagagaagga agaaccctca ggaaggcctg   180
tacaatgaac tgcagaaaga taagatggcg gaggcctaca gtgagattgg gatgaaaggc   240
gagcgccgga ggggcaaggg gcacgatggc ctttaccagg gtctcagtac agccaccaag   300
gacacctacg acgcccttca catgcaggcc ctgcccctc gcgggtggat cgtggtcgg    360
aggtctcgac acagctggga gatgagtgaa tttcataatt ataacttgga tctgaagaag   420
agtgattttt caacacgatg gcaaaagcaa agatgtccag tagtcaaaag caaatgtaga   480
gaaaatgcat ctccattttt tttctgctgc ttcatcgctg tagccatggg aatccgtttc   540
attattatgg taacaatatg gagtgctgta ttcctaaact cattattcaa ccaagaagtt   600
caaattccct tgaccgaaag ttactgtggc ccatgtccta aaaactggat atgttacaaa   660
ataactgct accaattttt tgatgagagt aaaaactggt atgagagcca ggcttcttgt   720
atgtctcaaa atgccagcct tctgaaagta tacagcaaag aggaccagga tttacttaaa   780
ctggtgaagt catatcattg atgggacta gtacacattc aacaaatgg atcttggcag    840
tgggaagatg gctccattct ctcacccaac ctactaacaa taattgaaat gcagaaggga   900
gactgtgcac tctatgcctc gagctttaaa ggctatatag aaaactgttc aactccaaat   960
acgtacatct gcatgcaaag gactgtgtaa gaattcgtta acctcgagcg ggatcaattc  1020
cgcccccccc ctaacgttac tggccgaagc cgcttggaat aaggccggtg tgcgtttgtc  1080
tatatgttat tttccaccat attgccgtct tttggcaatg tgagggcccg gaaacctggc  1140
cctgtcttct tgacgagcat tcctaggggt ctttccctc tcgccaaagg aatgcaaggt   1200
ctgttgaatg tcgtgaagga agcagttcct ctggaagctt cttgaagaca acaacgtct   1260
gtagcgaccc tttgcaggca gcggaacccc ccacctggcg acaggtgcct ctgcggccaa  1320
aagccacgtg tataagatac acctgcaaag gcggcacaac cccagtgcca cgttgtgagt  1380
tggatagttg tggaaagagt caaatggctc tcctcaagcg tattcaacaa ggggctgaag  1440
gatgcccaga aggtaccccca ttgtatggga tctgatctgg ggcctcggtg cacatgcttt  1500
acatgtgttt agtcgaggtt aaaaaaacgt ctaggccccc cgaaccacgg ggacgtggtt  1560
ttccttgaa aaacacgata ataccatgat gatccatctg ggtcacatcc tcttcctgct   1620
tttgctccca gtggctgcag ctcagacgac tccaggagag agatcatcac tccctgcctt  1680
ttaccctggc acttcaggct cttgttccgg atgtgggtcc ctctctctgc cgctcctggc  1740
aggcctcgtg gctgctgatg cggtggcatc gctgctcatc gtggggcgg tgttcctgtg   1800
cgcacgccca cgccgcagcc ccgcccaaga tggcaaagtc tacatcaaca tgccaggcag  1860
gggctga                                                            1867
```

<210> SEQ ID NO 21
<211> LENGTH: 651
<212> TYPE: DNA
<213> ORGANISM: Artificial Sequence
<220> FEATURE:
<223> OTHER INFORMATION: human NKG2D cDNA

<400> SEQUENCE: 21

```
atggggtgga ttcgtggtcg gaggtctcga cacagctggg agatgagtga atttcataat    60
tataacttgg atctgaagaa gagtgatttt tcaacacgat ggcaaaagca aagatgtcca   120
```

-continued

```
gtagtcaaaa gcaaatgtag agaaaatgca tctccatttt ttttctgctg cttcatcgct      180
gtagccatgg gaatccgttt cattattatg gtaacaatat ggagtgctgt attcctaaac      240
tcattattca accaagaagt tcaaattccc ttgaccgaaa gttactgtgg cccatgtcct      300
aaaaactgga tatgttacaa aaataactgc taccaatttt ttgatgagag taaaaactgg      360
tatgagagcc aggcttcttg tatgtctcaa aatgccagcc ttctgaaagt atacagcaaa      420
gaggaccagg atttacttaa actggtgaag tcatatcatt ggatgggact agtacacatt      480
ccaacaaatg gatcttggca gtgggaagat ggctccattc tctcacccaa cctactaaca      540
ataattgaaa tgcagaaggg agactgtgca ctctatgcct cgagctttaa aggctatata      600
gaaaactgtt caactccaaa tacgtacatc tgcatgcaaa ggactgtgta a              651
```

<210> SEQ ID NO 22
<211> LENGTH: 216
<212> TYPE: PRT
<213> ORGANISM: Artificial Sequence
<220> FEATURE:
<223> OTHER INFORMATION: amino acid sequence of human NKG2D

<400> SEQUENCE: 22

```
Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Thr Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215
```

<210> SEQ ID NO 23
<211> LENGTH: 5448
<212> TYPE: DNA
<213> ORGANISM: Artificial Sequence
<220> FEATURE:
<223> OTHER INFORMATION: pCMV6-XL5-CD3zeta-NKG2D
<220> FEATURE:

```
<221> NAME/KEY: CDS
<222> LOCATION: (994)...(1983)

<400> SEQUENCE: 23
aacaaaatat taacgcttac aatttccatt cgccattcag gctgcgcaac tgttgggaag      60
ggcgatcggt gcgggcctct tcgctattac gccagctggc gaaaggggga tgtgctgcaa     120
ggcgattaag ttgggtaacg ccagggtttt cccagtcacg acgttgtaaa acgacggcca     180
gtgccaagct gatctataca ttgaatcaat attggcaatt agccatatta gtcattggtt     240
atatagcata aatcaatatt ggctattggc cattgcatac gttgtatcta tatcataata     300
tgtacattta tattggctca tgtccaatat gaccgccatg ttgacattga ttattgacta     360
gttattaata gtaatcaatt acggggtcat tagttcatag cccatatatg gagttccgcg     420
ttacataact tacggtaaat ggcccgcctg gctgaccgcc caacgacccc cgcccattga     480
cgtcaataat gacgtatgtt cccatagtaa cgccaatagg gactttccat tgacgtcaat     540
gggtggagta tttacggtaa actgcccact tggcagtaca tcaagtgtat catatgccaa     600
gtccgccccc tattgacgtc aatgacggta aatggcccgc ctggcattat gcccagtaca     660
tgaccttacg ggactttcct acttggcagt acatctacgt attagtcatc gctattacca     720
tggtgatgcg gttttggcag tacaccaatg ggcgtggata gcggtttgac tcacggggat     780
ttccaagtct ccaccccatt gacgtcaatg ggagtttgtt ttggcaccaa aatcaacggg     840
actttccaaa atgtcgtaat aaccccgccc cgttgacgca aatgggcggt aggcgtgtac     900
ggtgggaggt ctatataagc agagctcgtt tagtgaaccg tcagaatttt gtaatacgac     960
tcactatagg gcggccgcga attcgccgcc acc atg aga gtg aag ttc agc agg    1014
                                    Met Arg Val Lys Phe Ser Arg
                                     1               5 agc gca gac gcc ccc gcg tac cag cag ggc cag aac cag ctc tat aac   1062
Ser Ala Asp Ala Pro Ala Tyr Gln Gln Gly Gln Asn Gln Leu Tyr Asn
             10                  15                  20 gag ctc aat cta gga cga aga gag gag tac gat gtt ttg gac aag aga   1110
Glu Leu Asn Leu Gly Arg Arg Glu Glu Tyr Asp Val Leu Asp Lys Arg
 25                  30                  35 cgt ggc cgg gac cct gag atg ggg gga aag ccg cag aga agg aag aac   1158
Arg Gly Arg Asp Pro Glu Met Gly Gly Lys Pro Gln Arg Arg Lys Asn
 40                  45                  50                  55 cct cag gaa ggc ctg tac aat gaa ctg cag aaa gat aag atg gcg gag   1206
Pro Gln Glu Gly Leu Tyr Asn Glu Leu Gln Lys Asp Lys Met Ala Glu
                 60                  65                  70 gcc tac agt gag att ggg atg aaa ggc gag cgc cgg agg ggc aag ggg   1254
Ala Tyr Ser Glu Ile Gly Met Lys Gly Glu Arg Arg Arg Gly Lys Gly
             75                  80                  85 cac gat ggc ctt tac cag ggt ctc agt aca gcc acc aag gac acc tac   1302
His Asp Gly Leu Tyr Gln Gly Leu Ser Thr Ala Thr Lys Asp Thr Tyr
         90                  95                 100 gac gcc ctt cac atg cag gcc ctg ccc cct cgc ggg tgg att cgt ggt   1350
Asp Ala Leu His Met Gln Ala Leu Pro Pro Arg Gly Trp Ile Arg Gly
    105                 110                 115 cgg agg tct cga cac agc tgg gag atg agt gaa ttt cat aat tat aac   1398
Arg Arg Ser Arg His Ser Trp Glu Met Ser Glu Phe His Asn Tyr Asn
120                 125                 130                 135 ttg gat ctg aag aag agt gat ttt tca aca cga tgg caa aag caa aga   1446
Leu Asp Leu Lys Lys Ser Asp Phe Ser Thr Arg Trp Gln Lys Gln Arg
                140                 145                 150 tgt cca gta gtc aaa agc aaa tgt aga gaa aat gca tct cca ttt ttt   1494
Cys Pro Val Val Lys Ser Lys Cys Arg Glu Asn Ala Ser Pro Phe Phe
```

```
                155                 160                 165
ttc tgc tgc ttc atc gct gta gcc atg gga atc cgt ttc att att atg    1542
Phe Cys Cys Phe Ile Ala Val Ala Met Gly Ile Arg Phe Ile Ile Met
            170                 175                 180 gta aca ata tgg agt gct gta ttc cta aac tca tta ttc aac caa gaa    1590
Val Thr Ile Trp Ser Ala Val Phe Leu Asn Ser Leu Phe Asn Gln Glu
185                 190                 195 gtt caa att ccc ttg acc gaa agt tac tgt ggc cca tgt cct aaa aac    1638
Val Gln Ile Pro Leu Thr Glu Ser Tyr Cys Gly Pro Cys Pro Lys Asn
200                 205                 210                 215 tgg ata tgt tac aaa aat aac tgc tac caa ttt ttt gat gag agt aaa    1686
Trp Ile Cys Tyr Lys Asn Asn Cys Tyr Gln Phe Phe Asp Glu Ser Lys
                220                 225                 230 aac tgg tat gag agc cag gct tct tgt atg tct caa aat gcc agc ctt    1734
Asn Trp Tyr Glu Ser Gln Ala Ser Cys Met Ser Gln Asn Ala Ser Leu
            235                 240                 245 ctg aaa gta tac agc aaa gag gac cag gat tta ctt aaa ctg gtg aag    1782
Leu Lys Val Tyr Ser Lys Glu Asp Gln Asp Leu Leu Lys Leu Val Lys
        250                 255                 260 tca tat cat tgg atg gga cta gta cac att cca aca aat gga tct tgg    1830
Ser Tyr His Trp Met Gly Leu Val His Ile Pro Thr Asn Gly Ser Trp
265                 270                 275 cag tgg gaa gat ggc tcc att ctc tca ccc aac cta cta aca ata att    1878
Gln Trp Glu Asp Gly Ser Ile Leu Ser Pro Asn Leu Leu Thr Ile Ile
280                 285                 290                 295 gaa atg cag aag gga gac tgt gca ctc tat gcc tcg agc ttt aaa ggc    1926
Glu Met Gln Lys Gly Asp Cys Ala Leu Tyr Ala Ser Ser Phe Lys Gly
                300                 305                 310 tat ata gaa aac tgt tca act cca aat acg tac atc tgc atg caa agg    1974
Tyr Ile Glu Asn Cys Ser Thr Pro Asn Thr Tyr Ile Cys Met Gln Arg
            315                 320                 325 act gtg taa tctagattgc ggccgcggtc atagctgttt cctgaacaga           2023
Thr Val * tcccgggtgg catccctgtg acccctcccc agtgcctctc ctggccctgg aagttgccac  2083
tccagtgccc accagccttg tcctaataaa attaagttgc atcattttgt ctgactaggt  2143
gtccttctat aatattatgg ggtggagggg ggtggtatgg agcaagggc  aagttgggaa  2203 gacaacctgt agggcctgcg gggtctattg ggaaccaagc tggagtgcag tggcacaatc  2263
ttggctcact gcaatctccg cctcctgggt tcaagcgatt ctcctgcctc agcctcccga  2323
gttgttggga ttccaggcat gcatgaccag gctcagctaa ttttgttttt tttggtagag  2383
acggggtttc accatattgg ccaggctggt ctccaactcc taatctcagg tgatctaccc  2443
accttggcct cccaaattgc tgggattaca ggcgtgaacc actgctccct tcctgtcct   2503 tctgatttta aaataactat accagcagga ggacgtccag acacagcata ggctacctgg  2563
ccatgcccaa ccggtgggac atttgagttg cttgcttggc actgtcctct catgcgttgg  2623
gtccactcag tagatgcctg ttgaattggg tacgcggcca gcttggctgt ggaatgtgtg  2683
tcagttaggg tgtggaaagt ccccaggctc cccagcaggc agaagtatgc aaagcatgca  2743
tctcaattag tcagcaacca ggtgtggaaa gtccccaggc tccccagcag gcagaagtat  2803
gcaaagcatg catctcaatt agtcagcaac catagtcccg cccctaactc cgcccatccc  2863
gcccctaact ccgcccagtt ccgcccattc tccgcccat ggctgactaa ttttttttat   2923
ttatgcagag gccgaggccg cctcggcctc tgagctattc cagaagtagt gaggaggctt  2983
ttttggaggc ctaggctttt gcaaaaagct cctcgactgc attaatgaat cggccaacgc  3043
```

```
gcggggagag gcggtttgcg tattgggcgc tcttccgctt cctcgctcac tgactcgctg   3103
cgctcggtcg ttcggctgcg gcgagcggta tcagctcact caaaggcggt aatacggtta   3163
tccacagaat cagggggataa cgcaggaaag aacatgtgag caaaaggcca gcaaaaggcc   3223
aggaaccgta aaaaggccgc gttgctggcg ttttttccata ggctccgccc ccctgacgag   3283
catcacaaaa atcgacgctc aagtcagagg tggcgaaacc cgacaggact ataaagatac   3343
caggcgtttc ccctggaag ctccctcgtg cgctctcctg ttccgaccct gccgcttacc   3403
ggatacctgt ccgcctttct cccttcggga agcgtggcgc tttctcatag ctcacgctgt   3463
aggtatctca gttcggtgta ggtcgttcgc tccaagctgg gctgtgtgca cgaaccccc   3523 gttcagcccg accgctgcgc cttatccggt aactatcgtc ttgagtccaa cccggtaaga   3583
cacgacttat cgccactggc agcagccact ggtaacagga ttagcagagc gaggtatgta   3643
ggcggtgcta cagagttctt gaagtggtgg cctaactacg gctacactag aagaacagta   3703
tttggtatct gcgctctgct gaagccagtt accttcggaa aaagagttgg tagctcttga   3763
tccggcaaac aaaccaccgc tggtagcggt ggtttttttg tttgcaagca gcagattacg   3823
cgcagaaaaa aaggatctca agaagatcct ttgatctttt ctacggggtc tgacgctcag   3883
tggaacgaaa actcacgtta agggattttg gtcatgagat tatcaaaaag gatcttcacc   3943
tagatccttt taaattaaaa atgaagtttt aaatcaatct aaagtatata tgagtaaact   4003
tggtctgaca gttaccaatg cttaatcagt gaggcaccta tctcagcgat ctgtctattt   4063
cgttcatcca tagttgcctg actccccgtc gtgtagataa ctacgatacg ggagggctta   4123
ccatctggcc ccagtgctgc aatgataccg cgagacccac gctcaccggc tccagattta   4183
tcagcaataa accagccagc cggaagggcc gagcgcagaa gtggtcctgc aactttatcc   4243
gcctccatcc agtctattaa ttgttgccgg gaagctagag taagtagttc gccagttaat   4303
agtttgcgca acgttgttgc cattgctaca ggcatcgtgg tgtcacgctc gtcgtttggt   4363
atggcttcat tcagctccgg ttcccaacga tcaaggcgag ttacatgatc ccccatgttg   4423
tgcaaaaaag cggttagctc cttcggtcct ccgatcgttg tcagaagtaa gttggccgca   4483
gtgttatcac tcatggttat ggcagcactg cataattctc ttactgtcat gccatccgta   4543
agatgctttt ctgtgactgg tgagtactca accaagtcat tctgagaata gtgtatgcgg   4603
cgaccgagtt gctcttgccc ggcgtcaata cgggataata ccgcgccaca tagcagaact   4663
ttaaaagtgc tcatcattgg aaaacgttct cggggcgaaa actctcaag gatcttaccg   4723 ctgttgagat ccagttcgat gtaacccact cgtgcaccca actgatcttc agcatctttt   4783
actttcacca gcgtttctgg gtgagcaaaa acaggaaggc aaaatgccgc aaaaaaggga   4843
ataagggcga cacggaaatg ttgaatactc atactcttcc tttttcaata ttattgaagc   4903
atttatcagg gttattgtct catgagcgga tacatatttg aatgtattta gaaaaataaa   4963 caaataggg ttccgcgcac atttccccga aaagtgccac ctgacgcgcc ctgtagcggc   5023
gcattaagcg cggcgggtgt ggtggttacg cgcagcgtga ccgctacact tgccagcgcc   5083
ctagcgcccg ctcctttcgc tttcttccct tcctttctcg ccacgttcgc cggctttccc   5143
cgtcaagctc taaatcgggg gctcccttta gggttccgat ttagtgcttt acggcacctc   5203
gaccccaaaa aacttgatta gggtgatggt tcacgtagtg gccatcgcc ctgatagacg   5263 gttttttcgcc ctttgacgtt ggagtccacg ttctttaata gtggactctt gttccaaact   5323
ggaacaacac tcaaccctat ctcggtctat tcttttgatt tataagggat tttgccgatt   5383
tcggcctatt ggttaaaaaa tgagctgatt taacaaaaat ttaacgcgaa ttttaacaaa   5443
```

```
atatt                                                                  5448

<210> SEQ ID NO 24
<211> LENGTH: 4745
<212> TYPE: DNA
<213> ORGANISM: Artificial Sequence
<220> FEATURE:
<223> OTHER INFORMATION: pCMV6-XL5-DAP10
<220> FEATURE:
<221> NAME/KEY: CDS
<222> LOCATION: (994)...(1272)

<400> SEQUENCE: 24
aacaaaatat taacgcttac aatttccatt cgccattcag gctgcgcaac tgttgggaag     60
ggcgatcggt gcgggcctct tcgctattac gccagctggc gaaaggggga gtgctgcaa    120 ggcgattaag ttgggtaacg ccagggtttt cccagtcacg acgttgtaaa acgacggcca    180
gtgccaagct gatctataca ttgaatcaat attggcaatt agccatatta gtcattggtt    240
atatagcata aatcaatatt ggctattggc cattgcatac gttgtatcta tcataata     300 tgtacattta tattggctca gtccaatat gaccgccatg ttgacattga ttattgacta    360
gttattaata gtaatcaatt acggggtcat tagttcatag cccatatatg gagttccgcg    420
ttacataact tacggtaaat ggcccgcctg gctgaccgcc caacgacccc cgcccattga    480
cgtcaataat gacgtatgtt cccatagtaa cgccaatagg gactttccat tgacgtcaat    540
gggtggagta tttacggtaa actgcccact tggcagtaca tcaagtgtat catatgccaa    600
gtccgccccc tattgacgtc aatgacggta aatggcccgc ctggcattat gcccagtaca    660
tgaccttacg gactttcct acttggcagt acatctacgt attagtcatc gctattacca    720
tggtgatgcg gttttggcag tacaccaatg ggcgtggata gcggtttgac tcacggggat    780
ttccaagtct ccaccccatt gacgtcaatg ggagtttgtt ttggcaccaa atcaacggg    840 actttccaaa atgtcgtaat aaccccgccc gttgacgca aatgggcggt aggcgtgtac    900
ggtgggaggt ctatataagc agagctcgtt tagtgaaccg tcagaatttt gtaatacgac    960
tcactatagg gcggccgcga attcgccgcc acc atg atc cat ctg ggt cac atc   1014
                                     Met Ile His Leu Gly His Ile
                                      1               5 ctc ttc ctg ctt ttg ctc cca gtg gct gca gct cag acg act cca gga   1062
Leu Phe Leu Leu Leu Leu Pro Val Ala Ala Ala Gln Thr Thr Pro Gly
       10                  15                  20 gag aga tca tca ctc cct gcc ttt tac cct ggc act tca ggc tct tgt   1110
Glu Arg Ser Ser Leu Pro Ala Phe Tyr Pro Gly Thr Ser Gly Ser Cys
 25                  30                  35 tcc gga tgt ggg tcc ctc tct ctg ccg ctc ctg gca ggc ctc gtg gct   1158
Ser Gly Cys Gly Ser Leu Ser Leu Pro Leu Leu Ala Gly Leu Val Ala
 40                  45                  50                  55 gct gat gcg gtg gca tcg ctg ctc atc gtg ggg gcg gtg ttc ctg tgc   1206
Ala Asp Ala Val Ala Ser Leu Leu Ile Val Gly Ala Val Phe Leu Cys
                 60                  65                  70 gca cgc cca cgc cgc agc ccc gcc caa gat ggc aaa gtc tac atc aac   1254
Ala Arg Pro Arg Arg Ser Pro Ala Gln Asp Gly Lys Val Tyr Ile Asn
             75                  80                  85 atg cca ggc agg ggc tga tctatatatc tagattgcgg ccgcggtcat            1302
Met Pro Gly Arg Gly *
             90 agctgtttcc tgaacagatc ccgggtggca tccctgtgac ccctcccag tgcctctcct    1362 ggccctggaa gttgccactc cagtgcccac cagccttgtc ctaataaaat taagttgcat   1422
```

```
cattttgtct gactaggtgt ccttctataa tattatgggg tggaggggggg tggtatggag    1482 caagggcaa gttgggaaga caacctgtag ggcctgcggg gtctattggg aaccaagctg     1542
gagtgcagtg gcacaatctt ggctcactgc aatctccgcc tcctgggttc aagcgattct    1602
cctgcctcag cctcccgagt tgttgggatt ccaggcatgc atgaccaggc tcagctaatt    1662 tttgttttt tggtagagac ggggtttcac catattggcc aggctggtct ccaactccta     1722
atctcaggtg atctacccac cttggcctcc caaattgctg ggattacagg cgtgaaccac    1782
tgctcccttc cctgtccttc tgattttaaa ataactatac cagcaggagg acgtccagac    1842
acagcatagg ctacctggcc atgcccaacc ggtgggacat ttgagttgct tgcttggcac    1902
tgtcctctca tgcgttgggt ccactcagta gatgcctgtt gaattgggta cgcggccagc    1962
ttggctgtgg aatgtgtgtc agttagggtg tggaaagtcc ccaggctccc cagcaggcag    2022
aagtatgcaa agcatgcatc tcaattagtc agcaaccagg tgtggaaagt ccccaggctc    2082
cccagcaggc agaagtatgc aaagcatgca tctcaattag tcagcaacca tagtcccgcc    2142
cctaactccg cccatcccgc ccctaactcc gcccagttcc gcccattctc cgccccatgg    2202
ctgactaatt tttttatttt atgcagaggc cgaggccgcc tcggcctctg agctattcca    2262
gaagtagtga ggaggctttt ttggaggcct aggcttttgc aaaaagctcc tcgactgcat    2322
taatgaatcg gccaacgcgc ggggagaggc ggtttgcgta ttgggcgctc ttccgcttcc    2382
tcgctcactg actcgctgcg ctcggtcgtt cggctgcggc gagcggtatc agctcactca    2442
aaggcggtaa tacggttatc cacagaatca ggggataacg caggaaagaa catgtgagca    2502
aaaggccagc aaaaggccag gaaccgtaaa aaggccgcgt tgctggcgtt tttccatagg    2562
ctccgccccc ctgacgagca tcacaaaaat cgacgctcaa gtcagaggtg gcgaaacccg    2622
acaggactat aaagatacca ggcgtttccc cctggaagct ccctcgtgcg ctctcctgtt    2682
ccgaccctgc cgcttaccgg atacctgtcc gcctttctcc cttcgggaag cgtggcgctt    2742
tctcatagct cacgctgtag gtatctcagt tcggtgtagg tcgttcgctc caagctgggc    2802
tgtgtgcacg aaccccccgt tcagcccgac cgctgcgcct tatccggtaa ctatcgtctt    2862
gagtccaacc cggtaagaca cgacttatcg ccactggcag cagccactgg taacaggatt    2922
agcagagcga ggtatgtagg cggtgctaca gagttcttga agtggtggcc taactacggc    2982
tacactagaa gaacagtatt tggtatctgc gctctgctga agccagttac cttcggaaaa    3042
agagttggta gctcttgatc cggcaaacaa accaccgctg gtagcggtgg ttttttttgtt    3102 tgcaagcagc agattacgcg cagaaaaaaa ggatctcaag aagatccttt gatcttttct    3162
acggggtctg acgctcagtg gaacgaaaac tcacgttaag ggattttggt catgagatta    3222
tcaaaaagga tcttcaccta gatcctttta aattaaaaat gaagttttaa atcaatctaa    3282
agtatatatg agtaaacttg gtctgacagt taccaatgct taatcagtga ggcacctatc    3342
tcagcgatct gtctatttcg ttcatccata gttgcctgac tccccgtcgt gtagataact    3402
acgatacggg agggcttacc atctggcccc agtgctgcaa tgataccgcg agacccacgc    3462
tcaccggctc cagatttatc agcaataaac cagccagccg gaagggccga gcgcagaagt    3522
ggtcctgcaa ctttatccgc ctccatccag tctattaatt gttgccggga agctagagta    3582
agtagttcgc cagttaatag tttgcgcaac gttgttgcca ttgctacagg catcgtggtg    3642
tcacgctcgt cgtttggtat ggcttcattc agctccggtt cccaacgatc aaggcgagtt    3702
acatgatccc ccatgttgtg caaaaaagcg gttagctcct tcggtcctcc gatcgttgtc    3762
```

```
agaagtaagt tggccgcagt gttatcactc atggttatgg cagcactgca taattctctt      3822
actgtcatgc catccgtaag atgcttttct gtgactggtg agtactcaac caagtcattc      3882
tgagaatagt gtatgcggcg accgagttgc tcttgcccgg cgtcaatacg ggataatacc      3942
gcgccacata gcagaacttt aaaagtgctc atcattggaa acgttcttc ggggcgaaaa       4002
ctctcaagga tcttaccgct gttgagatcc agttcgatgt aacccactcg tgcacccaac      4062
tgatcttcag catcttttac tttcaccagc gtttctgggt gagcaaaaac aggaaggcaa      4122
aatgccgcaa aaagggaat aagggcgaca cggaaatgtt gaatactcat actcttcctt       4182
tttcaatatt attgaagcat ttatcagggt tattgtctca tgagcggata catatttgaa      4242
tgtatttaga aaataaaca aatagggg ttccgcgcacat ttccccgaaa agtgccacct       4302
gacgcgccct gtagcggcgc attaagcgcg gcgggtgtgg tggttacgcg cagcgtgacc      4362
gctacacttg ccagcgccct agcgcccgct cctttcgctt tcttcccttc ctttctcgcc      4422
acgttcgccg gctttccccg tcaagctcta atcggggggc tccctttagg gttccgattt      4482
agtgctttac ggcacctcga ccccaaaaaa cttgattagg gtgatggttc acgtagtggg      4542
ccatcgccct gatagacggt ttttcgccct tgacgttgg agtccacgtt ctttaatagt       4602
ggactcttgt tccaaactgg aacaacactc aaccctatct cggtctattc ttttgattta      4662
tagggatt tgccgatttc ggcctattgg ttaaaaaatg agctgattta caaaaatt         4722
aacgcgaatt ttaacaaaat att                                              4745

<210> SEQ ID NO 25
<211> LENGTH: 990
<212> TYPE: DNA
<213> ORGANISM: Artificial Sequence
<220> FEATURE:
<223> OTHER INFORMATION: CD3zeta-NKG2D
<400> SEQUENCE: 25
atgagagtga agttcagcag gagcgcagac gccccccgcgt accagcaggg ccagaaccag       60
ctctataacg agctcaatct aggacgaaga gaggagtacg atgttttgga caagagacgt      120
ggccgggacc ctgagatggg gggaaagccg cagagaagga gaaccctca ggaaggcctg       180
tacaatgaac tgcagaaaga taagatggcg gaggcctaca gtgagattgg gatgaaaggc      240
gagcgccgga ggggcaaggg gcacgatggc ctttaccagg gtctcagtac agccaccaag      300
gacacctacg acgcccttca catgcaggcc ctgcccctc gcggtggat tcgtggtcgg       360
aggtctcgac acagctggga gatgagtgaa tttcataatt ataacttgga tctgaagaag      420
agtgatttt caacacgatg gcaaaagcaa agatgtccag tagtcaaaag caaatgtaga       480
gaaaatgcat ctccatttt tttctgctgc ttcatcgctg tagccatggg aatccgtttc       540
attattatgg taacaatatg gagtgctgta ttcctaaact cattattcaa ccaagaagtt      600
caaattccct tgaccgaaag ttactgtggc ccatgtccta aaaactggat atgttacaaa      660
aataactgct accaattttt tgatgagagt aaaaactggt atgagagcca ggcttcttgt      720
atgtctcaaa atgccagcct tctgaaagta tacagcaaag aggaccagga tttacttaaa      780
ctggtgaagt catatcattg gatgggacta gtacacattc aacaaatgg atcttggcag       840
tgggaagatg gctccattct ctcacccaac ctactaacaa taattgaaat gcagaaggga      900
gactgtgcac tctatgcctc gagctttaaa ggctatatag aaaactgttc aactccaaat      960
acgtacatct gcatgcaaag gactgtgtaa                                        990
```

<210> SEQ ID NO 26
<211> LENGTH: 329
<212> TYPE: PRT
<213> ORGANISM: Artificial Sequence
<220> FEATURE:
<223> OTHER INFORMATION: amino acid sequence of CD3zeta-NKG2D

<400> SEQUENCE: 26

```
Met Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Gly Arg Asp Pro Glu Met Gly Gly
        35                  40                  45

Lys Pro Gln Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg Gly Trp Ile Arg Gly Arg Ser Arg His Ser Trp Glu Met
        115                 120                 125

Ser Glu Phe His Asn Tyr Asn Leu Asp Leu Lys Lys Ser Asp Phe Ser
    130                 135                 140

Thr Arg Trp Gln Lys Gln Arg Cys Pro Val Val Lys Ser Lys Cys Arg
145                 150                 155                 160

Glu Asn Ala Ser Pro Phe Phe Phe Cys Cys Phe Ile Ala Val Ala Met
                165                 170                 175

Gly Ile Arg Phe Ile Ile Met Val Thr Ile Trp Ser Ala Val Phe Leu
            180                 185                 190

Asn Ser Leu Phe Asn Gln Glu Val Gln Ile Pro Leu Thr Glu Ser Tyr
        195                 200                 205

Cys Gly Pro Cys Pro Lys Asn Trp Ile Cys Tyr Lys Asn Asn Cys Tyr
    210                 215                 220

Gln Phe Phe Asp Glu Ser Lys Asn Trp Tyr Glu Ser Gln Ala Ser Cys
225                 230                 235                 240

Met Ser Gln Asn Ala Ser Leu Leu Lys Val Tyr Ser Lys Glu Asp Gln
                245                 250                 255

Asp Leu Leu Lys Leu Val Lys Ser Tyr His Trp Met Gly Leu Val His
            260                 265                 270

Ile Pro Thr Asn Gly Ser Trp Gln Trp Glu Asp Gly Ser Ile Leu Ser
        275                 280                 285

Pro Asn Leu Leu Thr Ile Ile Glu Met Gln Lys Gly Asp Cys Ala Leu
    290                 295                 300

Tyr Ala Ser Ser Phe Lys Gly Tyr Ile Glu Asn Cys Ser Thr Pro Asn
305                 310                 315                 320

Thr Tyr Ile Cys Met Gln Arg Thr Val
                325
```

CHIMERIC RECEPTOR WITH NKG2D SPECIFICITY FOR USE IN CELL THERAPY AGAINST CANCER AND INFECTIOUS DISEASE

CROSS-REFERENCE TO RELATED APPLICATIONS

This application is a continuation of U.S. patent application Ser. No. 15/337,854, filed Oct. 28, 2016, which is a continuation of U.S. patent application Ser. No. 14/764,070, filed Jul. 28, 2015, now issued as U.S. Pat. No. 9,511,092, which is the United States National Phase Application under 35 USC § 371 of International Patent Application No. PCT/US2014/013292, filed on Jan. 28, 2014, which published as WO 2014/117121 on Jul. 31, 2014 and claims the benefit of U.S. Provisional Patent Application No. 61/757,481, filed Jan. 28, 2013. The entirety of each of these applications are incorporated by reference herein.

SEQUENCE LISTING

The instant application contains a Sequence Listing which has been submitted in ASCII format via EFS-Web and is hereby incorporated by reference in its entirety. Said ASCII copy, created on Jan. 24, 2014, is named PTO-Seq_listing-JUDE51.TXT, and is 37,845 bytes in size.

1. BACKGROUND OF THE INVENTION

1.1 Field of the Invention

Natural killer (NK) cells can recognize tumor cells as targets and as such may be useful for immunotherapy of cancer (Vivier et al., 2011, Science 331:44-49; Ruggeri et al., 2002, Science 295:2097-2100; Cooley et al., 2010, Blood 116:2411-2419; Miller et al., 2005, Blood 105:3051-3057; Rubnitz et al., 2010, J Clin Oncol. 28:955-959). Infusions of NK cells have been used to treat patients with various forms of cancer (Vivier et al., 2011, Science 331:44-49; Caligiuri, 2008, Blood 112(3):461-469; Ruggeri et al., 2002, Science 295:2097-2100; Miller et al., 2005, Blood 105:3051-3057). Methods are available that make it possible to obtain a large number of human NK cells that demonstrate a higher anti-tumor capacity than that of non-expanded NK cells (see U.S. Pat. No. 7,435,596; Imai et al., 2005, Blood 106:376-83; Fujisaki et al., 2009, Cancer Res. 69: 4010-4017; Cho et al., 2010, Clin Cancer Res. 16:3901-3909).

The capacity of NK cells to kill tumor cells depends on the combined effect of inhibitory and stimulatory signals delivered through surface receptors (Caligiuri, 2008, Blood 112(3):461-469; Vivier et al., 2011, Science 331:44-49). On the one hand, the interaction between some members of the killer immunoglobulin-like receptor (KIR) family on NK cells and cognate HLA Class I molecules on potential target cells produces inhibitory signals, a mechanism that prevents the killing of autologous cells (Vivier et al., 2011, Science 331:44-49; Caligiuri, 2008, Blood 112(3):461-469). On the other hand, signals from activating receptors are triggered by ligands expressed predominantly by virally-infected and tumor cells; hence, these receptors are central to the capacity of NK cells to recognize and lyse unhealthy cells (Caligiuri, 2008, Blood 112(3):461-469; Vivier et al., 2011, Science 331:44-49).

A key receptor for NK cell activation is Natural killer Group 2 member D (NKG2D), a type II transmembrane-anchored C-type lectin-like protein expressed in all NK cells and in some T cell subsets (Ho et al., 1998, Proc. Natl. Acad. Sci. USA. 95:6320-5; Bauer et al., 1999, Science 285:727-729; Champsaur et al., 2010, Immunol. Rev. 235:267-285). NKG2D has multiple ligands including MHC class I chain-related A (MICA), MICB and several UL-16-binding proteins (ULBPs) which are preferentially expressed after cellular stress, infection or DNA damage (Bauer et al., 1999, Science 285:727-729; Gasser et al., 2005, Nature 436:1186-1190).

NKG2D ligands are widely expressed among cancer cells (Groh et al., 1999, Proc. Natl. Acad. Sci. USA. 96:6879-6884; Pende et al., 2002, Cancer Res. 62:6178-6186). Indeed, there is strong evidence for an important role of NKG2D in NK cell-mediated anti-tumor activity in vitro and in animal models (Vivier et al., 2011, Science 331:44-49; Champsaur et al., 2010, Immunol. Rev. 235:267-285; Smyth et al., 2005, J. Exp. Med. 202:583-588; Routes et al., 2005, J. Exp. Med. 202:1477-82; Stem-Ginossar et al., 2008, Nat. Immunol 9:1065-1073; Karimi et al., 2005, J. Immunol. 175:7819-7828; Guerra et al., 2008, Immunity 28:571-580; Cho et al., 2010, Clin. Cancer Res. 16:3901-3909; Raulet, 2003, Nat. Rev. Immunol. 3:781-790; Bryceson et al., 2008, Eur. J. Immunol. 38:2957-2961).

NKG2D is associated with DNAX-activating protein 10 (DAP10), which promotes and stabilizes its surface membrane expression (Wu et al., 1999, Science 285:730-732; Diefenbach et al., 2002, Nat. Immunol. 3:1142-1149; Garrity et al., 2005, Proc. Natl. Acad. Sci. USA. 102:7641-7646; Horng et al., 2007, Nat. Immunol. 8:1345-1352; Park et al., 2011, Blood 118:3019-3027). NKG2D lacks a signaling motif in its cytoplasmic domain; signal transduction occurs upon ligation via the phosphorylation of DAP10, which recruits downstream signaling effector molecules and, ultimately, cytotoxicity (Wu et al., 1999, Science 285:730-732; Upshaw et al., 2006, Nat. Immunol. 7:524-532). U.S. Pat. No. 7,994,298 discloses the use of chimeric receptors comprising an extracellular domain comprising the C-type lectin-like natural killer cell receptor, NKG2D or associated protein, DAP10, fused to an immune signaling receptor, CD3 zeta, for expression in T cells.

Despite the promise that NK cells have shown for use in anti-cancer therapy, some cancer subtypes remain relatively insensitive even to activated NK cells. As a result, genetic modification of T cells, rather than NK cells, is used to express chimeric receptors for redirecting T cells against tumor cells for anti-cancer therapy. For use in clinical applications, however, T cells have the disadvantage that that they may cause potentially fatal graft-versus-host disease after infusion if they are not obtained from the patient being treated, i.e., autologous cells.

2. BRIEF SUMMARY OF THE INVENTION

Provided herein is an artificial chimeric receptor complex composed of an NK receptor, NKG2D, and two stimulatory molecules, DAP10 and CD3 zeta (also called "CD3zeta" or "CD3z"); this artificial chimeric receptor is referred to herein as "NKG2D-DAP10-CD3zeta." The invention is based, in part, on the applicants' discovery and design of a compositions and methods for making and using a chimeric receptor complex that enhances the cytotoxicity and antitumor capacity of NK cells and hence their therapeutic efficacy. In particular, the applicants have designed and constructed a polynucleotide encoding NKG2D, DAP10 and CD3zeta, expressed it in activated NK cells, and demonstrated its ability to boost the signaling anti-cancer potential of NK cells in vitro and in vivo. The NKG2D-DAP10-CD3zeta compositions and methods provided herein may be used in immunotherapy against cancer, as well as infectious diseases. Because no precedent exists for an artificial chimeric receptors that is highly active in NK cells and useful for NK cell immunotherapy, the discovery of NKG2D-DAP10-CD3zeta was highly unexpected.

Further provided are compositions and methods for the use of NKG2D-DAP10-CD3zeta complex to enhance NK cell antitumor capacity for anti-cancer therapy. The invention also encompasses methods for the use of NKG2D-DAP10-CD3zeta polypeptides, vectors and cells in methods for treating cancer and other proliferative disorders, as well as infectious diseases.

When expressed in activated NK cells, this chimeric antigen receptor complex markedly enhances the capacity of NK cells to kill tumor cells in vitro and in animal models. The chimeric antigen receptor complex does not significantly increase the cytotoxicity of NK cells against normal cells and does not present a disadvantage over infusion of non-genetically modified NK cells.

The NKG2D-DAP10-CD3zeta polynucleotide can be expressed in NK cells either using a retroviral vector, or by electroporation of the corresponding mRNA. The electroporation method greatly facilitates its use in clinical applications. Because expression by electroporation does not require prior cell culture, it is possible to rapidly adapt the technology to large-scale clinical conditions.

Provided herein is a polynucleotide encoding: (a) a CD3zeta signaling domain, (b) an extracellular ligand-binding domain comprising a Natural Killer Group 2 member D receptor (NKG2D), (c) a DNAX-activating protein 10 (DAP10), wherein a nucleotide sequence encoding said DAP10 is operably linked to a nucleotide sequence comprising an internal ribosome entry site (IRES). In one embodiment, the polynucleotide is an mRNA. In another embodiment, the polynucleotide is operably linked to at least one regulatory element for the expression of the chimeric antigen receptor complex.

In another embodiment, the CD3 zeta signaling domain comprises the amino acid sequence of SEQ ID NO:10. In another embodiment, the CD3 zeta signaling domain is encoded by the nucleic acid sequence of SEQ ID NO:9. In another embodiment, the NKG2D receptor domain comprises the amino acid sequence of SEQ ID NO:12. In yet another embodiment, the NKG2D receptor domain is encoded by the nucleic acid sequence of SEQ ID NO:11. In another embodiment, the DAP10 comprises the amino acid sequence of SEQ ID NO:14. In another embodiment, the DAP10 is encoded by the nucleic acid sequence of SEQ ID NO:13. In yet another embodiment, the CD3 zeta signaling domain comprises the amino acid sequence of SEQ ID NO:10, the NKG2D receptor domain comprises the amino acid sequence of SEQ ID NO:12, and the DAP10 comprises the amino acid sequence of SEQ ID NO:14.

Also provided herein is an NKG2D-DAP10-CD3zeta chimeric receptor expression comprising a polynucleotide encoding: (a) a CD3 zeta signaling domain, (b) an NKG2D extracellular ligand-binding domain, and (c) a DAP10, wherein a nucleotide sequence encoding the DAP10 is operably linked to a nucleotide sequence comprising an IRES, and wherein the polynucleotide is operatively linked to at least one regulatory element for expression of the NKG2D-DAP10-CD3zeta chimeric receptor. In one embodiment, the vector is a retrovirus. In a specific embodiment, the vector is a murine stem cell virus (MSCV).

Also provided herein is an isolated genetically engineered cell comprising a polynucleotide encoding: (a) a CD3 zeta signaling domain, (b) an NKG2D extracellular ligand-binding domain, (c) a nucleotide sequence comprising an internal ribosome entry site (IRES), and (d) a DAP10, wherein a nucleotide sequence encoding the DAP10 is operably linked to a nucleotide sequence comprising an IRES, and wherein the polynucleotide is operatively linked to at least one regulatory element for expression of the chimeric receptor. In one embodiment, the isolated genetically engineered cell is a natural killer (NK) cell. In another embodiment, the isolated genetically engineered cell is a T lymphocyte. In another embodiment, the isolated genetically engineered cell is a human cell. In another embodiment, the isolated genetically engineered cell is an autologous cell isolated from a patient having a cancer or an infectious disease. In yet another embodiment, the isolated genetically engineered cell is an allogenic cell isolated from a donor. In yet another embodiment, the isolated genetically engineered cell is an autologous cell isolated from a patient having a cancer, wherein the cancer is a T-cell acute lymphocytic leukemia (ALL), a B-cell acute lymphocytic leukemia, a lymphoblastic leukemia, a B-cell chronic lymphocytic leukemia or a B-cell non-Hodgkin's lymphoma, prostate carcinoma, rhabdomyosarcoma, neuroblastoma, Ewing sarcoma, colon carcinoma, gastric carcinoma, lung squamous cell carcinoma, hepatoma, or breast carcinoma.

Further provided herein is a method of increasing or enhancing cytotoxicity of an NK cell or T lymphocyte in a mammal in need thereof comprising administering to said mammal an expanded population of NK cells or T lymphocytes, wherein said NK cells or T lymphocytes comprise a polynucleotide encoding: (a) a CD3 zeta signaling domain, (b) an NKG2D receptor extracellular ligand-binding domain, and (c) a DAP10, wherein a nucleic acid sequence encoding the DAP10 is operably linked to an IRES for expressing the DAP10. In one embodiment of this method, the cytotoxicity of the NK cell is increased or enhanced without significant increase in cytotoxic activity against non-tumor cells in said mammal. In another embodiment, the cytotoxicity against non-tumor cells is less than 20% cytotoxicity.

In one embodiment of this method, the NK cells are donor NK cells. In a further embodiment of this method the NK cells are autologous NK cells. In another embodiment, the CD3 zeta signaling domain comprises the amino acid sequence of SEQ ID NO:10. In yet another embodiment, the CD3 zeta signaling domain is encoded by the nucleic acid sequence of SEQ ID NO:9. In yet another embodiment, the NKG2D receptor domain comprises the amino acid sequence of SEQ ID NO:12. In yet another embodiment, the NKG2D receptor domain is encoded by the nucleic acid sequence of SEQ ID NO:11. In yet another embodiment, the DAP10 comprises the amino acid sequence of SEQ ID NO:14. In yet another embodiment, the DAP10 is encoded by the nucleic acid sequence of SEQ ID NO:13. In yet another embodiment, the CD3 zeta signaling domain comprises the amino acid sequence of SEQ ID NO:10, the NKG2D receptor domain comprises the amino acid sequence of SEQ ID NO:12, and the DAP10 comprises the amino acid sequence of SEQ ID NO:14. In another embodiment, the CD3 zeta signaling domain is encoded by the nucleic acid sequence of SEQ ID NO:9, the NKG2D receptor domain is encoded by the nucleic acid sequence of SEQ ID NO:11, and the DAP10 is encoded by the nucleic acid sequence of SEQ ID NO:13. In another embodiment, the mammal is suffering from a cancer of B-cell origin. In another embodiment, the cancer of B-cell origin is a B-lineage acute lymphoblastic leukemia, B-cell chronic lymphocytic leukemia or a B-cell non-Hodgkin's lymphoma. In yet another embodiment, the mammal is suffering from lung cancer, melanoma, breast cancer, prostate cancer, colon cancer, renal cell carcinoma, ovarian cancer, neuroblastoma, rhabdomyosarcoma, leukemia and lymphoma, acute lymphoblastic leukemia, small cell lung cancer, Hodgkin's lymphoma, or childhood acute lymphoblastic leukemia.

Also provided herein is a method for reducing tumor burden in a mammal, said method comprising administering to a mammal in need thereof a therapeutically effective amount of an expanded population of NK cells, wherein said NK cells comprise a polynucleotide comprising: (a) a nucleotide sequence encoding a CD3 zeta signaling domain, (b) a nucleotide sequence encoding an extracellular ligand-binding domain comprising an NKG2D receptor, (c) a nucleotide sequence comprising an IRES; and (d) a nucleotide sequence encoding a DAP10 operably linked to said IRES for expressing the DAP10.

Further provided herein is a method for treating, protecting against, or ameliorating a cancer or an infectious disease in a mammal, said method comprising administering to a mammal in need thereof a therapeutically effective amount of an expanded population of NK cells, wherein said NK cells comprise a polynucleotide comprising: (a) a nucleotide sequence encoding a CD3 zeta signaling domain, (b) a nucleotide sequence encoding an extracellular ligand-binding domain comprising an NKG2D receptor, (c) a nucleotide sequence comprising an IRES; and (d) a nucleotide sequence encoding a DAP10 operably linked to said IRES for expressing the DAP10.

In another embodiment, a method is provided for treating, protecting against, or ameliorating a cancer or an infectious disease in a mammal, said method comprising administering to a mammal in need thereof a therapeutically effective amount of an expanded population of NK cells or T cells, wherein said NK cells or T cells comprise (a) a first mRNA encoding an NKG2D receptor domain and a CD3 zeta signaling domain and (b) a second mRNA encoding a DAP10 polypeptide, which first and second mRNA were delivered into said NK cell or T cell by electroporation. In a specific embodiment of this method, the first mRNA comprises SEQ ID NO:25. In another specific embodiment, the second mRNA comprises SEQ ID NO:26. In another specific embodiment, the first mRNA comprises SEQ ID NO:25 and the second mRNA comprises SEQ ID NO:26.

In one embodiment of the methods of the invention, the NK cells are donor NK cells. In another embodiment, the NK cells are autologous NK cells. In another embodiment, the CD3 zeta signaling domain comprises the amino acid sequence of SEQ ID NO:10. In yet another embodiment, the CD3 zeta signaling domain is encoded by the nucleic acid sequence of SEQ ID NO:9. In yet another embodiment, the NKG2D receptor domain comprises the amino acid sequence of SEQ ID NO:12. In yet another embodiment, the NKG2D receptor domain is encoded by the nucleic acid sequence of SEQ ID NO:11. In yet another embodiment, the DAP10 comprises the amino acid sequence of SEQ ID NO:14. In yet another embodiment, the DAP10 is encoded by the nucleic acid sequence of SEQ ID NO:13. In yet another embodiment, the CD3 zeta signaling domain comprises the amino acid sequence of SEQ ID NO:10, the NKG2D receptor domain comprises the amino acid sequence of SEQ ID NO:12, and the DAP10 comprises the amino acid sequence of SEQ ID NO:14. In another embodiment, the CD3 zeta signaling domain is encoded by the nucleic acid sequence of SEQ ID NO:9, the NKG2D receptor domain is encoded by the nucleic acid sequence of SEQ ID NO:11, and the DAP10 is encoded by the nucleic acid sequence of SEQ ID NO:13. In another embodiment, the mammal is suffering from a cancer of B-cell origin. In another embodiment, the cancer of B-cell origin is a B-lineage acute lymphoblastic leukemia, B-cell chronic lymphocytic leukemia or a B-cell non-Hodgkin's lymphoma. In yet another embodiment, the mammal is suffering from lung cancer, melanoma, breast cancer, prostate cancer, colon cancer, renal cell carcinoma, ovarian cancer, neuroblastoma, rhabdomyosarcoma, leukemia and lymphoma, acute lymphoblastic leukemia, small cell lung cancer, Hodgkin's lymphoma, or childhood acute lymphoblastic leukemia.

Further provided herein is a method for treating a mammal suffering from cancer or an infectious disease comprising administering to said mammal an NK cell or a T lymphocyte, wherein the NK cell or T lymphocyte comprises vector comprising a polynucleotide encoding: (a) a nucleotide sequence encoding a CD3 zeta signaling domain, (b) a nucleotide sequence encoding an extracellular ligand-binding domain comprising an NKG2D receptor, and (c) a nucleotide sequence encoding a DAP10 operably linked to an internal ribosome entry site (IRES) for expression of the DAP10, wherein the polynucleotide is operatively linked to at least one regulatory element for expression of the chimeric receptor.

In one embodiment, the vector is a retrovirus. In another embodiment, the vector is an MSCV. In another embodiment, the cancer is of B-cell origin. In another embodiment, the cancer is selected from the group consisting of B-lineage acute lymphoblastic leukemia, B-cell chronic lymphocytic leukemia and B-cell non-Hodgkin's lymphoma. In another embodiment, the cancer is selected from the group consisting of lung cancer, melanoma, breast cancer, prostate cancer, colon cancer, renal cell carcinoma, ovarian cancer, neuroblastoma, rhabdomyosarcoma, lymphoma, acute lymphoblastic leukemia, small cell lung carcinoma, Hodgkin's lymphoma, childhood acute lymphoblastic leukemia, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, pancreatic cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilms' tumor, cervical cancer, testicular tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, retinoblastoma, acute lymphocytic leukemia, acute myelocytic leukemia, chronic leukemia, polycythemia vera, lymphoma, multiple myeloma, Waldenström's macroglobulinemia, and heavy chain disease. In another embodiment, the cancer is selected from the group consisting of T-cell ALL, B-cell ALL, osteosarcoma, prostate carcinoma, rhabdomyosarcoma, neuroblastoma, Ewing sarcoma, colon carcinoma, gastric carcinoma, lung squamous cell carcinoma, hepatoma, and breast carcinoma.

3. DESCRIPTION OF THE SEQUENCE LISTING

SEQ ID NO: 1 is the nucleotide sequence of the forward primer for the cloning of the cytoplasmic domain of human CD3 zeta.

SEQ ID NO: 2 is the nucleotide sequence of the reverse primer for the cloning of the cytoplasmic domain of human CD3 zeta.

SEQ ID NO: 3 is the nucleotide sequence of the forward primer for the cloning of human NKG2D.

SEQ ID NO: 4 is the nucleotide sequence of the reverse primer for the cloning of human NKG2D.

SEQ ID NO: 5 is the nucleotide sequence of the forward primer for the cloning of human DAP10 and the FLAG-tag.

SEQ ID NO: 6 is the nucleotide sequence of the reverse primer for the cloning of human DAP10 and the FLAG-tag.

SEQ ID NO: 7 is the nucleotide sequence of pMSCV-CD3zeta-NKG2D-IRES-DAP10-FLAG-tag.

SEQ ID NO: 8 is the nucleotide sequence of pMSCV-CD3zeta-NKG2D-IRES-DAP10.

SEQ ID NO: 9 is the nucleotide sequence of the cDNA encoding the cytoplasmic domain of human CD3 zeta of the chimeric receptor.

SEQ ID NO: 10 is the amino acid sequence of the cytoplasmic domain of human CD3 zeta of the chimeric receptor.

SEQ ID NO: 11 is the nucleotide sequence of the cDNA encoding human NKG2D of the chimeric receptor.

SEQ ID NO: 12 is the amino acid sequence of human NKG2D of the chimeric receptor.

SEQ ID NO: 13 is the nucleotide sequence of human DAP10 cDNA.

SEQ ID NO: 14 is the amino acid sequence of human DAP10.

SEQ ID NO: 15 is the nucleotide sequence of the FLAG-tag.

SEQ ID NO: 16 is the amino acid sequence of the FLAG-tag.

SEQ ID NO: 17 is the nucleotide sequence of DAP10-FLAG-tag.

SEQ ID NO: 18 is the amino acid sequence of DAP10-FLAG-tag.

SEQ ID NO: 19 is the nucleotide sequence of CD3zeta-NKG2D-IRES-DAP10-FLAG-tag.

SEQ ID NO: 20 is the nucleotide sequence of CD3zeta-NKG2D-IRES-DAP10.

SEQ ID NO: 21 is the nucleotide sequence of human NKG2D cDNA.

SEQ ID NO: 22 is the amino acid sequence of human NKG2D.

SEQ ID NO: 23 is the nucleotide sequence of pCMV6-XL5-CD3zeta-NKG2D.

SEQ ID NO: 24 is the nucleotide sequence of pCMV6-XL5-DAP10.

SEQ ID NO: 25 is the nucleotide sequence of CD3zeta-NKG2D mRNA.

SEQ ID NO: 26 is the nucleotide sequence of DAP10 mRNA.

4. BRIEF DESCRIPTION OF THE DRAWINGS

FIGS. 1A-1E: show a recombinant polynucleotide chimeric receptor of the invention, NKG2D-DAP10-CD3zeta in a retroviral construct, and its expression in NK cells. 1A: Schematic representation of the NKG2D-DAP10-CD3zeta receptor and retroviral vector construct. 1B: Mean fluorescence intensity (MFI) of NKG2D expression in expanded NK cells from 21 donors transduced with a vector containing green fluorescent protein (GFP) only ("mock") or a vector containing the NKG2D-DAP10-CD3zeta receptor construct; horizontal lines indicate median values. To measure levels of NKG2D, an anti-NKG2D antibody conjugated to PerCP was used, which in preliminary experiments gave a weaker signal and allowed to better detect differences in NKG2D expression. 1C: MFI of NKG2D expression in expanded NK cells from 6 donors transduced with either a NKG2D-CD3zeta or a NKG2D-DAP10-CD3zeta □construct. 1D: Flow cytometry dot plots illustrate expression of NKG2D and DAP10 detected with an anti-FLAG antibody in mock- and NKG2D-DAP10-CD3zeta—transduced NK cells. 1E: Western blot of mock- and NKG2D-DAP10-CD3zeta construct-transduced NK cells. Mock- and NKG2D-DAP10-CD3zeta construct transduced NK cells were incubated with 0.1 μM sodium orthovanadate and 0.034% $H_2O_2$ at 37° C. for 10 minutes before cell lysate preparation under reducing and non-reducing conditions and Western blotting. An anti-human CD3zeta phospho (pY83) monoclonal antibody (clone EP776(2)Y; Epitomics, Burlingame, Calif.) followed by a goat anti-rabbit IgG horseradish peroxidase-conjugated second antibody was used to detect endogenous and chimeric phospho-CD3zeta□proteins.

FIGS. 2A-2D: Expression of NKG2D-DAP10-CD3zeta receptors increases tumor cell killing by NK activated NK cells. 2A: Percent cytotoxicity of mock- and NKG2D-DAP10-CD3zeta-transduced NK cells against leukemia cell lines (CEM-C7, MOLT-4, Jurkat, REH, and OP-1), and solid tumor-derived cell lines (U-2 OS, MG-36, HOS, DU 145, PC-3, LNCaP, RH18, RH30, TE32, RH36, SKNSH, TC71, Km12L4, SNU1, SW900, HepG2 and MCF7). A total of 65 experiments were performed using NK cells expanded from 14 donors at an E:T of 1:1 or 1:2; cell killing was measured after 4 hours of co-culture 4. 2B: Flow cytometric dot plots illustrate the assay used to measure cell killing. Results with one leukemia cell lines (REH, top row) and one osteosarcoma cell line (U-2 OS, bottom row) are shown. Tumor cells were either cultured alone (left panels), with mock-transduced NK cells (middle panels), or with NK cells transduced with the NKG2D-DAP10-CD3zeta receptor. Residual viable target cells are in the bottom right region of each panel. 2C: Percent cytotoxicity of mock- and NKG2D-DAP10-CD3zeta-transduced NK cells against selected tumor cell lines. 2D: Percent cytotoxicity of mock- and NKG2D-DAP10-CD3zeta-transduced NK cells from 3 donors against non-transformed peripheral blood mononucleated cells (PBMC) and bone-marrow-derived mesenchymal stromal cells (MSC); P>0.05.

FIGS. 3A-3D: Relation between NKG2D-DAP10-CD3zeta ligation and increased cytotoxicity. 3A: Relation between expression of NKG2D ligands (NKG2DL) as measured by mean fluorescence intensity (MFI) after staining cells with human recombinant NKG2D/Ig Fc reagent and increase in cytotoxicity by NK cells expressing the NKG2D-DAP10-CD3zeta receptor as compared to mock-transduced NK cells. The median value of 43% was used to divide cell lines into 2 groups; P>0.05. 3B: Pre-incubation of NK cells with an inhibitory anti-NKG2D antibody (clone 149810; R&D) abrogated the gains in cytotoxicity produced by the expression of NKG2D-DAP10-CD3zeta in NK cells. Mock- and NKG2D-DAP10-CD3zeta-transduced NK cells were incubated with anti-NKG2D, anti-CD56 or an isotype-matched non-reactive antibody for 10 minutes; 4-hour cytotoxicity against the U-2 OS cell line at 1:1 ratio was tested. Bars represent mean (±SD) of triplicate measurements. 3C: Incubation of NK cells with a biotin-conjugated anti-NKG2D agonistic antibody (clone 1D11; eBioscience) and anti-biotin beads (MACSiBeads; Miltenyi Biotec) induced degranulation, which was significantly higher in NK cells expressing NKG2D-DAP10-CD3zeta. Percentage of CD56+ cells from 6 donors expressing CD107a after 4 hours of anti-NKG2D stimulation is shown. 3D: Flow cytometric dot plots illustrating CD107a expression on mock- or NKG2D-DAP10-CD3zeta-transduced CD56+ cells.

FIGS. 4A-4C: Cellular consequences of NKG2D-DAP10-CD3zeta signaling. 4A: Mock- and NKG2D-DAP10-CD3zeta-transduced NK cells were incubated with a biotin-conjugated anti-NKG2D agonistic antibody (clone 1D11; eBioscience) and anti-biotin beads (MACSiBeads; Miltenyi Biotec) for 1 hour and cell lysates were analyzed by Kinex Antibody Microarray (Kinexus, Vancouver, Calif.). Of 809 anti-phosphorprotein antibodies tested, shown are those whose signals had a Z-ratio ≥1 and a % Error Range ≤50. Bars indicate percent signal change in NK cells expressing NKG2D-DAP10-CD3zeta as compared to the normalized intensity in mock-transduced NK cells. 4B: Mock- and NKG2D-DAP10-CD3zeta-transduced NK cells from 3 donors were incubated with a biotin-conjugated anti-NKG2D agonistic antibody (clone 1D11; eBioscience) and anti-biotin beads (MACSiBeads; Miltenyi Biotec). Concentration of IFNγ and GM-CSF in the supernatants collected 4, 8 and 16 hours after initiation of stimulation was measured by Luminex (Merck Millipore). Data of the remaining cytokines/chemokines measured are presented in FIG. 7 and Table 1. 4C: Degranulation in mock- and NKG2D-DAP10-CD3zeta-transduced NK cells after continuous stimulation with anti-NKG2D. NK cells were incubated with anti-NKG2D and beads as described in A. After 4, 24 and 48 hours, expression of CD107a in CD56+ cells was measured by flow cytometry. Results from experiments with NK cells from 2 donors are shown.

Figure 5:
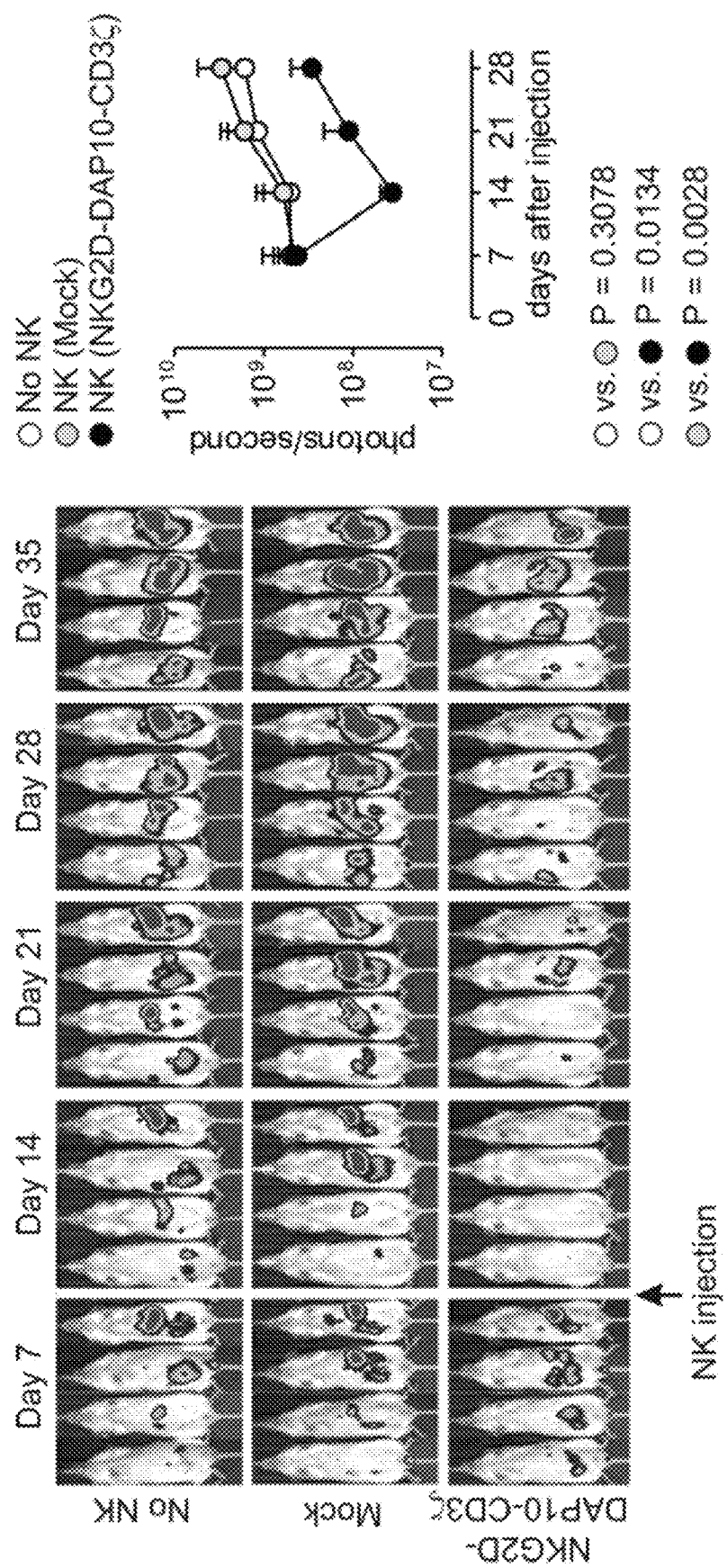

FIG. 5: Anti-tumor capacity of NKG2D-DAP10-CD3zeta-transduced NK cells in a xenograft model of osteosarcoma. Luciferase-labeled U-2 OS cells ($2\times10^5$) were injected intraperitoneally (i.p.) in 12 immunodeficient (NOD/scid-IL2Rgnull) mice. Control mice ("No NK"; n=4) received no treatment (top row); the remaining 8 mice received a single i.p. injection of either mock-transduced ("Mock," middle row) or NKG2D-DAP10-CD3zeta-transduced $3\times10^6$ NK cells ("NKG2D-DAP10-CD3zeta," bottom row), followed by four daily IL-2 i.p. injection. Photoluminescence signals were measured at weekly intervals with a Xenogen IVIS-200 system (Caliper Life Sciences, with imaging beginning 5 minutes after i.p. injection of an aqueous solution of D-luciferin potassium salt (3 mg/mouse). Right graph shows means (±SD) measurements of photons/second quantified using the Living Image 3.0 software program (analyzed by 2-way ANOVA).

Figure 6B:
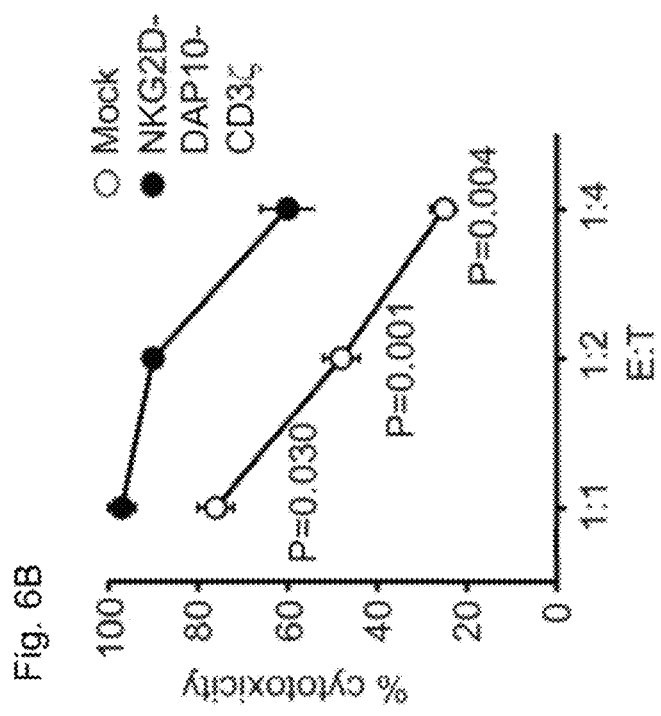
Figure 6A:
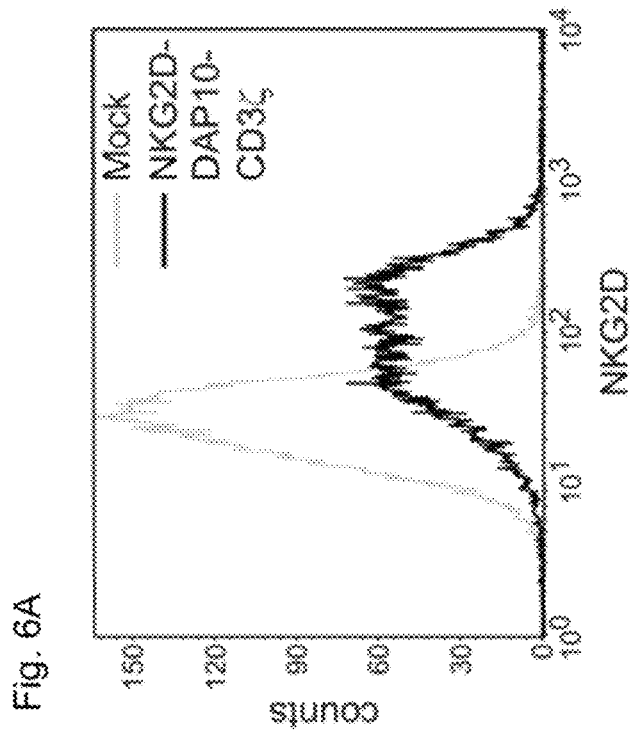

FIGS. 6A-6B: Expression of NKG2D-DAP10-CD3zeta by electroporation. 6A: Flow cytometric analysis of NKG2D expression in activated CD56+ CD3-NK cells 24 hours after electroporation with NKG2D-CD3zeta and DAP10 mRNA (NKG2D-DAP10-CD3zeta☐ or no mRNA ("mock"). 6B: Killing of U2-OS cells after 4-hour co-culture with NK cells electroporated with NKG2D-CD3zeta and DAP10 mRNA or mock-electroporated at the indicated E:T ratios. Each symbol corresponds to mean (±SD) of 3 co-cultures; P value at each E:T ratio by t test is shown.

Figure 7:
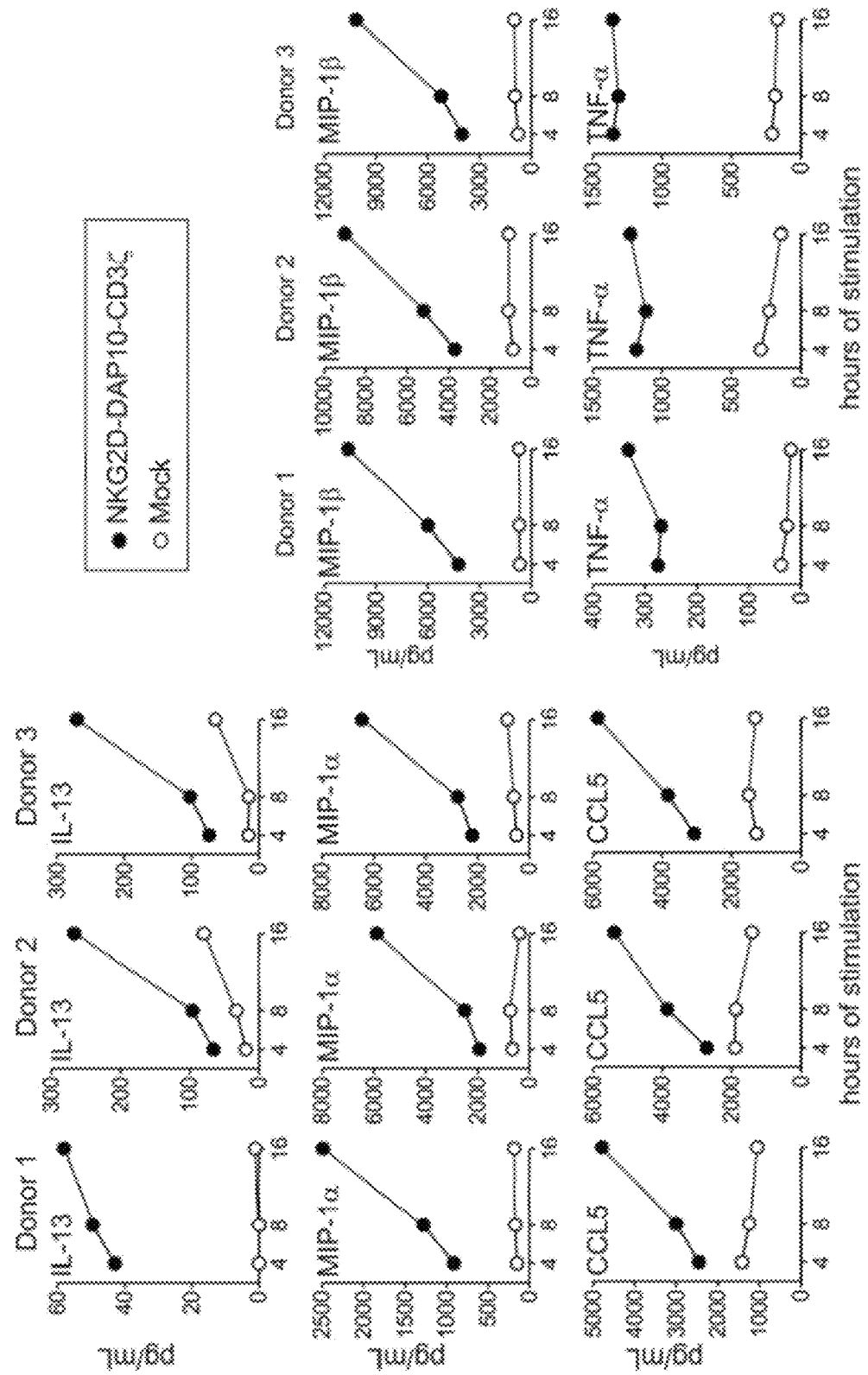

FIG. 7: Cytokine/chemokine secretion of mock- and NKG2D-DAP10-CD3zeta-transduced NK cells from 3 donors after incubation with a biotin-conjugated anti-NKG2D agonistic antibody (clone 1D11; eBioscience) and anti-biotin beads (MACSiBeads; Miltenyi Biotec) (see also FIG. 4 and Table 1).

5. DETAILED DESCRIPTION OF THE INVENTION

The invention relates to compositions and methods for use of a chimeric receptor complex with NKG2D specificity in cell therapy for treating cancer and infectious disease. The chimeric receptor complex, herein called "NKG2D-DAP10-CD3zeta," comprises an extracellular ligand-binding domain comprising a Natural Killer Group 2 member D receptor (NKG2D), (b) DNAX-activating protein 10 (DAP10), and (c) a CD3zeta signaling domain. The present invention provides compositions comprising polynucleotides for expressing NKG2D-DAP10-CD3zeta, vectors and isolated and/or recombinant cells comprising such polynucleotides, and methods for the use of NKG2D-DAP10-CD3zeta cell therapy for the treatment of cancer and infectious diseases.

Described below are compositions and methods relating to immunotherapy against cancer, as well as infectious diseases. In particular, Sections 5.1, 5.2, 5.3, and 5.4 describe polypeptides, polynucleotides, vectors, genetically engineered cells, and pharmaceutical compositions respectively, which may be used in accordance with the invention, and methods for their isolation, preparation, and/or generation. Section 5.5 describes therapeutic methods for using the polypeptides, polynucleotides, vectors, and genetically engineered cells to protect against, ameliorate, and/or treat cancer and infectious disease. Target cancers and infectious diseases that may be to protect against, ameliorate, and/or treat cancer and infectious disease using the compositions and methods of the invention are described in Sections 5.5.1 and 5.5.2.

Terminology

In describing and claiming the invention, the following terms should be understood as follows.

As used herein, unless otherwise specified, the terms "protein(s)" and "polypeptide(s)" interchangeably refer to a chain of amino acids linked together by peptide bonds. In some embodiments, the terms "protein(s)" and "polypeptide(s)" refer to a macromolecule which comprises amino acids that are linked together by peptide bonds.

The term "chimeric receptor" as used herein refers to a cell-surface receptor comprising at least two polypeptide domains not naturally found together on a single protein. For example, the NKG2D-DAP10-CD3zeta chimeric receptor described herein comprises an NKG2D extracellular ligand binding domain and a CD3zeta cytoplasmic signaling domain, which are not found together on a single protein. The chimeric receptors of the present invention are intended primarily for use with NK cells and T cells.

The term "chimeric receptor complex" as used herein refers to a first polypeptide, which may comprise at least two polypeptide domains in a combination that are not naturally found together on a single protein, which first polypeptide is associated with a second polypeptide, for example, an adaptor polypeptide, a signaling molecule, or a stimulatory molecule. The NKG2D-DAP10-CD3zeta chimeric receptor complex described herein comprises a first polypeptide comprising an NKG2D receptor extracellular ligand-binding domain and a CD3zeta signaling domain, and second polypeptide comprising a DAP10 stimulatory molecule. The chimeric receptor complexes of the present invention are intended primarily for use with NK cells and T cells.

A "stimulatory molecule" refers to a molecule other than a receptor or a receptor ligand which is contributes to signal transduction.

As used herein, the terms "nucleic acid," "nucleotide," and "polynucleotide" include deoxyribonucleotides, deoxyribonucleic acids, ribonucleotides, and ribonucleic acids, and polymeric forms thereof, and includes either single- or double-stranded forms. Nucleic acids include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleic acid analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), locked-nucleic acids (LNAs), and the like.

An "isolated" nucleic acid sequence, polynucleotide or nucleotide sequence is one which is separated from other nucleic acid molecules which are present in a natural source of the nucleic acid sequence, polynucleotide or nucleotide sequence. Moreover, an "isolated" nucleic acid sequence, polynucleotide or nucleotide sequence, such as a cDNA molecule, can be substantially free of other cellular material or culture medium when produced by recombinant techniques, or substantially free of chemical precursors when chemically synthesized. In certain embodiments, an "isolated" nucleic acid sequence, polynucleotide or nucleotide sequence is a nucleic acid sequence, polynucleotide or nucleotide sequence that is recombinantly expressed in a cell.

The terms "express" and "expression" mean allowing or causing the information in a gene or polynucleotide sequence to become manifest, for example producing a protein by activating the cellular functions involved in transcription and translation of a corresponding gene or DNA sequence. The expression product itself, e.g. the resulting protein, may also be said to be "expressed" by the cell. An expression product may be characterized as intracellular, extracellular or transmembrane. The term "intracellular" means inside a cell. The term "extracellular" means outside a cell. The term "transmembrane" means at least a portion of a polypeptide is embedded in a cell membrane. The term "cytoplasmic" means residing within the cell membrane, outside the nucleus.

The term "internal ribosome entry site" or "IRES," as used herein, refers to a nucleotide sequence that allows for translation initiation in the middle of a messenger RNA (mRNA) sequence as part of the greater process of protein synthesis.

The term "operably linked to," in the context of a regulatory nucleic acid sequence being "operably linked" to a heterologous nucleic acid sequence, means that the regulatory nucleic acid sequence is placed into a functional relationship with the heterologous nucleic acid sequence. In the context of an IRES, "operably linked to" refers to a functional linkage between a nucleic acid sequence containing an internal ribosome entry site and a heterologous coding sequence initiation in the middle of an mRNA sequence resulting in translation of the heterologous coding sequence.

The term "vector" means a vehicle by which a DNA or RNA sequence (e.g. a foreign gene) can be introduced into a genetically engineered cell, so as to transform the genetically engineered cell and promote expression (e.g. transcription and/or translation) of the introduced sequence. Vectors include viruses, plasmids, phages, etc.

The term "transduction" means the introduction of a foreign nucleic acid into a cell using a viral vector.

The term "isolated cell" means any cell of any organism that is removed from its natural environment. The term "isolated host cell" means any cell of any organism that is removed from its natural environment and selected, modified, transformed, grown, used or manipulated in any way, for the production of a substance by the cell, for example the expression by the cell of a gene, a DNA or RNA sequence, a protein or an enzyme. A "genetically engineered cell" means any cell of any organism that is modified, transformed, or manipulated by addition or modification of a gene, a DNA or RNA sequence, or protein or polypeptide. Isolated cells, host cells, and genetically engineered cells of the present invention include isolated immune cells, such as NK cells and T cells, that contain the DNA or RNA sequences encoding a chimeric receptor or chimeric receptor complex and express the chimeric receptor on the cell surface. Isolated host cells and genetically engineered cells may be used, for example, for enhancing an NK cell activity or a T lymphocyte activity, treatment of cancer, and treatment of infectious diseases.

To "expand," "specifically expand" or "preferentially expand" NK cells means to culture a mixed population of cells that contains a small number of NK cells so that the NK cells proliferate to numbers greater than other cell types in the population.

To "activate" Natural killer ("NK") cells and T cells means to induce a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

An "autologous cell" refers to a cell which was derived from the same individual that is being treated by cell therapy.

A "donor cell" refers to a cell that was derived from an individual other than the individual being treated by cell therapy.

An "allogeneic cell" refers to a genetically distinct cell.

As used herein, the terms "treat," "treating," and "treatment" in the context of the administration of a therapy to a subject refer to the beneficial effects that a subject derives from a therapy. In certain embodiments, treatment of a subject with a genetically engineered cell(s) described herein achieves one, two, three, four, or more of the following effects: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy.

As used herein, term "protecting against" in the context of administering a therapy to a subject refers to the prophylactic effect that a subject receives from a therapy. In a specific embodiment, this term refers to the inhibition of the development or onset of a disease or a symptom associated therewith, or inhibition of the recurrence of a disease or a symptom thereof.

As used herein, the terms "manage," "managing," and "management," in the context of the administration of a therapy to a subject, refer to the beneficial effects that a subject derives from a therapy, which does not result in a cure of a disease. In certain embodiments, a subject is administered one or more therapies to "manage" a disease or disorder so as to prevent the progression or worsening of symptoms associated with a disease.

As used herein, the term "in combination" refers to the use of more than one therapies (e.g., one or more prophylactic and/or therapeutic agents). The use of the term "in combination" does not restrict the order in which therapies are administered to a subject with a disease or disorder, or the route of administration. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder or a symptom thereof.

As used herein, the terms "subject" and "patient" are used interchangeably and refer to an animal. In a specific embodiment, such terms refer to a mammal such as a non-primate (e.g., cows, pigs, horses, cats, dogs, rats etc.) and a primate (e.g., monkey and human), most preferably a human.

As used herein, the term "premature human infant" refers to a human infant born at less than 37 weeks of gestational age.

As used herein, the term "human adult" refers to a human that is 18 years or older.

As used herein, the term "human child" refers to a human that is 1 year to 18 years old.

As used herein, the term "human infant" refers to a newborn to 1 year old human.

As used herein, the term "elderly human" refers to a human 65 years or older.

As used herein, the terms "disease" and "disorder" are used interchangeably to refer to a condition, in particular, a pathological condition.

As used herein, the term "significant," as in "significant" amount, change or effect, for example, means that the amount, change, or effect produced would not be likely to have occurred by random chance, as determined by any standard method for statistical analysis, such as a P test, wherein a P value less than the critical alpha level indicates that an event would be unlikely. Thus, a "significant" change in the context of this invention indicates the P value is less than the critical alpha level, and that the probability is small that the change happened by chance.

As used herein, the term "effective amount" in the context of the administration of a therapy to a subject refers to the amount of a therapy that achieves a desired prophylactic or therapeutic effect. Examples of effective amounts are provided in Section 5.6.2, infra.

All terms used herein, unless otherwise defined, will be given their ordinary technical or scientific meaning as would be commonly understood by one of ordinary skill in the art at the time of the present invention.

5.1 the Chimeric Receptor Complex

The chimeric receptor complex described herein comprises an extracellular receptor domain and one or more stimulatory molecules. Stimulation via the chimeric receptor complex enhances cytotoxicity and anti-tumor capacity against target cells, promotes signal transduction, triggers secretion of cytokines and/or chemokines, increases target cell apoptosis, and sustains cytotoxicity against target cells. As such, it is useful for treatment, protection against, and/or amelioration of cancer and infectious diseases.

The extracellular receptor domain may be derived from any one of the wide variety of well known receptors or secreted proteins associated with ligand binding and/or signal transduction. The receptor may be part of a protein which is monomeric, homodimeric, heterodimeric, or associated with a larger number of proteins in a non-covalent complex. In one embodiment, the receptor domain comprises an extracellular ligand-binding domain. In one embodiment, the extracellular domain comprises an NK cell-activating receptor. In a preferred embodiment, the extracellular domain will comprise the NK cell-activating Natural killer Group 2 member D (NKG2D) receptor.

The stimulatory molecule refers to a transmembrane stimulatory molecule and/or a cytoplasmic domain of a signaling protein. The stimulatory molecule may be a transmembrane protein, an adaptor protein, or a protein that recruits downstream signaling effector molecules. In one embodiment, a stimulatory molecule of the chimeric receptor complex may comprise a DNAX-activating protein 10 (DAP10) transmembrane protein. In another embodiment, the stimulatory molecule stabilizes the surface membrane expression of NKG2D. The cytoplasmic domain of the chimeric receptor complex comprises a signaling domain of a stimulatory protein. In particular, the cytoplasmic domain may comprise the CD3 zeta signaling domain by itself, or combined with any other desired cytoplasmic or other domain(s) useful in the context of this chimeric receptor complex. The extracellular ligand-binding domain, the cytoplasmic signaling domain, and transmembrane stimulatory molecule may be derived from any desired source for such domains and stimulatory molecules.

As used herein and unless otherwise specified, the term "NKG2D" and "Natural killer Group 2 member D" both refer to either a native NKG2D, a NKG2D derivative, or both. As used herein and unless otherwise specified, the term "CD3 zeta" refers to a native CD3 zeta, a CD3 zeta derivative, or both.

As used herein and unless otherwise specified, the term "DNAX-activating protein 10" and "DAP10" both refer to either a native DAP10, a DAP10 derivative, or both.

The term "native" in the context of proteins or polypeptides refer to any naturally occurring amino acid sequences, including immature or precursor and mature forms.

As used herein, the terms "derivative" in the context of proteins or polypeptides refer to: (a) a polypeptide that is at least 40%, 45%, 50%, 55%, 60%, 65%, 70%, 75%, 80%, 85%, 90%, 95%, 98% or 99% identical to a native polypeptide; (b) a polypeptide encoded by a nucleic acid sequence that is at least 40%, 45%, 50%, 55%, 60%, 65%, 70%, 75%, 80%, 85%, 90%, 95%, 98% or 99% identical a nucleic acid sequence encoding a native polypeptide; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to a native polypeptide; (d) a polypeptide encoded by nucleic acids can hybridize under high, moderate or typical stringency hybridization conditions to nucleic acids encoding a native polypeptide; (e) a polypeptide encoded by a nucleic acid sequence that can hybridize under high, moderate or typical stringency hybridization conditions to a nucleic acid sequence encoding a fragment of a native polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of a native polypeptide. Derivatives also include a polypeptide that comprises the amino acid sequence of a naturally occurring mature form of a mammalian polypeptide and a heterologous signal peptide amino acid sequence. In one embodiment, a derivative is isolated or purified. In specific embodiments, a derivative retains one or more functions of the native polypeptide from which it was derived. In a particular embodiment, an NKG2D derivative retains the ability to bind to a ligand of NKG2D and trigger signaling like the native NKG2D. In another embodiment, a CD3 zeta derivative retains the ability to trigger signaling like the native CD3 zeta. In another embodiment, a DAP10 derivative retains the ability to stabilize the surface membrane expression of NKG2D and trigger signaling like the native DAP10.

Percent identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wis.). Information regarding hybridization conditions (e.g., high, moderate, and typical stringency conditions) have been described, see, e.g., U.S. Patent Application Publication No. US 2005/0048549 (e.g., paragraphs 72-73).

5.2 Polynucleotides Encoding Chimeric Receptor Complex

In a preferred embodiment, the invention encompasses a polynucleotide encoding the NKG2D-DAP10-CD3zeta chimeric receptor complex, which comprises a nucleotide sequence encoding a CD3 zeta signaling domain (SEQ ID NO: 9), a nucleotide sequence encoding an extracellular ligand-binding domain comprising a NKG2D receptor (SEQ ID NO: 11), a nucleotide sequence comprising an internal ribosome entry site (IRES), and a nucleotide sequence encoding a DAP10 (SEQ ID NO: 13). The signaling domain of CD3 zeta and the extracellular ligand-binding domain comprising the NKG2D are expressed as a chimeric receptor protein. The IRES nucleotide sequence is placed upstream of the nucleotide sequence encoding DAP10 to drive translation of the DAP10 protein (SEQ ID NO: 14), which is expressed as a separate transmembrane stimulatory molecule.

The invention includes nucleotide sequences of fragments, variants (e.g., modified forms), derivatives, or functional equivalents of CD3 zeta, NKG2D and/or DAP10 proteins that retain the ability to enhance cytotoxicity and antitumor capacity against target cells, promote signal transduction, trigger secretion of cytokines and/or chemokines, increase target cell apoptosis, and sustain cytotoxicity against target cells. A "form of the protein" is intended to mean a protein that shares a significant homology with the proteins or antigen of interest and is capable of enhancing the cytotoxicity and antitumor activity against target cells. A "functionally equivalent" is understood within the scope of the present invention to refer to a nucleotide or polynucleotide which substantially shares at least one major functional property with the nucleotides or polynucleotides mentioned above. As such, these nucleotides are useful for treatment, protection against, and/or amelioration of cancer and infectious diseases.

Nucleic acid sequences encoding native CD3 zeta, NKG2D and DAP10 are known in the art and have been described in the literature. For example, the nucleic acid sequences encoding native CD3 zeta, NKG2D and DAP10 can be found in publicly available publications and databases, e.g., National Center for Biotechnology Information website at ncbi.nlm.nih.gov. Cloning techniques well known in the art can be used to generate nucleic acids encoding DAP10. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In specific embodiments, a polynucleotide encoding CD3 zeta comprises: (a) a nucleic acid sequence that is at least 40%, 45%, 50%, 55%, 60%, 65%, 70%, 75%, 80%, 85%, 90%, 95%, 98% or 99% identical to the naturally occurring nucleic acid sequence encoding a native CD3 zeta polypeptide; (b) a nucleic acid sequence encoding a polypeptide that is at least 40%, 45%, 50%, 55%, 60%, 65%, 70%, 75%, 80%, 85%, 90%, 95%, 98% or 99% identical the amino acid sequence of a native CD3 zeta polypeptide; (c) a nucleic acid sequence that contains 1, 2, 3, 4, 5, 6, 7, 8, 9, 10, 11, 12, 13, 14, 15, 16, 17, 18, 19, 20 or more nucleic acid base mutations (e.g., additions, deletions and/or substitutions) relative to the naturally occurring nucleic acid sequence encoding a native CD3 zeta polypeptide; (d) a nucleic acid sequence that hybridizes under high, moderate or typical stringency hybridization conditions to a naturally occurring nucleic acid sequence encoding a native CD3 zeta polypeptide; (e) a nucleic acid sequence that hybridizes under high, moderate or typical stringency hybridization conditions to a fragment of a naturally occurring nucleic acid sequence encoding a native CD3 zeta polypeptide; and (f) a nucleic acid sequence encoding a fragment of a naturally occurring nucleic acid sequence encoding a native CD3 zeta polypeptide. In another specific embodiment, the polynucleotide is an isolated or purified polynucleotide.

In specific embodiments, a polynucleotide encoding NKG2D comprises: (a) a nucleic acid sequence that is at least 40%, 45%, 50%, 55%, 60%, 65%, 70%, 75%, 80%, 85%, 90%, 95%, 98% or 99% identical to the naturally occurring nucleic acid sequence encoding a native NKG2D polypeptide; (b) a nucleic acid sequence encoding a polypeptide that is at least 40%, 45%, 50%, 55%, 60%, 65%, 70%, 75%, 80%, 85%, 90%, 95%, 98% or 99% identical the amino acid sequence of a native NKG2D polypeptide; (c) a nucleic acid sequence that contains 1, 2, 3, 4, 5, 6, 7, 8, 9, 10, 11, 12, 13, 14, 15, 16, 17, 18, 19, 20 or more nucleic acid base mutations (e.g., additions, deletions and/or substitutions) relative to the naturally occurring nucleic acid sequence encoding a native NKG2D polypeptide; (d) a nucleic acid sequence that hybridizes under high, moderate or typical stringency hybridization conditions to a naturally occurring nucleic acid sequence encoding a native NKG2D polypeptide; (e) a nucleic acid sequence that hybridizes under high, moderate or typical stringency hybridization conditions to a fragment of a naturally occurring nucleic acid sequence encoding a native NKG2D polypeptide; and (f) a nucleic acid sequence encoding a fragment of a naturally occurring nucleic acid sequence encoding a native NKG2D polypeptide. In another specific embodiment, the polynucleotide is an isolated or purified polynucleotide.

In specific embodiments, a polynucleotide encoding DAP10 comprises: (a) a nucleic acid sequence that is at least 40%, 45%, 50%, 55%, 60%, 65%, 70%, 75%, 80%, 85%, 90%, 95%, 98% or 99% identical to the naturally occurring nucleic acid sequence encoding a native DAP10 polypeptide; (b) a nucleic acid sequence encoding a polypeptide that is at least 40%, 45%, 50%, 55%, 60%, 65%, 70%, 75%, 80%, 85%, 90%, 95%, 98% or 99% identical the amino acid sequence of a native DAP10 polypeptide; (c) a nucleic acid sequence that contains 1, 2, 3, 4, 5, 6, 7, 8, 9, 10, 11, 12, 13, 14, 15, 16, 17, 18, 19, 20 or more nucleic acid base mutations (e.g., additions, deletions and/or substitutions) relative to the naturally occurring nucleic acid sequence encoding a native DAP10 polypeptide; (d) a nucleic acid sequence that hybridizes under high, moderate or typical stringency hybridization conditions to a naturally occurring nucleic acid sequence encoding a native DAP10 polypeptide; (e) a nucleic acid sequence that hybridizes under high, moderate or typical stringency hybridization conditions to a fragment of a naturally occurring nucleic acid sequence encoding a native DAP10 polypeptide; and (f) a nucleic acid sequence encoding a fragment of a naturally occurring nucleic acid sequence encoding a native DAP10 polypeptide. In another specific embodiment, the polynucleotide is an isolated or purified polynucleotide.

In a specific embodiment, a nucleic acid sequence encoding a CD3 zeta polypeptide is a derivative of a naturally occurring nucleic acid sequence encoding a native human CD3 zeta polypeptide. In another embodiment, a nucleic acid sequence encoding a CD3 zeta polypeptide is a derivative of a naturally occurring nucleic acid sequence encoding an immature or precursor form of a native human CD3 zeta polypeptide. In another embodiment, a nucleic acid sequence encoding a CD3 zeta polypeptide is a derivative of a naturally occurring nucleic acid sequence encoding a mature form of a native human CD3 zeta polypeptide. In another embodiment, a nucleic acid sequence encodes a CD3 zeta derivative described herein.

In a specific embodiment, a nucleic acid sequence encoding a NKG2D polypeptide is a derivative of a naturally occurring nucleic acid sequence encoding a native human NKG2D polypeptide. In another embodiment, a nucleic acid sequence encoding a NKG2D polypeptide is a derivative of a naturally occurring nucleic acid sequence encoding an immature or precursor form of a native human NKG2D polypeptide. In another embodiment, a nucleic acid sequence encoding a NKG2D polypeptide is a derivative of a naturally occurring nucleic acid sequence encoding a mature form of a native human NKG2D polypeptide. In another embodiment, a nucleic acid sequence encodes a NKG2D derivative described herein.

In a specific embodiment, a nucleic acid sequence encoding a DAP10 polypeptide is a derivative of a naturally occurring nucleic acid sequence encoding a native human DAP10 polypeptide. In another embodiment, a nucleic acid sequence encoding a DAP10 polypeptide is a derivative of a naturally occurring nucleic acid sequence encoding an immature or precursor form of a native human DAP10 polypeptide. In another embodiment, a nucleic acid sequence encoding a DAP10 polypeptide is a derivative of a naturally occurring nucleic acid sequence encoding a mature form of a native human DAP10 polypeptide. In another embodiment, a nucleic acid sequence encodes a DAP10 derivative described herein.

In certain embodiments, polynucleotides include codon-optimized nucleic acid sequences that encode native CD3 zeta polypeptides, NKG2D polypeptides, or DAP10 polypeptides, including mature and immature forms. In other embodiments, polynucleotides include nucleic acids that encode CD3 zeta, NKG2D, or DAP10 RNA transcripts containing mutations that eliminate potential splice sites and instability elements (e.g., A/T or A/U rich elements) without affecting the amino acid sequence to increase the stability of the CD3 zeta RNA transcripts.

In certain embodiments, nucleic acid sequences encode a NKG2D polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of a function of a native NKG2D polypeptide, such as enhancing cytotoxicity and anti-tumor capacity against target cells, promoting signal transduction, increasing cytokine and/or chemokine secretion, increasing target cell apoptosis, or sustaining cytotoxicity against target cells, for example, as measured by assays well known in the art.

In certain embodiments, nucleic acid sequences encode a CD3 zeta polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of a function of a native CD3 zeta polypeptide, such as enhancing cytotoxicity and anti-tumor capacity against target cells, promoting signal transduction, increasing cytokine and/or chemokine secretion, increasing target cell apoptosis, or sustaining cytotoxicity against target cells, for example, as measured by assays well known in the art.

In certain embodiments, nucleic acid sequences encode a DAP10 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of a function of a native DAP10 polypeptide, such as enhancing cytotoxicity and anti-tumor capacity against target cells, promoting signal transduction, increasing cytokine and/or chemokine secretion, increasing target cell apoptosis, sustaining cytotoxicity against target cells, or stabilizing the surface membrane expression of NKG2D, for example, as measured by assays well known in the art.

In some embodiments, nucleic acid sequences encode a NKG2D polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of NKG2D (NKG2DL) binds to a native NKG2D polypeptide, as measured by assays well-known in the art. Non-limiting examples of ligands of human NKG2D include MICA, MICB, ULBP1, ULBP2, ULBP3, ULBP4, ULBP5 and ULBP6 and others that are well known in the art. The one or more signal transduction pathways induced by binding of a NKG2DL to NKG2D can be measured by, e.g., assessing the activation of a signal transduction moiety (e.g., the phosphorylation of CREB1, TBK1, ACK1, Tyk2, CdC25c, PRK2, MEKK2, EGFR, CDK4, Tyk2, Abl, Ksr1, MLK3, CD1K, MAPKAPK2, JAK2, c-IAP1, MST1, Calnexin, PKA R2a, PKA Cb, JNK3, Hsp90ab, ILK1, PDGFRa/b, PDGFRb, IRAK2, p107, PKCd, Paxillin 1, PI4KCB, PKCb1, STAT2, PKCb1/2, PKCb2, or p35+p25), and chemokine production/secretion and cytokine production/secretion (e.g., GM-CSF, IFN-γ, IL-2, IL-13, MIP-1α, MIP-1β, Rantes, TNF-α, Eotaxin, FGF-2, Flt-3L, Fractalkine, GRO, IFN-α2, IL-1rα, IL-5, IL-8, MCP-1, PDGF-AA, TNF-β, VEGF, sCD40L, CCL5, EGF, G-CSF, IL-10, IL-12p40, IL-12p70, IL-15, IL-17, IL-1α, IL-1β, IL-3, IL-4, IL-6, IL-7, IL-9, IP-10, MCP-3, MDC, or PDGF-BB) using techniques such as antibody microarray, ELISAs, Western blots, electromobility shift assays, and other immunoassays. In a specific embodiment, nucleic acid sequences encode a NKG2D polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by binding of a native NKG2DL to NKG2D.

In some embodiments, nucleic acid sequences encode a DAP10 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to stabilize the surface membrane expression of NKG2D and activate or induce one or more of the signal transduction pathways induced when a native ligand of NKG2D (NKG2DL) binds to a native NKG2D polypeptide, as measured by assays well-known in the art. Non-limiting exemplary ligands of human NKG2D include MICA, MICB, ULBP1, ULBP2, ULBP3, ULBP4, ULBP5 and ULBP6 and others that are well known in the art. The one or more signal transduction pathways induced by binding of a NKG2DL to NKG2D can be measured by, e.g., assessing the activation of a signal transduction moiety (e.g., the phosphorylation of CREB1, TBK1, ACK1, Tyk2, CdC25c, PRK2, MEKK2, EGFR, CDK4, Tyk2, Abl, Ksr1, MLK3, CD1K, MAPKAPK2, JAK2, c-IAP1, MST1, Calnexin, PKA R2a, PKA Cb, JNK3, Hsp90ab, ILK1, PDGFRa/b, PDGFRb, IRAK2, p107, PKCd, Paxillin 1, PI4KCB, PKCb1, STAT2, PKCb1/2, PKCb2, or p35+p25), and chemokine production/secretion and cytokine production/secretion (e.g., GM-CSF, IFN-γ, IL-2, IL-13, MIP-1α, MIP-1β, Rantes, TNF-α, Eotaxin, FGF-2, Flt-3L, Fractalkine, GRO, IFN-α2, IL-1rα, IL-5, IL-8, MCP-1, PDGF-AA, TNF-β, VEGF, sCD40L, CCL5, EGF, G-CSF, IL-10, IL-12p40, IL-12p70, IL-15, IL-17, IL-1α, IL-1β, IL-3, IL-4, IL-6, IL-7, IL-9, IP-10, MCP-3, MDC, or PDGF-BB) using techniques such as antibody microarray, ELISAs, Western blots, electromobility shift assays, and other immunoassays. In a specific embodiment, nucleic acid sequences encode a DAP10 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by binding of a native NKG2DL to NKG2D.

In some embodiments, nucleic acid sequences encode a CD3 zeta polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of NKG2D (NKG2DL) binds to a native NKG2D polypeptide, as measured by assays well-known in the art. Non-limiting exemplary ligands of human NKG2D include MICA, MICB, ULBP1, ULBP2, ULBP3, ULBP4, ULBP5 and ULBP6 and others that are well known in the art. The one or more signal transduction pathways induced by binding of a NKG2DL to NKG2D can be measured by, e.g., assessing the activation of a signal transduction moiety (e.g., the phosphorylation of CREB1, TBK1, ACK1, Tyk2, CdC25c, PRK2, MEKK2, EGFR, CDK4, Tyk2, Abl, Ksr1, MLK3, CD1K, MAPKAPK2, JAK2, c-IAP1, MST1, Calnexin, PKA R2a, PKA Cb, JNK3, Hsp90ab, ILK1, PDGFRa/b, PDGFRb, IRAK2, p107, PKCd, Paxillin 1, PI4KCB, PKCb1, STAT2, PKCb1/2, PKCb2, or p35+p25), and chemokine production/secretion and cytokine production/secretion (e.g., GM-CSF, IFN-γ, IL-2, IL-13, MIP-1α, MIP-1β, Rantes, TNF-α, Eotaxin, FGF-2, Flt-3L, Fractalkine, GRO, IFN-α2, IL-1rα, IL-5, IL-8, MCP-1, PDGF-AA, TNF-β, VEGF, sCD40L, CCL5, EGF, G-CSF, IL-10, IL-12p40, IL-12p70, IL-15, IL-17, IL-1α, IL-1β, IL-3, IL-4, IL-6, IL-7, IL-9, IP-10, MCP-3, MDC, or PDGF-BB) using techniques such as antibody microarray, ELISAs, Western blots, electromobility shift assays, and other immunoassays. In a specific embodiment, nucleic acid sequences encode a CD3 zeta polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by binding of a native NKG2DL to NKG2D.

In certain embodiments, nucleic acid sequences encode an NKG2D extracellular domain polypeptide that has a higher affinity for a native ligand of NKG2D than a native NKG2D extracellular domain polypeptide for the same ligand, as measured by assays/techniques well known in the art, e.g., ELISA, Biacore, or co-immunoprecipitation. In a specific embodiment, nucleic acid sequences encode an NKG2D extracellular domain polypeptide that binds to a native ligand of NKG2D with 0.5 logs, 1 log, 1.5 logs, 2 logs, 2.5 logs, or 3 logs higher affinity than a native NKG2D extracellular domain polypeptide binds to the same receptor, as measured by assays/techniques well known in the art, e.g., ELISA, Biacore, or co-immunoprecipitation.

5.3 Constructs and Recombinant Expression 5.3.1 Vectors

The polynucleotides encoding a chimeric receptor complex described herein can be inserted into a vector for expression in mammalian cells.

A vector may comprise one or more regulatory sequences, selected on the basis of the cells to be used for expression, which is operably linked to the polynucleotide to be expressed. Regulatory sequences include promoters, enhancers and other expression control elements (e.g., polyadenylation signals). In a specific embodiment, a vector may comprise one or more transcriptional regulatory element(s) operably linked to the coding sequence of a protein. The transcriptional regulatory elements are typically 5' to the coding sequence and direct the transcription of the polynucleotide encoding a chimeric receptor complex described herein. In some embodiments, one or more of the transcriptional regulatory elements that are found in nature to regulate the transcription of the NKG2D, CD3 zeta, or DAP10 are used to control transcription. In other embodiments, one or more transcriptional regulatory elements that are heterologous to the NKG2D, CD3 zeta or DAP10 are used to control transcription. Any transcriptional regulatory element(s) known to one of skill in the art may be used. Non-limiting examples of the types of transcriptional regulatory element(s) include a constitutive promoter, a tissue-specific promoter, and an inducible promoter. In a specific embodiment, transcription is controlled, at least in part, by a mammalian (in some embodiments, human) transcriptional regulatory element(s). In a specific embodiment, transcription is controlled, at least in part, by a strong promoter, e.g., CMV.

Specific examples of promoters which may be used to control transcription include, but are not limited to, the SV40 early promoter region (Bernoist & Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); adenovirus (ADV), cytomegalovirus (CMV), bovine papilloma virus (BPV), parovirus B19p6 promoter, prokaryotic expression vectors such as the beta-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378). In other aspects, an inducible promoter can be used.

A vector also may comprise one or more post-transcriptional regulatory element(s) operably linked to the coding sequence of a protein. The post-transcriptional regulatory elements can be 5' and/or 3' to the coding sequence and direct the post-transcriptional regulation of the translation of RNA transcripts encoding a protein.

The vector chosen will depend upon a variety of factors, including, without limitation, the strength of the transcriptional regulatory elements and the cell to be used to express a protein. The vector can be a plasmid, phagemid, cosmid, viral vector, phage, artificial chromosome, and the like. In one aspect, the vectors can be episomal, non-homologously, or homologously integrating vectors, which can be introduced into the appropriate cells by any suitable means (transformation, transfection, conjugation, protoplast fusion, electroporation, calcium phosphate-precipitation, direct microinjection, etc.) to transform them.

In a preferred embodiment, the vector is a viral vector, e.g., retroviruses, lentiviruses, vaccinia virus, adenovirus, etc.). Non-limiting examples of other cell-vector systems that may be used to express a protein include mammalian cell systems infected with virus and stable cell lines generated by transformation using a selectable marker. In some embodiments, a vector includes a selectable marker gene including, but not limited to, neo, gpt, dhfr, ada, pac, hyg, CAD and hisD. In a specific preferred embodiment, the viral vector is the vector pMSCV described infra, or is a vector similar to pMSCV. The vector can be a plasmid or a stable integration vector for transient or stable expression of a protein in cells. For stable expression, the vector can mediate chromosomal integration at a target site or a random chromosomal site.

A vector or plasmid comprising a polynucleotide comprising a nucleotide sequence encoding a chimeric receptor complex described herein may be transduced or transfected into NK cells or T cells in culture and readministered or re-introduced in vivo into a patient. In certain aspects, a vector comprising a polynucleotide comprising a nucleotide sequence encoding a chimeric receptor complex described herein is administered to a mammal for recombinant expression of a protein in vivo. In other aspects, cells transfected with a vector are transplanted or implanted in a subject.

In another embodiment, a polynucleotide comprising a nucleotide sequence encoding a chimeric receptor complex described herein may be introduced into NK or T cells by electroporation and re-introduced in vivo into a patient. Electroporation methods are well known in the art. Any method for electroporation method that permits rapid expression of the chimeric receptor complex in a large number of cells is described herein. In a preferred embodiment, electroporation of mRNA will result in highly efficient expression of the functional chimeric receptor complex in expanded cells. In another preferred embodiment, one or more mRNAs encoding the component of the chimeric receptor complex described herein is electroporated into expanded cells for expression of the chimeric receptor or the chimeric receptor complex in vivo. In another preferred embodiment, electroporation results in increase of expression of the chimeric receptor or the chimeric receptor complex in vivo. In another embodiment, cells electroporated with mRNA encoding the components of the chimeric receptor markedly enhances cytotoxicity and anti-tumor capacity against target cells. In yet another preferred embodiment, this method is adapted to a clinical-grade protocol for genetic engineering of large numbers of cells to treat a wide range of cancers and infectious diseases.

Techniques for practicing aspects of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

5.3.2 Genetically Engineered Cells

Cells can be engineered to express the chimeric receptor complex encoded by the polynucleotides or a vector described herein. Non-limiting examples of cells that can be used to express the chimeric receptor complex encoded by the polynucleotides or vectors described herein include mammalian cells, primary cells, and immortalized cells. In one embodiment, the cells are mammalian lymphocytes (in a particular embodiment, human lymphocytes). In a specific embodiment, the cells are mammalian NK cells or T cells, particularly CD8 T cells (both $\alpha\beta$ and $\gamma\delta$). In another specific embodiment, the cells are human NK cells and/or human T cells. In another embodiment, the cells are cells derived from a subject. The cells may be autologous to the individual being treated, or allogenic cells. In one embodiment the cells are cells derived from a donor. In another embodiment, the cells are derived from the patient being treated. In another embodiment, the cells are NK cells and/or T cells derived from a subject that have been activated. In another embodiment, the cells are NK cells and/or T cells derived from a subject that have been activated and expanded.

NK cells and T cells may be activated and expanded prior to, or after, genetic modification of the NK cells or T cells to express a chimeric receptor complex. Techniques for activating as well as expanding the T cells are well known in the art and generally available. See, e.g., the methods described in the Examples, infra, and U.S. Pat. Nos. 7,435,596 and 8,026,097, which are incorporated herein by reference, for techniques for activating and expanding NK cells. Alternate methods include, but are not limited to, those found in U.S. Pat. Nos. 8,257,970; 7,572,631; 7,175,843; 7,232, 566; 7,172,869; 7,144,575; 7,172,869; 7,067,318; 6,905,680; 6,905,681; 6,905,874; 6,887,466; 6,867,041; 6,797,514; 6,692,964; 6,534,055; 6,352,694; 5,883,223; and 5,858,358, for example.

In a specific embodiment, reference to a cell transfected with a polynucleotide includes the particular subject cell transfected with the polynucleotide and the progeny or potential progeny of such a cell. Progeny of such a cell may not be identical to the parent cell transfected with the polynucleotide due to mutations or environmental influences that may occur in succeeding generations or integration of the polynucleotide into the cell genome.

In some embodiments, isolated cells are utilized herein. In a specific embodiment, the isolated cells are at least 80%, 90%, 95% or 98% free of a different cell type as measured by a technique known to one of skill in the art, such as flow cytometry. In other words, at least 80%, 90%, 95% or 98% of the isolated cells are of the same cell type.

Any techniques known to one of skill in the art can be used to transfect or transduce cells with nucleic acids including, e.g., transformation, transfection, conjugation, protoplast fusion, electroporation, calcium phosphate-precipitation, direct microinjection, and infection with viruses, including but not limited to adenoviruses, lentiviruses, and retroviruses. In one embodiment, the cells are transiently transfected with a polynucleotide described herein. In another embodiment, the cells are stably transfected with a polynucleotide described herein.

In certain embodiments, cells engineered to express a chimeric receptor complex described herein are introduced, re-introduced, administered, or implanted or transplanted into a subject to treat or manage or protect against a disease.

5.4 Pharmaceutical Compositions

Presented herein are compositions comprising a polynucleotide encoding a chimeric receptor complex of the invention. Also presented herein are compositions comprising cells (in particular, NK cells and/or T cells) comprising a polynucleotide encoding a chimeric receptor complex of the invention. In one embodiment, the compositions comprise an effective amount of a polynucleotide comprising a nucleotide sequence encoding a chimeric receptor complex described herein, and a pharmaceutically acceptable carrier. In specific embodiments, a pharmaceutical composition comprises an amount of a polynucleotide comprising a nucleotide sequence encoding a chimeric receptor complex described herein that is effective to achieve the desired effect. In another embodiment, the compositions comprise an effective amount of cells (in particular, NK cells and/or T cells) comprising a polynucleotide comprising a nucleotide sequence encoding a chimeric receptor complex described herein, and a pharmaceutically acceptable carrier. In specific embodiments, a pharmaceutical composition comprises an amount of cells (in particular, NK cells and/or T cells) comprising a polynucleotide comprising a nucleotide sequence encoding a chimeric receptor complex described herein that is effective to achieve the desired effect.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the genetically engineered cell(s) is administered. Such pharmaceutical carriers can be sterile liquids, such as saline solutions.

Pharmaceutical compositions for use in accordance with the methods described herein may be formulated in any conventional manner using one or more pharmaceutically acceptable carriers or excipients.

In some embodiments, cells (in particular, NK cells and/or T cells) comprising a polynucleotide comprising a nucleotide sequence encoding a chimeric receptor complex described herein may be formulated for administration by any method known to one of skill in the art, including but not limited to, intradermal, parenteral, transdermal, intraparenteral, intratumoral, and administration.

In a specific embodiment, cells (in particular, NK cells and/or T cells) comprising a polynucleotide comprising a nucleotide sequence encoding a chimeric receptor complex described herein are formulated for local or systemic parenteral administration.

The cells (in particular, NK cells and/or T cells) comprising a polynucleotide comprising a nucleotide sequence encoding a chimeric receptor complex described herein can be formulated for parenteral administration by injection, e.g., by bolus injection or continuous infusion.

In addition, cells (in particular, NK cells and/or T cells) comprising a polynucleotide comprising a nucleotide sequence encoding a chimeric receptor complex described herein may also be formulated for implantation (for example subcutaneously or intramuscularly) or by intramuscular injection.

5.5 Therapeutic Methods

In one aspect, presented herein are methods for enhancing cytoxicity, anti-tumor, or cytokine/chemokine secretion in a subject, comprising administering to a subject in need thereof a cell genetically engineered for expression of the chimeric antigen receptor complex, or a composition thereof. In a specific embodiment, presented herein are methods for treating, protecting against and/or managing diseases in which it is desirable to activate or enhance one or more immune functions or responses, comprising administering to a subject in need thereof a cell genetically engineered for expression of the chimeric antigen receptor complex, or a composition thereof. In certain embodiments, the genetically engineered cells described herein that are administered to the subject are autologous cells. In other embodiments, the genetically engineered cells described herein that are administered to the subject are donor cells.

Non-limiting examples of diseases that can be treated, protected against, or managed by an enhancement of immune function include, but are not limited to, cancer and infectious diseases. Various cancers and infectious diseases are described below.

In a specific embodiment, a genetically engineered cell described herein or a composition thereof activates or enhances or induces one or more immune functions or responses in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the genetically cell(s) described herein or a composition thereof using assays well known in the art, e.g., ELISPOT, ELISA, and cell proliferation assays. In a specific embodiment, the immune function is cytokine release (e.g., interferon-gamma, IL-2, IL-5, IL-10, IL-12, or transforming growth factor (TGF)—beta). In one embodiment, the immune function is NK cell proliferation, which can be assayed, e.g., by flow cytometry to detect the number of cells expressing markers of NK cells (e.g., CD56). In one embodiment, the immune function is T cell proliferation, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is an effector function which can be assayed, e.g., by a cytotoxicity assay or other assays well known in the art. In one embodiment, the immune function does not exhibit a significant increase in cytotoxicity against normal cells (e.g., non-transformed peripheral blood lymphocytes, bone marrow-derived mesenchymal cells, uninfected cells, or non-tumor cells), e.g., the increase in cytotoxicity in the patient against normal cells (non-tumor or uninfected cells) could be accountable by chance, as determined by a standard statistical analysis method.

5.5.1 Methods for Treating, Protecting Against, and Managing Cancer

In a specific aspect, presented herein are methods for treating, protecting against, and/or managing cancer, comprising administering to a subject in need thereof an effective amount of a genetically engineered cell(s) described herein or a composition thereof. In a specific embodiment, a genetically engineered cell(s) described herein or a composition thereof is the only active agent administered to a subject. In certain embodiments, the genetically engineered cells described herein that are administered to the subject are autologous cells. In other embodiments, the genetically engineered cells described herein that are administered to the subject are donor cells.

The effect of a genetically engineered cell(s) described herein on proliferation of cancer cells can be detected by routine assays, such as by assays that measure the uptake of radiolabeled thymidine. Alternatively, cell viability can be measured by assays that measure lactate dehydrogenase (LDH), a stable cytosolic enzyme that is released upon cell lysis, or by the release of [$^{51}$Cr] upon cell lysis. In one embodiment, necrosis measured by the ability or inability of a cell to take up a dye such as neutral red, trypan blue, or ALAMAR™ blue (Page et al., 1993, Intl. J. of Oncology 3:473 476). In such an assay, the cells are incubated in media containing the dye, the cells are washed, and the remaining dye, reflecting cellular uptake of the dye, is measured spectrophotometrically.

In another embodiment, the dye is sulforhodamine B (SRB), whose binding to proteins can be used as a measure of cytotoxicity (Skehan et al., 1990, J. Nat'l Cancer Inst. 82:1107 12). In yet another embodiment, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55 63).

In other embodiments, apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature (see, e.g., Piazza et al., 1995, Cancer Research 55:3110 16). Features of this method include collecting both floating and attached cells, identification of the optimal treatment times and dose range for observing apoptosis, and identification of optimal cell culture conditions.

In another embodiment, apoptosis is quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34 37 (Roche Molecular Biochemicals). In yet another embodiment, apoptosis can be observed morphologically.

Cancer cell lines on which such assays can be performed are well known to those of skill in the art. Apoptosis, necrosis and proliferation assays can also be performed on primary cells, e.g., a tissue explant.

In a specific embodiment, the proliferation or viability of cancer cells contacted with a genetically engineered cell(s) described herein or a composition comprising a genetically engineered cell(s) described herein is inhibited or reduced by at least 2 fold, preferably at least 2.5 fold, at least 3 fold, at least 4 fold, at least 5 fold, at least 7 fold, or at least 10 fold relative to the proliferation of the cancer cells when contacted with a negative control as measured using assays well known in the art, e.g., cell proliferation assays using CSFE, BrdU, and $^3$H-Thymidine incorporation. In another embodiment, the proliferation of cancer cells contacted with a genetically engineered cell(s) described herein is inhibited or reduced by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to cancer cells contacted with a negative control as measured using assays well known in the art, e.g., cell proliferation assays using CSFE, BrdU, and $^3$H-Thymidine incorporation, or those assays described above.

In specific embodiments, the administration of a genetically engineered cell(s) described herein or a composition thereof to a subject with cancer (in some embodiments, an animal model for cancer) achieves at least one, two, three, four or more of the following effects: (i) the reduction or amelioration of the severity of one or more symptoms of cancer; (ii) the reduction in the duration of one or more symptoms associated with cancer; (iii) the protection against the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) an increase in the survival rate of patients; (xiii) a decrease in hospitalization rate; (ix) the protection against the development or onset of one or more symptoms associated with cancer; (x) the reduction in the number of symptoms associated with cancer; (xi) an increase in symptom-free survival of cancer patients; (xii) improvement in quality of life as assessed by methods well known in the art; (xiii) the protection against the recurrence of a tumor; (xiv) the regression of tumors and/or one or more symptoms associated therewith; (xvii) the inhibition of the progression of tumors and/or one or more symptoms associated therewith; (xviii) a reduction in the growth of a tumor; (xix) a decrease in tumor size (e.g., volume or diameter); (xx) a reduction in the formation of a newly formed tumor; (xxi) eradication, removal, or control of primary, regional and/or metastatic tumors; (xxii) a decrease in the number or size of metastases; (xxiii) a reduction in mortality; (xxiv) an increase in the tumor-free survival rate of patients; (xxv) an increase in relapse free survival; (xxvi) an increase in the number of patients in remission; (xxvii) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxviii) an increase in the length of remission in patients.

In a specific embodiment, the administration of a genetically engineered cell(s) described herein or a composition thereof to a subject with cancer (in some embodiments, an animal model for cancer) inhibits or reduces the growth of a tumor by at least 2 fold, preferably at least 2.5 fold, at least 3 fold, at least 4 fold, at least 5 fold, at least 7 fold, or at least 10 fold relative to the growth of a tumor in a subject with cancer (in some embodiments, in the same animal model for cancer) administered a negative control as measured using assays well known in the art. In another embodiment, the administration of a genetically engineered cell(s) described herein or a composition comprising a genetically engineered cell(s) described herein to a subject with cancer (in some embodiments, an animal model for cancer) inhibits or reduces the growth of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to the growth of a tumor in a subject with cancer (in some embodiments, in the same animal model for cancer) administered a negative control as measured using assays well known in the art.

In a specific embodiment, the administration of a genetically engineered cell(s) described herein or a composition comprising a genetically engineered cell(s) described herein to a subject with cancer (in some embodiments, an animal model for cancer) reduces the size of a tumor by at least 2 fold, preferably at least 2.5 fold, at least 3 fold, at least 4 fold, at least 5 fold, at least 7 fold, or at least 10 fold relative to the growth of a tumor in a subject with cancer (in some embodiments, the same animal model for cancer) administered a negative control as measured using assays well known in the art. In another embodiment, the administration of a genetically engineered cell(s) described herein or a composition comprising a genetically engineered cell(s) described herein to a subject with (in some embodiments, an animal model for cancer) reduces the size of a tumor by at least 10%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, or 10% to 25%, 25% to 50%, 25% to 75%, 50% to 75%, 75% to 100% relative to the growth of a tumor in a subject with cancer (in some embodiments, the same animal model for cancer) administered a negative control as measured using assays well known in the art.

In some embodiments, a genetically engineered cell(s) described herein is administered to a subject in combination with one or more other therapies, e.g., anti-cancer agents, cytokines, cellular vaccines or anti-hormonal agents, to treat and/or manage cancer. In one embodiment, the combination of a genetically engineered cell(s) described herein and one or more other therapies provides an additive therapeutic effect relative to the therapeutic effects of the genetically engineered cell(s) described herein alone or the one or more other therapies alone. In one embodiment, the combination of a genetically engineered cell(s) described herein and one or more other therapies provides more than an additive therapeutic effect relative to the therapeutic effects of the genetically engineered cell(s) described herein alone or the one or more other therapies alone. In one embodiment, the combination of a genetically engineered cell(s) described herein and one or more other therapies provides a synergistic therapeutic effect relative to the therapeutic effects of the genetically engineered cell(s) described herein alone or the one or more other therapies alone.

In a specific embodiment, a genetically engineered cell(s) described herein is administered in combination with radiation therapy comprising, e.g., the use of x-rays, gamma rays and other sources of radiation to destroy the cancer cells. In specific embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass. In one aspect, the genetically engineered cell(s) described herein can activate or enhance the immune function of cancer patient with a compromised immune system due to anti-cancer therapy. In another embodiment, a genetically engineered cell(s) described herein is administered in combination with chemotherapy. In an embodiment, a genetically engineered cell(s) described herein can be used before, during or after radiation therapy or chemotherapy. In another embodiment, a genetically engineered cell(s) described herein can be used before, during or after surgery.

5.5.1.1 Types of Cancers

Cancers and related disorders that can be treated, protected against, or managed in accordance with the methods described herein include, but are not limited to, the following: Leukemias including, but not limited to, acute leukemia, acute lymphocytic leukemia, acute myelocytic Leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, and chronic lymphocytic leukemia, hairy cell leukemia; polycythemia vera; lymphomas such as but not limited to Hodgkin's disease, and non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma; gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, semi noma, anaplastic, spermatocytic, nonseminoma, embryonal carcinoma, teratoma carcinoma, choriocarcinoma (yolk-sac tumor); prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, and superficial spreading melanoma, nodular melanoma, lentigo malignant melanoma, acral lentiginous melanoma; kidney cancers including but not limited to, renal cell cancer, renal cancer, adenocarcinoma, hypernephroma, fibrosarcoma, and transitional cell cancer (renal pelvis and/or uterer); Wilms' tumor; bladder cancers including but not limited to, transitional cell carcinoma, squamous cell cancer, adenocarcinoma, and carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In one embodiment, the cancer is benign, e.g., polyps and benign lesions. In other embodiments, the cancer is metastatic. The genetically engineered cell(s) can be used in the treatment of pre-malignant as well as malignant conditions. Pre-malignant conditions include hyperplasia, metaplasia, and dysplasia. Treatment of malignant conditions includes the treatment of primary as well as metastatic tumors. In a specific embodiment the cancer is melanoma, colon cancer, lung cancer, breast cancer, prostate cancer, cervical cancer, brain cancer, pancreatic cancer, or renal cancer, T-cell acute lymphocytic leukemia (ALL), a B-cell acute lymphocytic leukemia, a lymphoblastic leukemia, a B-cell chronic lymphocytic leukemia or a B-cell non-Hodgkin's lymphoma, rhabdomyosarcoma, neuroblastoma, Ewing sarcoma, gastric cancer, hepatoma.

5.5.1.2 Patient Populations

In some embodiments, a genetically engineered cell(s) described herein, compositions comprising a genetically engineered cell(s) described herein, or combination therapies are administered to a subject suffering from or diagnosed with cancer. In other embodiments, a genetically engineered cell(s) described herein, compositions comprising a genetically engineered cell(s) described herein, or combination therapies are administered to a subject predisposed or susceptible to developing cancer. In some embodiments, a genetically engineered cell(s) described herein, compositions comprising a genetically engineered cell(s) described herein, or combination therapies are administered to a subject that lives in a region where there is a high occurrence rate of cancer. In a specific embodiment, the cancer is characterized by a pre-malignant tumor or a malignant tumor.

In some embodiments, a genetically engineered cell(s) described herein, composition comprising a genetically engineered cell(s) described herein, or a combination therapy is administered to a mammal. In certain embodiments, a genetically engineered cell(s) described herein, composition comprising a genetically engineered cell(s) described herein, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a genetically engineered cell(s) described herein, composition comprising a genetically engineered cell(s) described herein, or a combination therapy is administered to a pet, e.g., a dog or cat. In certain embodiments, a genetically engineered cell(s) described herein, composition comprising a genetically engineered cell(s) described herein, or a combination therapy is administered to a farm animal or livestock, e.g., pig, cows, horses, chickens, etc.

In certain embodiments, a genetically engineered cell(s) described herein, composition comprising a genetically engineered cell(s) described herein, or a combination therapy is administered to a human at risk developing cancer. In certain embodiments, a genetically engineered cell(s) described herein, composition comprising a genetically engineered cell(s) described herein, or a combination therapy is administered to a human with cancer. In certain embodiments, a genetically engineered cell(s) described herein, composition comprising a genetically engineered cell(s) described herein, or a combination therapy is administered to a human diagnosed with cancer. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a genetically engineered cell(s) described herein, composition comprising a genetically engineered cell(s) described herein, or a combination therapy is administered to a human infant or a premature human infant. In other embodiments, a genetically engineered cell(s) described herein, composition comprising a genetically engineered cell(s) described herein, or a combination therapy is administered to a human child. In other embodiments, a genetically engineered cell(s) described herein, composition comprising a genetically engineered cell(s) described herein, or a combination therapy is administered to a human adult. In yet other embodiments, a genetically engineered cell(s) described herein, composition comprising a genetically engineered cell(s) described herein, or a combination therapy is administered to an elderly human.

In certain embodiments, a genetically engineered cell(s) described herein, composition comprising a genetically engineered cell(s) described herein, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a genetically engineered cell(s) described herein, composition comprising a genetically engineered cell(s) described herein, or a combination therapy is administered to a subject receiving or recovering from immunosuppressive therapy. In certain embodiments, a genetically engineered cell(s) described herein, composition comprising a genetically engineered cell(s) described herein, or a combination therapy is administered to a subject that has or is at risk of getting AIDS, a viral infection, or a bacterial infection. In certain embodiments, a subject that is, will or has undergone surgery, chemotherapy and/or radiation therapy.

In some embodiments, a patient is administered a genetically engineered cell(s) described herein, composition comprising a genetically engineered cell(s) described herein, or a combination therapy is before any adverse effects or intolerance to therapies other than a genetically engineered cell(s) described herein develops. In some embodiments, A genetically engineered cell(s) described herein, compositions comprising A genetically engineered cell(s) described herein, or combination therapies are administered to refractory patients. In a certain embodiment, refractory patient is a patient refractory to a standard anti-cancer therapy. In certain embodiments, a patient with cancer, is refractory to a therapy when the cancer has not significantly been eradicated and/or the symptoms have not been significantly alleviated. The determination of whether a patient is refractory can be made either in vivo or in vitro by any method known in the art for assaying the effectiveness of a treatment, using art-accepted meanings of "refractory" in such a context. In various embodiments, a patient with cancer is refractory when a cancerous tumor has not decreased or has increased.

In some embodiments, a genetically engineered cell(s) described herein, compositions comprising a genetically engineered cell(s) described herein, or combination therapies are administered to a patient to protect against the onset or reoccurrence of cancer in a patient at risk of developing such cancer. In some embodiments, a genetically engineered cell(s) described herein, compositions comprising a genetically engineered cell(s) described herein, or combination therapies are administered to a patient who is susceptible to adverse reactions to conventional therapies.

In some embodiments, a genetically engineered cell(s) described herein, compositions comprising A genetically engineered cell(s) described herein, or combination therapies are administered to a patient who has proven refractory to therapies other than a genetically engineered cell(s) described herein, but are no longer on these therapies. In certain embodiments, the patients being managed or treated in accordance with the methods described herein are patients already being treated with antibiotics, anti-cancer agents, or other biological therapy/immunotherapy. Among these patients are refractory patients, patients who are too young for conventional therapies, and patients with reoccurring viral infections despite management or treatment with existing therapies.

In some embodiments, the subject being administered a genetically engineered cell(s) described herein, compositions comprising a genetically engineered cell(s) described herein, or combination therapies has not received a therapy prior to the administration of the genetically engineered cell(s) described herein, compositions comprising a genetically engineered cell(s) described herein, or combination therapies. In other embodiments, a genetically engineered cell(s) described herein, compositions comprising a genetically engineered cell(s) described herein, or combination therapies are administered to a subject who has received a therapy prior to administration of one or more a genetically engineered cell(s) described herein, compositions comprising a genetically engineered cell(s) described herein, or combination therapies. In some embodiments, the subject administered a genetically engineered cell(s) described herein or a composition comprising a genetically engineered cell(s) described herein was refractory to a prior therapy or experienced adverse side effects to the prior therapy or the prior therapy was discontinued due to unacceptable levels of toxicity to the subject.

5.5.2 Methods for Treating, Protecting Against, and Managing Infectious Diseases In a specific aspect, presented herein are methods for treating, protecting against, and/or managing an infectious disease, comprising administering to a subject in need thereof an effective amount of genetically engineered cells described herein or a composition thereof. In a specific embodiment, the genetically engineered cells described herein or a composition thereof is the only active agent administered to a subject. In certain embodiments, the genetically engineered cells described herein that are administered to the subject are autologous cells. In other embodiments, the genetically engineered cells described herein that are administered to the subject are donor cells.

In certain embodiments, administering a genetically engineered cell(s) described herein or a composition thereof to a subject (in some embodiments, an animal model) achieves one, two, three, four, or more of the following effects: (i) reduction or amelioration the severity of an infectious disease or symptom associated therewith; (ii) reduction in the duration of an infectious disease or symptom associated therewith; (iii) protection against the progression of an infectious disease or symptom associated therewith; (iv) regression of an infectious disease or symptom associated therewith; (v) protection against the development or onset of an infectious disease or symptom associated therewith; (vi) protection against the recurrence of an infectious disease or symptom associated therewith; (vii) reduction of or protection against the spread of an infectious agent from one cell to another cell, one tissue to another tissue, or one organ to another organ; (viii) protection against or reduction of the spread/transmission of an infectious agent from one subject to another subject; (ix) reduction in organ failure associated with an infectious disease; (x) reduction in the hospitalization of a subject; (xi) reduction in the hospitalization length; (xii) an increase in the survival of a subject with an infectious disease; (xiii) elimination of an infectious disease; (xiii) inhibition or reduction in replication of an infectious agent; (xiv) inhibition or reduction in the entry of an infectious agent into a cell(s); (xv) inhibition or reduction of replication of the genome of an infectious agent; (xvi) inhibition or reduction in the synthesis of infectious agent proteins; (xvii) inhibition or reduction in the assembly of infectious agents; (xviii) inhibition or reduction in the release of infectious agents from a cell(s); (xviii) reduction in the number or titer of an infectious agent; (xix) the reduction in the number of symptoms associated with an infectious disease (xx) enhancement, improvement, supplementation, complementation, or augmentation of the prophylactic or therapeutic effect(s) of another therapy; and (xxi) protection against the onset or progression of a secondary infection associated with an infectious disease.

In certain embodiments, administering a genetically engineered cell(s) described herein or a composition comprising a genetically engineered cell(s) described herein to a subject (in some embodiments, an animal model) infected with an infectious agent inhibits or reduces replication of the infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, administering a genetically engineered cell(s) described herein or a composition comprising a genetically engineered cell(s) described herein to a subject (in some embodiments, an animal model) infected with an infectious agent inhibits or reduces replication of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, administering a genetically engineered cell(s) described herein or a composition comprising a genetically engineered cell(s) described herein to a subject (in some embodiments, an animal model) infected with an infectious agent inhibits or reduces replication of the infectious agent by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, administering a genetically engineered cell(s) described herein or a composition comprising a genetically engineered cell(s) described herein to a subject (in some embodiments, an animal model) infected with an infectious agent reduces the titer of the infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, administering a genetically engineered cell(s) described herein or a composition comprising a genetically engineered cell(s) described herein to a subject (in some embodiments, an animal model) infected with an infectious agent reduces the titer of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, administering a genetically engineered cell(s) described herein or a composition comprising a genetically engineered cell(s) described herein to a subject (in some embodiments, an animal model) infected with an infectious agent reduces the titer of the infectious agent by 1 log, 1.5 logs, 2 logs, 2.5 logs, 3 logs, 3.5 logs, 4 logs, 5 logs or more relative to a negative control as determined using an assay described herein or others known to one of skill in the art.

In some embodiments, a genetically engineered cell(s) described herein is administered to a subject in combination with one or more other therapies. Non-limiting examples of other therapies that can be used in combination with a genetically engineered cell(s) are described herein. In one embodiment, the combination of a genetically engineered cell(s) described herein and one or more other therapies provides an additive therapeutic effect relative to the therapeutic effects of the genetically engineered cell(s) alone or the one or more other therapies alone. In one embodiment, the combination of a genetically engineered cell(s) described herein and one or more other therapies provides more than an additive therapeutic effect relative to the therapeutic effects of the genetically engineered cell(s) alone or the one or more other therapies alone. In one embodiment, the combination of a genetically engineered cell(s) described herein and one or more other therapies provides a synergistic therapeutic effect relative to the therapeutic effects of the genetically engineered cell(s) alone or the one or more other therapies alone.

In a specific embodiment, a genetically engineered cell(s) described herein is administered to a subject in combination with one or more antibiotics. In another embodiment, a genetically engineered cell(s) described herein is administered in combination with one or more anti-virals. In another embodiment, a genetically engineered cell(s) described herein is administered in combination with one or more anti-fungals.

5.5.2.1 Types of Infectious Diseases

Infectious diseases that can be treated, protected against, and/or managed by a genetically engineered cell(s) described herein are caused by infectious agents including, but not limited to, bacteria, fungi, protozoa, and viruses. Viral diseases that can be treated, protected against and/or managed in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral miningitis, encephalitis, dengue or small pox.

Bacterial diseases caused by bacteria (e.g., *Escherichia coli, Klebsiella pneumoniae, Staphylococcus aureus, Enterococcus faecials, Proteus vulgaris, Staphylococcus viridans*, and *Pseudomonas aeruginosa*) that can be treated, protected against and/or managed in accordance with the methods described herein include, but are not limited to, mycobacteria *rickettsia, mycoplasma, neisseria, S. pneumonia, Borrelia burgdorferi* (Lyme disease), *Bacillus antracis* (anthrax), tetanus, *streptococcus, staphylococcus, mycobacterium, pertissus,* cholera, plague, diptheria, *chlamydia, S. aureus* and *legionella*.

Protozoan diseases caused by protozoa that can be treated, protected against, and/or managed in accordance with the methods described herein include, but are not limited to, *leishmania, kokzidioa, trypanosoma schistosoma* or malaria. Parasitic diseases caused by parasites that can be treated, protected against, and/or managed in accordance with the methods described herein include, but are not limited to, *chlamydia* and *rickettsia*.

5.5.2.2 Patient Populations

In some embodiments, a genetically engineered cell(s) described herein, compositions comprising a genetically engineered cell(s) described herein, or combination therapies are administered to a subject suffering from an infectious disease caused by infectious agents including, but not limited to bacteria, fungi, protozoa, and viruses. In certain embodiments, a genetically engineered cell(s) described herein, compositions comprising a genetically engineered cell(s) described herein, or combination therapies are administered to a subject diagnosed as having an infectious disease caused by infectious agents including, but not limited to bacteria, fungi, protozoa, and viruses. In other embodiments, a genetically engineered cell(s) described herein, compositions comprising a genetically engineered cell(s) described herein, or combination therapies are administered to a subject predisposed or susceptible to an infectious disease. In some embodiments, a genetically engineered cell(s) described herein, compositions comprising a genetically engineered cell(s) described herein, or combination therapies are administered to a subject that lives in a region where there has been or might be an outbreak with infections by infectious agents. In some embodiments, the infection is a latent infection. In other embodiments, the infection by the infectious agent is an active infection. In yet other embodiments, the infection by the infectious agent is a chronic infection.

In some embodiments, a genetically engineered cell(s) described herein, composition comprising a genetically engineered cell(s) described herein, or a combination therapy is administered to a mammal. In certain embodiments, a genetically engineered cell(s) described herein, composition comprising a genetically engineered cell(s) described herein, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a genetically engineered cell(s) described herein, composition comprising a genetically engineered cell(s) described herein, or a combination therapy is administered to a pet, e.g., a dog or cat. In certain embodiments, a genetically engineered cell(s) described herein, composition comprising a genetically engineered cell(s) described herein, or a combination therapy is administered to a farm animal or livestock, e.g., pig, cows, horses, chickens, etc. In certain embodiments, a genetically engineered cell(s) described herein, composition comprising a genetically engineered cell(s) described herein, or a combination therapy is administered to a bird, e.g., ducks or chicken.

In certain embodiments, a genetically engineered cell(s) described herein, composition comprising a genetically engineered cell(s) described herein, or a combination therapy is administered to a human at risk of an infectious disease. In certain embodiments, a genetically engineered cell(s) described herein, composition comprising a genetically engineered cell(s) described herein, or a combination therapy is administered to a human with an infectious disease. In some embodiments, a genetically engineered cell(s) described herein, composition comprising a genetically engineered cell(s) described herein, or a combination therapy is administered to a human diagnosed as having an infectious disease. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a genetically engineered cell(s) described herein, composition comprising a genetically engineered cell(s) described herein, or a combination therapy is administered to a human infant or premature human infant. In other embodiments, a genetically engineered cell(s) described herein, composition comprising a genetically engineered cell(s) described herein, or a combination therapy is administered to a human child. In other embodiments, a genetically engineered cell(s) described herein, composition comprising a genetically engineered cell(s) described herein, or a combination therapy is administered to a human adult. In yet other embodiments, a genetically engineered cell(s) described herein, composition comprising a genetically engineered cell(s) described herein, or a combination therapy is administered to an elderly human.

In certain embodiments, a genetically engineered cell(s) described herein, composition comprising a genetically engineered cell(s) described herein, or a combination therapy is administered to a primate, preferably a human, or another mammal, such as a pig, cow, horse, sheep, goat, dog, cat and rodent, in an immunocompromised state or immunesuppressed state or at risk for becoming immunocompromised or immunesuppressed. In certain embodiments, a genetically engineered cell(s) described herein, composition comprising a genetically engineered cell(s) described herein, or a combination therapy is administered to a subject receiving or recovering from immunosuppressive therapy. In certain embodiments, a genetically engineered cell(s) described herein, composition comprising a genetically engineered cell(s) described herein, or a combination therapy is administered to a subject that has or is at risk of getting cancer, AIDS, another infection, or a bacterial infection. In certain embodiments, a subject that is, will or has undergone surgery, chemotherapy and/or radiation therapy. In certain embodiments, a genetically engineered cell(s) described herein, composition comprising a genetically engineered cell(s) described herein, or a combination therapy is administered to a subject that has cystic fibrosis, pulmonary fibrosis, or another disease which makes the subject susceptible to an infection. In certain embodiments, a genetically engineered cell(s) described herein, composition comprising a genetically engineered cell(s) described herein, or a combination therapy is administered to a subject that has, will have or had a tissue transplant. In some embodiments, a genetically engineered cell(s) described herein, composition comprising a genetically engineered cell(s) described herein, or a combination therapy is administered to a subject that lives in a nursing home, a group home (i.e., a home for 10 or more subjects), or a prison. In some embodiments, a genetically engineered cell(s) described herein, composition comprising a genetically engineered cell(s) described herein, or a combination therapy is administered to a subject that attends school (e.g., elementary school, middle school, junior high school, high school or university) or daycare. In some embodiments, a genetically engineered cell(s) described herein, composition comprising a genetically engineered cell(s) described herein, or a combination therapy is administered to a subject that works in the healthcare area, such as a doctor or a nurse, or in a hospital. In certain embodiments, a genetically engineered cell(s) described herein, composition comprising a genetically engineered cell(s) described herein, or a combination therapy is administered to a subject that is pregnant or will become pregnant.

In some embodiments, a patient is administered a genetically engineered cell(s) described herein, composition comprising a genetically engineered cell(s) described herein, or a combination therapy before any adverse effects or intolerance to therapies other than a genetically engineered cell(s) develops. In some embodiments, a genetically engineered cell(s) described herein, compositions comprising a genetically engineered cell(s) described herein, or combination therapies are administered to refractory patients. In a certain embodiment, refractory patient is a patient refractory to a standard therapy. In certain embodiments, a patient with an infectious disease is refractory to a therapy when the infectious disease has not significantly been eradicated and/or the symptoms have not been significantly alleviated. The determination of whether a patient is refractory can be made either in vivo or in vitro by any method known in the art for assaying the effectiveness of a treatment of an infectious disease, using art-accepted meanings of "refractory" in such a context. In various embodiments, a patient with an infection is refractory when replication of the infectious agent has not decreased or has increased.

In some embodiments, a genetically engineered cell(s) described herein, compositions comprising a genetically engineered cell(s) described herein, or combination therapies are administered to a patient to protect against the onset or reoccurrence of an infectious disease in a patient at risk of developing such a disease. In some embodiments, a genetically engineered cell(s) described herein, compositions comprising a genetically engineered cell(s) described herein, or combination therapies are administered to a patient who is susceptible to adverse reactions to conventional therapies.

In some embodiments, a genetically engineered cell(s) described herein, compositions comprising a genetically engineered cell(s) described herein, or combination therapies are administered to a patient who has proven refractory to therapies other than a genetically engineered cell(s), but are no longer on these therapies. In certain embodiments, the patients being managed or treated in accordance with the methods described herein are patients already being treated with antibiotics, anti-virals, anti-fungals, or other biological therapy/immunotherapy. Among these patients are refractory patients, patients who are too young for conventional therapies, and patients with reoccurring viral infections despite management or treatment with existing therapies.

In some embodiments, the subject being administered a genetically engineered cell(s) described herein, compositions comprising a genetically engineered cell(s) described herein, or combination therapies has not received a therapy prior to the administration of the genetically engineered cell(s) described herein, compositions comprising a genetically engineered cell(s) described herein, or combination therapies. In other embodiments, a genetically engineered cell(s) described herein, compositions comprising a genetically engineered cell(s) described herein, or combination therapies are administered to a subject who has received a therapy prior to administration of a genetically engineered cell(s) described herein or compositions comprising a genetically engineered cell(s) described herein, or combination therapies. In some embodiments, the subject administered a genetically engineered cell(s) described herein or a composition comprising a genetically engineered cell(s) described herein was refractory to a prior therapy or experienced adverse side effects to the prior therapy or the prior therapy was discontinued due to unacceptable levels of toxicity to the subject.

5.6 Administration and Dosage 5.6.1 Mode of Administration

A genetically engineered cell(s) described herein or composition thereof can be administered via any route known in the art. A genetically engineered cell(s) described herein or compositions thereof can be administered by, for example, infusion or bolus injection, and may be administered together with another biologically active agent. Administration can be systemic or local. Various delivery systems are known, e.g., encapsulation in liposomes, microparticles, microcapsules, capsules, and can be used to deliver a genetically engineered cell(s) described herein or compositions thereof and pharmaceutically acceptable salts thereof.

Methods of administration include but, are not limited to, parenteral, intradermal, intramuscular, intraperitoneal, intravenous, subcutaneous, intracerebral, or intratumorally. The mode of administration is left to the discretion of the practitioner.

In specific embodiments, it may be desirable to administer a genetically engineered cell(s) or composition thereof locally. This may be achieved, for example, and not by way of limitation, by local infusion or by means of an implant, said implant being of a porous or gelatinous material, including membranes, such as sialastic membranes, or fibers.

In another embodiment, a genetically engineered cell(s) is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327).

5.6.2 Dosage

The amount of a genetically engineered cell(s) described herein, or the amount of a composition comprising a genetically engineered cell(s) described herein, that will be effective in the treatment of, protection against, and/or management of a disease can be determined by standard clinical techniques. In vitro or in vivo assays may optionally be employed to help identify optimal dosage ranges. The precise dose to be employed will also depend, e.g., on the route of administration, the type of symptoms, and the seriousness of the symptoms, and should be decided according to the judgment of the practitioner and each patient's or subject's circumstances.

Doses of genetically engineered cells described herein for administration by any route of administration can be at least 100, 200, 300, 400, 500, 700, 1,000, 5,000, 10,000, 25,000, 50,000, or 100,000 cells. In specific embodiments, the number of cells is at least 100, 200, 300, 400, 500 cells. In other embodiments, the number of cells is at least 300, 400, 500, 700, 1,000 cells. In yet other specific embodiments, the number of cells is at least 700, 1,000, 5,000, 10,000 cells. In some embodiments, the number of cells is at least 5,000, 10,000, 25,000, 50,000, or 100,000 cells. In yet another embodiment, the number of cells is at least 50,000, or 100,000 cells. In other embodiments, the number of cells is at least $1\times10^6$, $5\times10^6$, $1\times10^7$, $5\times10^7$, $1\times10^8$, $5\times10^8$ or more cells. In specific embodiments, the number of cells is between $1\times10^2$ to $1\times10^4$, $5\times10^4$ to $5\times10^6$, $1\times10^5$ to $1\times10^7$, $1\times10^5$ to $5\times10^8$, $1\times10^6$ to $1\times10^8$, or $1\times10^6$ to $1\times10^7$, or $1\times10^4$ to $1\times10^5$ cells.

In certain embodiments, a subject is administered a genetically engineered cell(s) described herein or composition thereof in an amount effective to inhibit or reduce symptoms associated with a disease or disorder by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments to treat, a subject is administered a genetically engineered cell(s) described herein or a composition thereof in an amount effective to inhibit or reduce symptoms associated with a disease or disorder by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments to treat or manage an infectious disease, a subject is administered a genetically engineered cell(s) described herein or composition thereof in an amount effective to inhibit or reduce replication of an infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a genetically engineered cell(s) described herein or composition thereof in an amount effective to inhibit or reduce replication of an infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a genetically engineered cell(s) described herein or composition thereof in an amount effective to inhibit or reduce replication of an infectious agent by at least 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, to treat, protect against, and/or manage cancer, a subject is administered a genetically engineered cell(s) described herein or composition thereof in an amount effective to inhibit or reduce tumor growth or cancer cell proliferation by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a genetically engineered cell(s) described herein or composition thereof in an amount effective to inhibit or reduce tumor growth or cancer cell proliferation by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to, a subject is administered a genetically engineered cell(s) described herein or composition thereof in an amount effective to induce or enhance an immune response by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a genetically engineered cell(s) described herein or composition thereof in an amount effective to induce or enhance an immune response by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to, a subject is administered a genetically engineered cell(s) described herein or composition thereof in an amount effective to increase or enhance the number of lymphocytes (in some embodiments, in a specific target body compartment) by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a genetically engineered cell(s) described herein or composition thereof in an amount effective to increase or enhance the number of lymphocytes (in some embodiments, in a specific target body compartment) by at least 1.5 fold, at least 2 fold, at least 2.5 fold, at least 3 fold, at least 4 fold, at least 5 fold, at least 8 fold, at least 10 fold, at least 15 fold, or at least 20 fold; or by approximately 2 to 5 fold, 2 to 10 fold, 5 to 10 fold, or 5 to 20 fold relative to a negative control as determined using an assay described herein or others known to one of skill in the art. In some embodiments, the specific target body compartment where the number of lymphocytes is increased or enhanced by a genetically engineered cell(s) described herein is the lung, stomach, heart, kidney, liver, small intestines, large intestines, breast, prostate, or bladder. In particular embodiments, the specific target body compartment where the number of lymphocytes is increased or enhanced is the body compartment affected by a disease or disorder (e.g., cancer or infectious disease). In some embodiments, the specific target body compartment where the number of lymphocytes is increased or enhanced is the lymph node, spleen, or peripheral blood.

In certain embodiments, a dose of a genetically engineered cell(s) described herein or composition thereof is administered to a subject every day, every other day, every couple of days, every third day, once a week, twice a week, three times a week, or once every two weeks. In other embodiments, two, three or four doses of a genetically engineered cell(s) described herein or composition thereof is administered to a subject every day, every couple of days, every third day, once a week or once every two weeks. In some embodiments, a dose(s) of a genetically engineered cell(s) described herein or composition thereof is administered for 2 days, 3 days, 5 days, 7 days, 14 days, or 21 days. In certain embodiments, a dose of a genetically engineered cell(s) described herein or composition thereof is administered for 1 month, 1.5 months, 2 months, 2.5 months, 3 months, 4 months, 5 months, 6 months or more.

The dosages of prophylactic or therapeutic agents which have been or are currently used for the treatment of, protection against, and/or management of a disease or disorder, such as, e.g., cancer or an infectious disease, can be determined using references available to a clinician such as, e.g., the Physicians' Desk Reference (67th ed. 2013). In a specific embodiment, dosages lower than those which have been or are currently being used to treat, protect against, and/or manage the disease or disorder are utilized in combination with a genetically engineered cell(s) described herein or compositions thereof.

The above-described administration schedules are provided for illustrative purposes only and should not be considered limiting.

5.7 Biological Assays 5.7.1 Binding Assays

Binding assays can be used to determine the binding affinity of a chimeric receptor complex expressed by a genetically engineered cell(s) described herein for one or more of NKG2D's ligands (e.g., MHC class I chain-related A, MHC class I chain-related B, and UL-16-binding proteins). Binding assays may be performed either as direct binding assays or as competition-binding assays. Binding can be detected using standard ELISA or standard flow cytometry assays. In a direct binding assay a genetically engineered cell(s) described herein is tested for binding to NKG2D's ligands (e.g., MHC class I chain-related A, MHC class I chain-related B, and UL-16-binding proteins).

Competition-binding assays, on the other hand, assess the ability of a genetically engineered cell(s) described herein to compete with a known agent (e.g., antibodies or other compound) that binds to an NKG2D ligand (e.g., MHC class I chain-related A, MHC class I chain-related B, or a UL-16-binding protein).

In a direct binding assay, a genetically engineered cell(s) described herein is contacted with an NKG2D ligand under conditions that allow binding of the chimeric receptor complex expressed by the cell(s) to the ligand. The binding may take place in solution or on a solid surface. The ligand may be labeled with any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound ligand. Typically, it involves washing with an appropriate buffer. Finally, the presence of a genetically engineered cell(s) bound to ligand is detected.

Alternatively, a genetically engineered cell(s) described herein is contacted with an NKG2D ligand under conditions that allow binding of the chimeric receptor complex expressed by the cell(s) to the ligand. The binding may take place in solution or on a solid surface. After a period of incubation sufficient for binding to take place, the reaction is exposed to conditions and manipulations that remove excess or non-specifically bound ligand. Typically, it involves washing with an appropriate buffer. Then, the genetically engineered cell(s) is contacted with an antibody specific for the ligand, and after a period of incubation the cell(s) are washed with an appropriate buffer to remove excess or non-specifically bound antibody. Finally, the presence of a genetically engineered cell(s) bound to ligand is detected.

Various methods described herein (e.g., in the Examples, infra) or known in the art can be adapted to assay the binding affinity of a genetically engineered cell(s) for one or more NKG2D ligands.

5.7.2 Functional Assays

Various assays known in the art can be used to assess whether a genetically engineered cell(s) described herein expresses a chimeric receptor complex that triggers signal transduction. For example, a genetically engineered cell(s) described herein can be contacted with a ligand of NKG2D or an antibody specific for NKG2D, and the phosphorylation of the chimeric receptor complex and/or the activation of downstream signaling molecules can be assessed by techniques known to one of skill in the art (e.g., Antibody Microarray, Western Blot, immunoprecipitation followed by Western Blot, ELISA, electromobility shift assays). In a specific embodiment, the technique described in the Examples, infra, is used to assess whether a genetically engineered cell(s) described herein expresses a chimeric receptor complex that triggers signal transduction.

Various assays known in the art can be used to assess whether a genetically engineered cell(s) described herein activates or enhances an immune function. In one aspect, a genetically engineered cell(s) described herein increases an immune response that can be, e.g., an antibody response (humoral response) or a cellular immune response, e.g., cytokine secretion (e.g., interferon), chemokine secretion, helper activity or cellular cytotoxicity. In one embodiment, the increased immune response is increased cytokine secretion, antibody production, effector function, T cell proliferation, and/or NK cell proliferation. Various assays to measure such activities are well known in the art, and exemplary descriptions of such assays are provided below.

Proliferation of certain immune cells may assessed by $^3$H-thymidine incorporation. The cytotoxicity of T cells can be tested in a $^{51}$Cr-release assay as described in the art. In a specific embodiment, the cytotoxicity triggered by a genetically engineered cell(s) expressing a chimeric receptor complex is assessed using the techniques described in the Examples, infra.

An ELISPOT assay can be used to measure cytokine release in vitro by a genetically engineered cell(s) described herein. Cytokine secretion and/or chemokine secretion by a genetically engineered cell(s) described herein following contact with a ligand for NKG2D or an antibody specific for NKG2D can be detected by antibodies which are specific for a particular cytokine, e.g., interleukin-2, tumor necrosis factor-α or interferon-γ, or chemokine. In a specific embodiment, a cytokine and/or chemokine secretion by a genetically engineered cell(s) can be assessed using the techniques described in the Examples, infra.

In some aspects, the immune response induced or enhanced by a genetically engineered cell(s) is enhanced or increased by at least at least 10%, 15%, 20%, 25%, 30%, 40%, 50%, 60%, 70%, 75%, 80%, 90%. 95%, 98% or 99%, or in the range of between 10% to 25%, 10% to 50%, 25% to 50%, 25% to 75%, 50% to 75%, 50% to 90%, 75% to 90%, 75% to 100% relative to an immune response elicited by a negative control as determined by any known assay in the art. In certain embodiments, the immune response induced by a genetically engineered cell(s) is enhanced by at least 0.5-2 times, at least 2-5 times, at least 5-10 times, at least 10-50 times, at least 50-100 times, at least 100-200 times, at least 200-300 times, at least 300-400 times or at least 400-500 times relative to the immune response induced by a negative control as assayed by any known method in the art. In specific embodiments, the assay used to assess immune response measures the level of antibody production, cytokine production or secretion, chemokine production or secretion, or cellular cytotoxicity, and such assays are well known in the art. In some embodiments, the assay used to measure the immune response is an enzyme-linked immunosorbent assay (ELISA) that determines antibody or cytokine levels, an ELISPOT assay that determines cytokine release, or a $51^{Cr}$ release assay that determines cellular cytotoxicity.

In another specific embodiment, presented herein are methods of administering a genetically engineered cell(s) to induce or enhance the level of cytokine production or secretion, e.g., interferon-γ, (that may be 0.5 to 500 times higher) as compared to the level of cytokine production or secretion in a negative control sample. In specific embodiments, a genetically engineered cell(s) induces or enhances an immune response that is measured by increased cytokine release, and the cytokine concentration is at least 0.2 to 5 times, 5 to 20 times, 10 to 30 times, 20 to 50 times, 50 to 200 times, 100 to 500, 200 to 1000 times, or 500 to 2,000 times higher as compared to the cytokine concentration of a negative control. In specific embodiments, the mean serum cytokine concentration of samples obtained from a subject administered a genetically engineered cell(s) is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum cytokine concentration of samples obtained from a subject administered a negative control as determined by methods well known in the art. In some embodiments, the negative control can be samples from the subject prior to administration of a genetically engineered cell(s).

In another specific embodiment, presented herein are methods of administering a genetically engineered cell(s) to induce or enhance the level of chemokine production or secretion, e.g., interferon-γ, (that may be 0.5 to 500 times higher) as compared to the level of chemokine production or secretion in a negative control sample. In specific embodiments, a genetically engineered cell(s) induces or enhances an immune response that is measured by increased chemokine release, and the chemokine concentration is at least 0.2 to 5 times, 5 to 20 times, 10 to 30 times, 20 to 50 times, 50 to 200 times, 100 to 500, 200 to 1000 times, or 500 to 2,000 times higher as compared to the chemokine concentration of a negative control. In specific embodiments, the mean serum chemokine concentration of samples obtained from a subject administered a genetically engineered cell(s) is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum chemokine concentration of samples obtained from a subject administered a negative control as determined by methods well known in the art. In some embodiments, the negative control can be samples from the subject prior to administration of a genetically engineered cell(s).

In specific embodiments, a genetically engineered cell(s) described herein induces or enhances NK cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to NK cell proliferation in a negative control. In specific embodiments, a genetically engineered cell(s) described herein induces or enhances T cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to T cell proliferation in a negative control as determined by methods well known in the art, e.g., flow cytometry, CSFE staining, $^3$H-thymidine incorporation.

The increase in antibody (humoral) or cellular immune response induced by an effective amount of a genetically engineered cell(s) described herein can be assessed using various methods well known in the art.

5.7.3 Cytotoxicity Assays

The toxicity and/or efficacy of the therapies described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a genetically engineered cell(s) described herein for use in humans. The dosage of such agents lies preferably within a range of circulating concentrations that include the ED50 with little or no toxicity. The dosage may vary within this range depending upon the dosage form employed and the route of administration utilized. For any therapy used in the method, e.g., as described herein, the therapeutically effective dose can be estimated initially from cell culture assays.

In a specific embodiment, a genetically engineered cell(s) described herein does not exhibit a significant increase in cytotoxicity against normal cells (e.g., non-transformed peripheral blood lymphocytes, bone marrow-derived mesenchymal cells, uninfected cells, or non-tumor cells) relative to a cell of the same type that has not been genetically engineered to express a chimeric receptor complex described herein.

5.7.4 Animal Models

A genetically engineered cell(s) described herein is preferably assayed in non-human animals for the desired therapeutic or prophylactic activity prior to use in humans. For example, in one embodiment, a genetically engineered cell(s) described herein can be administered to the animal at the same time as the onset of a disease or disorder in the animal. In another embodiment, a genetically engineered cell(s) described herein can be administered to the animal prior to the onset of a disease or disorder in the animal. In another embodiment, a genetically engineered cell(s) described herein can be administered to the animal subsequent to the onset of a disease or disorder in the animal. In a specific embodiment, the genetically engineered cell(s) described herein is administered to the animal more than one time. In another specific embodiment, the genetically engineered cell(s) described herein is administered in combination with another therapy.

A genetically engineered cell(s) described herein can be tested in animal models systems including, but are not limited to, rats, mice, chicken, cows, monkeys, pigs, goats, sheep, dogs, rabbits, guinea pigs, etc. In a specific embodiment, a genetically engineered cell(s) described herein is tested in a mouse model system. Such model systems are widely used and well-known to the skilled artisan.

The anti-cancer activity of a genetically engineered cell(s) described herein can be determined by using various experimental animal models for the study of cancer well known in the art as described in, e.g., Relevance of Tumor Models for Anticancer Drug Development (1999, eds. Fiebig and Burger); Contributions to Oncology (1999, Karger); The Nude Mouse in Oncology Research (1991, eds. Boven and Winograd); and Anticancer Drug Development Guide (1997 ed. Teicher), incorporated herein by reference in their entireties.

Animal models for cancer can be used to assess the efficacy of a genetically engineered cell(s) described herein, a composition thereof, or a combination therapy. Non-limiting examples of animal models for lung cancer include, but are not limited to, lung cancer animal models described by Zhang & Roth (1994, In vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR-ÿ and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

For animal models of infectious diseases, the effectiveness of a genetically engineered cell(s) described herein relative to a negative control can be assessed in animals infected with an infectious agent (e.g., a virus or bacteria). Samples obtained from these animals (e.g., serum, urine, sputum, semen, saliva, plasma, or tissue sample) can be tested for enhancement of immune function, e.g., enhancement in cytokine secretion, chemokine secretion, enhancement in antibody production, T cell proliferation, NK cell proliferation, or cytotoxicity, with methods well known in the art and described herein. Samples obtained from these animals (e.g., serum, urine, sputum, semen, saliva, plasma, or tissue sample) can also be tested for reduction in replication of the infectious agent via well known methods in the art, e.g., those that measure altered replication (as determined, e.g., by plaque formation) or the production of infectious agent proteins (as determined, e.g., by Western blot, ELISA, or flow cytometry analysis) or infectious agent nucleic acids (as determined, e.g., by RT-PCR, northern blot analysis or southern blot). For quantitation of virus in tissue samples, tissue samples are homogenized in phosphate-buffered saline (PBS), and dilutions of clarified homogenates are adsorbed for 1 hour at 37° C. on monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody. Non-limiting exemplary animal models described below can be adapted for other viral systems.

Various animal models for infectious diseases that are well known in the art can be employed to assess the efficacy of a genetically engineered cell(s) described herein in treating, protecting against, and/or managing infectious diseases, e.g.: mouse models of herpes simplex virus (HSV) are described in Crute et al., Nature Medicine, 2002, 8:386-391 and Bolger et al., Antiviral Res., 1997, 35:157-165; guinea pig models of HSV are described in Chen et al., Virol. J, 2004 Nov. 23, 1:11; animal models of mouse cytomegalovirus (MCMV) and human cytomegalovirus (HCMV) are described in Kern et al., Antimicrob. Agents Chemother., 2004, 48:4745-4753; Guinea pig models of CMV is described in Bourne et al., Antiviral Res., 2000, 47:103-109, Bravo et al., Antiviral Res., 2003, 60:41-49 and Bravo et al, J. Infectious Diseases, 2006, 193:591-597; animal models of influenza virus are described in Sidwell et al., Antiviral Res., 2000, 48:1-16; and McCauley et al., Antiviral Res., 1995, 27:179-186; mouse models of hepatitis B virus (HBV) are described in Cavanaugh et al., J. Virol., 1997, 71:3236-3243 and Guidotti et al., J. Virol., 1995, 69:6158-6169; mouse models of hepatitis C virus (HCV) are described in Zhu et al., Antimicrobial Agents and Chemother., 2006, 50:3260-3268, Bright et al., Nature, 2005, 436:973-978, Hsu et al., Nat. Biotechnol., 2003, 21:519-525, Ilan et al., J. Infect. Dis. 2002, 185:153-161, Kneteman et al., Hepatology, 2006, 43:1346-1353, Mercer et al., Nat. Med., 2001, 7:927-933, and Wu et al., Gastroenterology, 2005, 128:1416-1423; animal models of HIV are described in Ayash-Rashkovsky et al., FASEB J., 2005, 19:1149-1151, Mosier et al., Semin. Immunol., 1996, 8:255-262, Mosier et al., Hosp. Pract. (Off Ed)., 1996, 31:41-48, 53-55, 59-60, Bonyhadi et al., Mol. Med. Today, 1997, 3:246-253, Jolicoeur et al., Leukemia, 1999, 13:S78-S80, Browning et al., Proc. Natl. Acad. Sci. USA, 1997, 94:14637-14641, and Sawada et al., J. Exp. Med., 1998, 187:1439-1449, and Schito et al., Curr. HIV Res., 2006, 4:379-386.

Other animal models for viral infections can also be used to assess the efficacy of a genetically engineered cell(s) described herein, a composition thereof, or a combination therapy, e.g., animal models for viral infections such as EBV-associated diseases, gammaherpesviruses, infectious mononucleosis, simian immunodeficiency virus ("SIV"), Borna disease virus infection, hepatitis, varicella virus infection, viral pneumonitis, Epstein-Barr virus pathogenesis, feline immunodeficiency virus ("FIV"), HTLV type 1 infection, human rotaviruses, and genital herpes have been developed (see, e.g., Hayashi et al., 2002, Histol Histopathol 17(4):1293-310; Arico et al., 2002, J Interferon Cytokine Res 22(11):1081-8; Flano et al., 2002, Immunol Res 25(3): 201-17; Sauermann, 2001, Curr Mol Med 1(4):515-22; Pletnikov et al., 2002, Front Biosci 7:d593-607; Engler et al., 2001, Mol Immunol 38(6):457-65; White et al., 2001, Brain Pathol 11(4):475-9; Davis & Matalon, 2001, News Physiol Sci 16:185-90; Wang, 2001, Curr Top Microbiol Immunol. 258:201-19; Phillips et al., 2000, J Psychopharmacol. 14(3):244-50; Kazanji, 2000, AIDS Res Hum Retroviruses. 16(16):1741-6; Saif et al., 1996, Arch Virol Suppl. 12:153-61; and Hsiung et al., 1984, Rev Infect Dis. 6(1): 33-50).

Other animal models for viral respiratory infections include, but not limited to, PIV (see, e.g., Shephard et al., 2003 Res Vet Sci 74(2): 187-190; Ottolini et al., 2002 J Infect Dis 186(12): 1713-1717), and RSV (see, e.g., Culley et al., 2002 J Exp Med 196(10): 1381-1386; and Curtis et al., 2002 Exp Biol Med 227(9): 799-802).

A genetically engineered cell(s) described herein, composition thereof, or combination therapy can be tested for their ability to decrease the time course of viral infection.

Animal models for bacterial infections can also be used to assess the efficacy of a genetically engineered cell(s) described herein, a composition thereof, or a combination therapy. Animal models for bacterial infections such as H. pylori-infection, genital mycoplasmosis, primary sclerosing cholangitis, cholera, chronic lung infection with Pseudomonas aeruginosa, Legionnaires' disease, gastroduodenal ulcer disease, bacterial meningitis, gastric Helicobacter infection, pneumococcal otitis media, experimental allergic neuritis, leprous neuropathy, mycobacterial infection, endocarditis, Aeromonas-associated enteritis, Bacteroides fragilis infection, syphilis, streptococcal endocarditis, acute hematogenous osteomyelitis, human scrub typhus, toxic shock syndrome, anaerobic infections, Escherichia coli infections, and Mycoplasma pneumoniae infections have been developed (see, e.g., Sugiyama et al., 2002, J Gastroenterol. 37 Suppl 13:6-9; Brown et al., 2001, Am J Reprod Immunol. 46(3): 232-41; Vierling, 2001, Best Pract Res Clin Gastroenterol. 15(4):591-610; Klose, 2000, Trends Microbiol. 8(4):189-91; Stotland et al., 2000, Pediatr Pulmonol. 30(5):413-24; Brieland et al., 2000, Immunopharmacology 48(3):249-52; Lee, 2000, Baillieres Best Pract Res Clin Gastroenterol. 14(1): 75-96; Koedel & Pfister, 1999, Infect Dis Clin North Am. 13(3):549-77; Nedrud, 1999, FEMS Immunol Med Microbiol. 24(2):243-50; Prellner et al., 1999, Microb Drug Resist. 5(1):73-82; Vriesendorp, 1997, J Infect Dis. 176 Suppl 2:S164-8; Shetty & Antia, 1996, Indian J Lepr. 68(1):95-104; Balasubramanian et al., 1994, Immunobiology 191(4-5):395-401; Carbon et al., 1994, Int J Biomed Comput. 36(1-2):59-67; Haberberger et al., 1991, Experientia. 47(5):426-9; Onderdonk et al., 1990, Rev Infect Dis. 12 Suppl 2:S169-77; Wicher & Wicher, 1989, Crit Rev Microbiol. 16(3):181-234; Scheld, 1987, J Antimicrob Chemother. 20 Suppl A:71-85; Emslie & Nade, 1986, Rev Infect Dis. 8(6):841-9; Ridgway et al., 1986, Lab Anim Sci. 36(5):481-5; Quimby & Nguyen, 1985, Crit Rev Microbiol. 12(1):1-44; Onderdonk et al., 1979, Rev Infect Dis. 1(2): 291-301; Smith, 1976, Ciba Found Symp. (42):45-72, and Taylor-Robinson, 1976, Infection. 4(1 Suppl):4-8).

A genetically engineered cell(s) described herein, a composition thereof, or a combination therapy can be tested for their ability to decrease the time course of bacterial infection, e.g., a bacterial respiratory infection by at least 25%, at least 50%, at least 60%, at least 75%, at least 85%, at least 95%, or at least 99% relative to a negative control using methods well known in the art.

The efficacy of a genetically engineered cell(s) described herein, a composition thereof, or a combination therapy for the treatment, protection against, and/or management of a fungal infection can be assessed in animal models for such infections. Animal models for fungal infections such as Candida infections, zygomycosis, Candida mastitis, progressive disseminated trichosporonosis with latent trichosporonemia, disseminated candidiasis, pulmonary paracoccidioidomycosis, pulmonary aspergillosis, Pneumocystis carinii pneumonia, cryptococcal meningitis, coccidioidal meningoencephalitis and cerebrospinal vasculitis, Aspergillus niger infection, Fusarium keratitis, paranasal sinus mycoses, Aspergillus fumigatus endocarditis, tibial dyschondroplasia, Candida glabrata vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, Cryptococcus neoformans infection, fungal peritonitis, Curvularia geniculata infection, staphylococcal endophthalmitis, sporotrichosis, and dermatophytosis have been developed (see, e.g., Arendrup et al., 2002, Infection 30(5):286-91; Kamei, 2001, Mycopathologia 152 (1):5-13; Guhad et al., 2000, FEMS Microbiol Lett. 192(1): 27-31; Yamagata et al., 2000, J Clin Microbiol. 38(9):32606; Andrutis et al., 2000, J Clin Microbiol. 38(6):2317-23; Cock et al., 2000, Rev Inst Med Trop Sao Paulo 42(2):59-66; Shibuya et al., 1999, Microb Pathog. 27(3):123-31; Beers et al., 1999, J Lab Clin Med. 133(5):423-33; Najvar et al., 1999, Antimicrob Agents Chemother. 43(2):413-4; Williams et al., 1988, J Infect Dis. 178(4):1217-21; Yoshida, 1988, Kansenshogaku Zasshi. 1998 June; 72(6):621-30; Alexandrakis et al., 1998, Br J Ophthalmol. 82(3):306-11; Chakrabarti et al., 1997, J Med Vet Mycol. 35(4):295-7;

Martin et al., 1997, Antimicrob Agents Chemother. 41(1): 13-6; Chu et al., 1996, Avian Dis. 40(3):715-9; Fidel et al., 1996, J Infect Dis. 173(2):425-31; Cole et al., 1995, FEMS Microbiol Lett. 15; 126(2):177-80; Pollock et al., 1995, Nat Genet. 9(2):202-9; Uchida et al., 1994, Jpn J Antibiot. 47(10):1407-12; Maebashi et al., 1994, J Med Vet Mycol. 32(5):349-59; Jensen & Schonheyder, 1993, J Exp Anim Sci. 35(4):155-60; Gokaslan & Anaissie, 1992, Infect Immun. 60(8):3339-44; Kurup et al., 1992, J Immunol. 148(12):3783-8; Singh et al., 1990, Mycopathologia. 112 (3):127-37; Salkowski & Balish, 1990, Infect Immun. 58(10):3300-6; Ahmad et al., 1986, Am J Kidney Dis. 7(2):153-6; Alture-Werber E, Edberg S C, 1985, Mycopathologia. 89(2):69-73; Kane et al., 1981, Antimicrob Agents Chemother. 20(5):595-9; Barbee et al., 1977, Am J Pathol. 86(1):281-4; and Maestrone et al., 1973, Am J Vet Res. 34(6):833-6). Animal models for fungal respiratory infections such as *Candida albicans, Aspergillus fumigatus,* invasive pulmonary aspergillosis, *Pneumocystis carinii*, pulmonary cryptococcosis, *Pseudomonas aeruginosa, Cunninghamella bertholletia* (see, e.g., Aratani et al., 2002 Med Mycol 40(6):557-563; Bozza et al., 2002 Microbes Infect 4(13): 1281-1290; Kurup et al., 2002 Int Arch Allergy Immunol 129(2):129-137; Hori et al., 2002 Eur J Immuno 32(5): 1282-1291; Rivera et al., 2002 J Immuno 168(7): 3419-3427; Vassallo et al., 2001, Am J Respir Cell Mol Biol 25(2): 203-211; Wilder et al., 2002 Am J Respir Cell Mol Biol 26(3): 304-314; Yonezawa et al., 2000 J Infect Chemother 6(3): 155-161; Cacciapuoti et al., 2000 Antimicrob Agents Chemother 44(8): 2017-2022; and Honda et al., 1998 Mycopathologia 144(3): 141-146).

A genetically engineered cell(s) described herein, a composition thereof, or a combination therapy can be tested for their ability to decrease the time course of fungal infection by at least 25%, at least 50%, at least 60%, at least 75%, at least 85%, at least 95%, or at least 99%.

Techniques known to those of skill in the art can be used to analyze the function of a genetically engineered cell(s) described herein, a composition thereof, or a combination therapy in vivo.

5.8 Kits

Provided herein is a pharmaceutical pack or kit comprising one or more containers filled with a polynucleotide comprising a nucleotide sequence encoding a chimeric receptor complex described herein. Also provided herein is a pharmaceutical pack or kit comprising one or more containers filled with cells (in particular, NK cells and/or T cells) comprising a polynucleotide comprising a nucleotide sequence encoding a chimeric receptor complex described herein. Optionally associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical pack or kit may include instructions for use of the polynucleotide or genetically engineered cells described herein.

The kits encompassed herein can be used in the above methods.

6. EXAMPLES

The following examples of the invention are included by way of illustration, and not by way of limitation.

Based on the concept that supra-physiologic activating signals could be used to enhance NK cell antitumor capacity and could result in an increased usefulness of NK cells in therapeutic applications, a construct encoding a chimeric receptor comprising NKG2D, DAP10 and the intracellular domain of CD3zeta, a signaling molecule known to trigger cytotoxicity in NK cells (Andre et al., 2004, Eur. J. Immunol. 34:961-971; Imai et al., 2005, Blood 106, 376-383), was designed and constructed using recombinant DNA methods, then expressed in activated NK cells. The expression of the chimeric receptor and its signaling profile and anticancer potential was examined in vitro and in vivo.

6.1 Materials and Methods 6.1.1 Tumor Cell Lines

The human B-lineage ALL cell lines OP-1 and REH, and the T-lineage ALL cell lines CEM-C7, Jurkat and MOLT-4 were obtained from the St. Jude Children's Research Hospital tissue repository. The cell lines U-2 OS, HOS and MG-63 (osteosarcoma), DU 145, PC-3 and LNCaP (prostate carcinoma), Km12L4 (colon carcinoma), SNU1 (gastric carcinoma), SW900 (lung squamous cell carcinoma), HepG2 (hepatocellular carcinoma) and MCF7 (breast carcinoma) were obtained from the American Type Culture Collection (ATCC; Rockville, Md.). The rhabdomyosarcoma cell lines RH18, RH36, TE-32 and the neuroblastoma cell line SKNSH were provided by Dr. Peter Houghton (Children's Hospital, Columbus, Ohio); RH30 (rhabdomyosarcoma) was available from the St. Jude Children's Research Hospital tissue repository (Cho et al., 2010, Clin Cancer Res. 16:3901-3909). Human mesenchymal cells (MSC) were developed in the laboratory (Mihara et al., 2003, Br. J. Haematol. 120:846-849). RPMI-1640 (Invitrogen, Carlsbad, Calif.) supplemented with 10% fetal bovine serum (FBS; Atlanta Biologicals, Lawrenceville, Ga.) and antibiotics was used to maintain all cell lines with the exception of U2-OS, HOS and MG-63, which were maintained in DMEM (Cellgro, Manassas, Va.).

For the visualization of injected tumor cells in immunodeficient mice, the U-2 OS cell line was transduced with a murine stem cell virus (MSCV)-internal ribosome entry site (IRES)-GFP retroviral vector (from the St. Jude Vector Development and Production Shared Resource) containing the firefly luciferase gene. Transduced cells were selected for their expression of GFP with a FACSAria cell sorter (BD Biosciences, San Jose, Calif.).

6.1.2 Human NK cell Expansion

Peripheral blood samples were obtained from healthy adult donors. Mononuclear cells collected from the samples by centrifugation on a Lymphoprep density step (Nycomed, Oslo, Norway) were washed twice in RPMI-1640. To expand CD56+ CD3-NK cells, peripheral blood mononuclear cells and the genetically modified K562-mb15-41BBL cell line made in the laboratory were co-cultured, as previously described (Imai et al., 2005, Blood 106:376-383; Fujisaki et al., 2009, Cancer Res. 69: 4010-4017). Briefly, peripheral blood mononuclear cells ($1.5 \times 10^6$) were cultured in a 24-well tissue culture plate with $1 \times 10^6$ K562-mb15-41BBL cells in RPMI-1640 medium containing and 10% FBS and 10 IU/mL human IL-2 (National Cancer Institute BRB Preclinical Repository, Rockville, Md.). Every 2 days the tissue culture medium was exchanged with fresh medium and IL-2. After 7 days of co-culture, residual T cells were removed using Dynabeads CD3 (Invitrogen, Carlsbad, Calif.), producing cell populations containing >95% CD56+ CD3-NK cells.

6.1.3 Plasmids

The pMSCV-IRES-GFP, pEQ-PAM3(-E), and pRDF were obtained from the St. Jude Vector Development and Production Shared Resource (Imai et al., 2004, Leukemia 18:676-684). The cDNA encoding NKG2D, DAP10 and the intracellular domain of CD3 zeta were subcloned by PCR using cDNA derived from expanded NK cells as a template. Several constructs containing combinations of these molecules were prepared and the expression cassettes were subcloned into EcoRI sites of MSCV vector. Because NKG2D and CD3ζ are type II and type I proteins, respectively, the ATG initiation codon of NKG2D was removed and an ATG start codon was added to the cDNA of the intracellular domain of CD3 zeta to prepare a construct containing both proteins, as previously described (Zhang et al., 2007, Cancer Res. 67:11029-11036). NKG2D and CD3 zeta were then assembled using splicing by overlapping extension by PCR (SOE-PCR). The GFP in the vector was then replaced with DAP10 (containing a FLAG-tag) between the NcoI and NotI sites; one nucleotide was then removed from the NcoI site to make DAP10 in frame.

6.1.4 Virus Production and Gene Transduction

To generate RD144-pseudotyped retrovirus, fuGENE 6 (Roche, Indianapolis, Ind.) $2.5 \times 10^6$ 293 T cells were transfected with 3.5 µg of cDNA encoding NKG2D constructs, 3.5 µg of pEQ-PAM3(-E), and 3 µg of pRDF, and maintained in 10-cm tissue culture dishes for 16 h (Imai et al., 2004, Leukemia 18:676-684; Imai et al., 2005, Blood 106:376-383). After replacing the medium with RPMI-1640 with 10% FCS and antibiotics at 24 hours, the conditioned medium containing retrovirus at 48, 72 and 96 hours were harvested and added it to RetroNectin (TaKaRa, Otsu, Japan)-coated polypropylene tubes, which were centrifuged at 1400 g for 10 min and incubated at 37° C. for 4 hours. After additional centrifugation, and removal of the supernatant, expanded NK cells ($5 \times 10^5$) were added to the tubes and left in at 37° C. for 24 h. This procedure was repeated on two other successive days. Cells were then maintained in RPMI-1640 with FBS, antibiotics and 50 IU/ml of IL-2 until the time of the experiments, 3-10 days after transduction.

6.1.5 Analysis of Expression

Surface expression of NKG2D was analyzed by flow cytometry using an anti-human NKG2D antibody conjugated to peridinin chlorophyll protein (R&D, Minneapolis, Minn.). Expression of DAP10-FLAG was visualized with an anti-FLAG antibody conjugated to phycoerythrin (Abcam, Cambridge, Mass.). For Western blotting, NK cells were incubated with 0.1 µM sodium orthovanadate and 0.034% $H_2O_2$ at 37° C. for 10 minutes. Cells were lysed in Cellytic M lysis Buffer (Sigma, St. Louis, Mo.) containing 1% protease inhibitor cocktail (Sigma) and 1% phosphatase inhibitor cocktail 2 (Sigma). After centrifugation, lysate supernatants were boiled with an equal volume of LDS buffer (Invitrogen, Carlsbad, Calif.) with or without reducing buffer (Invitrogen) and then separated by NuPAGE Novex 12% Bis-Tris Gel (Invitrogen). The proteins were transferred to a polyvinylidene fluoride (PVDF) membrane, which was incubated with a rabbit anti-human CD3zeta phospho (pY83) antibody (clone EP776(2)Y; Epitomics, Burlingame, Calif.). Membranes were then washed, incubated with a goat anti-rabbit IgG horseradish peroxidase-conjugated second antibody (Cell Signaling, Danvers, Mass.), and developed by using the Amersham ECL Prime detection reagent (GE Healthcare).

6.1.6 mRNA Electroporation

The pCMV6-XL5 vector (Origene, Rockville, Md.) was used as a template for in vitro mRNA transcription. The NKG2D-CD3zeta and DAP10 cDNA were subcloned into EcoRI and XbaI sites of pCMV6-XL5, respectively. The corresponding mRNA were transcribed in vitro with T7 RNA polymerase using Ambion mMESSAGE mMACHINE T7 Ultra kit (Ambion, Austin, Tx) (Shimasaki et al., 2012, Cytotherapy 14:830-840).

For electroporation the MaxCyte GT system (MaxCyte, Gaithersburg, Md.) was used, as previously described (Shimasaki et al., 2012, Cytotherapy 14:830-840). Briefly, expanded NK cells ($4 \times 10^6$) were washed once with EP buffer (MaxCyte), mixed with 400 µg/ml mRNA, transferred into the processing chamber, and transfected using the program "NK#2" (Shimasaki et al., 2012, Cytotherapy 14:830-840). Immediately after electroporation, cells were transferred from the processing chamber to a 96-well plate, incubated for 20 minutes at 37° C., and then cultured in RPMI-1640 with FBS, antibiotics and 50 IU/mL IL-2.

6.1.7 Cytotoxicity and Degranulation Assays

Target cells were suspended in RPMI-1640 with 10% FBS, labeled with calcein AM, and plated into 96-well flat bottom plates (Costar, Corning, N.Y.). Expanded NK cells, suspended in RPMI-1640 with 10% FBS and 50 IU/mL IL-2 were then added at various E: T ratios as indicated in Results, and cocultured with target cells for 4 hours. Cell were then stained with propridium iodide and cytotoxicity was measured by flow cytometry using a FACScan (Becton Dickinson), enumerating the number of viable target cells (calcein AM-positive, propidium-iodide negative, and light scattering properties of viable cells) (Fujisaki et al., 2009, Cancer Res. 69: 4010-4017). For adherent cell lines, the plates were placed in an incubator for at least 4 hours to allow for cell attachment before adding NK cells. At the end of the cultures, cells were detached using trypsin plus EDTA. In some experiments, NK cells were incubated with anti-NKG2D (clone 149810; R&D), anti-CD56 (BD Biosciences) or an isotype-matched non-reactive antibody for 10 minutes before coculture.

NK cell degranulation after NKG2D stimulation was directly tested with an anti-NKG2D antibody. NK cells ($1 \times 10^5$) were plated into each well of a 96-well round bottom plate and incubated with anti-Biotin MACSiBeads (Miltenyi Biotec, Auburn, Calif.) coated with biotin-conjugated anti-NKG2D antibody (clone 1D11; eBioscience; San Diego, Calif.) (ten beads for one NK cell) for 4 hours at 37° C. An anti-human CD107a antibody conjugated to phycoerythrin (BD Biosciences) was added at the beginning of the cultures and one hour later GolgiStop (0.15 µl; BD Biosciences) was added. The cells were stained with anti-human CD56 conjugated to fluorescein isothiocyanate (BD Biosciences) and analyzed by flow cytometry.

6.1.8 Expression of NKG2D Ligands, Phospho-Protein Analysis and Measurement of Cytokine Levels Surface expression of all NKG2D ligands was evaluated by staining with human recombinant NKG2D/Fc chimera (R&D), PE-conjugated goat anti-human IgGFc (γ) (Fisher Scientific; Hampton, N.H.), MIC A/B (6D4, BD Biosciences), ULBP-1(R&D) and ULBP-2 (R&D) and ULBP-3 (R&D).

For phosphoprotein analysis, mock- and NKG2D-DAP10-CD3zeta-transduced expanded NK cells ($8 \times 10^6$) were cultured with or without anti-NKG2D antibody and beads as described above. After 1 hour of stimulation, cell lysates were prepared using a lysis buffer containing 20 mM 3-(N-morpholino) propanesulfonic acid, 2 mM EGTA, 5 mM EDTA, 30 mM sodium fluoride, 60 mM-glycerophosphate, 20 mM sodium pyrophosphate, 1 mM sodium orthovanadate, 1% Triton X-100, Complete Mini protease inhibitor cocktail (Roche, Mannheim, Germany) and 1 mM dithiothreitol. After sonication, lysates were frozen at −80° C. and shipped in dry ice to Kinexus (Vancouver, Calif.) for Kinex Antibody Microarray analysis. To measure cytokine/chemokine production after NKG2D ligation, mock- and NKG2D-DAP10-CD3ζ cells ($1\times10^5$ in 200 μl/well of a 96-well plate) were cultured with or without anti-NKG2D antibody and beads as described above. Supernatants (120 μl) were collected after 4, 8 and 16 hours and analyzed using the Luminex human cytokine/chemokine panel I (41 human cytokines/chemokines) (Merck Millipore; Billerica, Mass.).

6.1.9 Murine Models

U2-OS cells expressing luciferase were injected i.p. in NOD.Cg-Prkdc$^{scid}$ IL2rg$^{tm1Wjl}$/SzJ (NOD/scid IL2RGnull) mice (Jackson Laboratory, Bar Harbor, Me.; $2\times10^5$ per mouse) (Cho et al., 2010, Clin Cancer Res. 16:3901-3909). NK cells from healthy donors were expanded for 7 days, transduced with the MSCV vector containing either GFP or NKG2D-DAP10-CD3zeta, resuspended in RPMI-1640 plus 10% FBS ($3\times10^6$ cells per mouse) and then injected i.p. 7 days after U2-OS injection. A single injection of NK cells was given together with i.p. injections of IL-2 (20,000 IU each) for 4 days. As a control, a group of mice received tissue culture medium instead of NK cells. U2-OS engraftment and progression was evaluated using a Xenogen IVIS-200 system (Caliper Life Sciences, Hopkinton, Mass.), with imaging beginning 5 minutes after i.p. injection of an aqueous solution of D-luciferin potassium salt (3 mg/mouse). Photons emitted from luciferase-expression cells were quantified using the Living Image 3.0 software program. The studies were approved by St. Jude Animal Care Committee.

6.2 Results 6.2.1 Chimeric Receptor Design, Construction, and Expression

The genes encoding NKG2D, DAP10 and CD3zeta were cloned from a cDNA library prepared from human NK cells, which were expanded from peripheral blood mononuclear cells. A construct encoding a chimeric receptor comprising NKG2D, DAP10 and the intracellular domain of CD3zeta was constructed and then inserted into a retroviral vector, as shown in FIG. 1A.

Human NK cells were expanded from peripheral blood mononuclear cells, and the NKG2D-DAP10-CD3zeta construct was then used to transduce expanded activated NK cells. Whether retroviral transduction of the construct resulted in an increase of NKG2D expression was tested by comparing NKG2D expression in NK cells transduced with an MSCV vector containing only GFP ("Mock') with NKG2D expression in NK cells cells transduced with the NKG2D-DAP10-CD3zeta construct. In experiments with expanded NK cells from 21 donors (>98% CD56+CD3-after T-cell depletion), median percent GFP-positive cells after transduction with the Mock GFP vector was 80% (range 67%-96%), whereas transduction with the NKG2D-DAP10-CD3zeta construct in NK cells from the same donors resulted in a marked increase in NKG2D expression (P<0.0001; Figure B).

The results of NKG2D-DAP10-CD3zeta transduction were then compared to those obtained after transduction of a NKG2D-CD3zeta construct lacking DAP10 in experiments with NK cells from 6 donors. As shown in FIG. 1C, NKG2D expression was consistently higher when DAP10 was present in the construct (P=0.0027), in agreement with previous reports indicating that DAP10 supports NKG2D expression (Wu et al., 1999, Science 285:730-732; Diefenbach et al., 2002, Nat. Immunol. 3:1142-1149; Garrity et al., 2005, Proc. Natl. Acad. Sci. USA. 102:7641-7646; Horng et al., 2007, Nat. Immunol. 8:1345-1352).

To ensure that all components of the receptor were expressed, a construct containing DAP10 with a FLAG-tag was used. As shown in FIG. 1D, NK cells transduced with NKG2D-DAP10-CD3zeta expressed DAP10. as determined by Western blot analysis using an antibody against phosphor-(pY83)-CD3zeta, these cells were demonstrated to express a chimeric protein containing CD3ζ in addition to endogenous CD3zeta (FIG. 1E). Thus, the three components of the NKG2D-DAP10-CD3zeta receptor were demonstrated to be expressed in human NK cells.

Figure 2C:
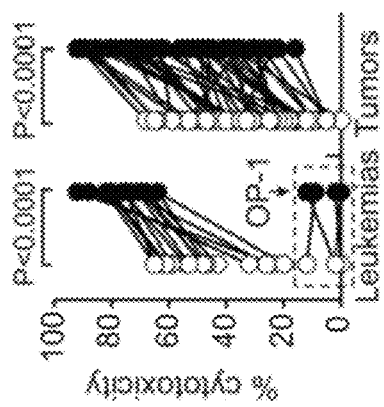

6.2.2 NKG2D-DAP10-CD3zeta Receptors Increase the Anti-Tumor Cytotoxicity of Activated NK Cells NK cells expanded and activated after co-culture with the K562-mb15-41BBL cell line exert much higher cytotoxicity than that of either primary NK cells or IL-2-stimulated NK cells (Cho et al., 2010, Clin Cancer Res. 16:3901-3909; Fujisaki et al., 2009, Cancer Res. 69:4010-4017). Whether expression of NKG2D-DAP10-CD3zeta receptors in these cells could further improve their anti-tumor cytotoxicity was investigated. For this purpose, a broad panel of tumor cell lines originating from T-cell ALL (CEM-C7, MOLT-4, Jurkat) and B-cell ALL (REH, OP-1), osteosarcoma (U-2 OS, MG-36, HOS), prostate carcinoma (DU 145, PC-3, LNCaP), rhabdomyosarcoma (RH18, RH30, TE32, RH36), neuroblastoma (SKNSH), Ewing sarcoma (TC71), colon carcinoma (Km12L4), gastric carcinoma (SNU1), lung squamous cell carcinoma (SW900), hepatoma (HepG2), and breast carcinoma (MCF7) were targeted. Four-hour cytotoxicity assays with NK cells expanded from 14 donors at 1:1 or 1:2 effector:target (E:T) ratios for a total of 65 experiments were performed. First, the E:T ratio that would produce submaximal levels of cytotoxicity was determined or each cell line. Then, the gains produced by transducing NK cells with NKG2D-DAP10-CD3zeta were tested. Cells from the same donors transduced with a vector containing GFP alone were used as a control. As shown in FIGS. 2A and B, expression of the NKG2D-DAP10-CD3zeta receptor significantly increased overall cytotoxicity against both leukemic and solid tumor cell lines (P<0.0001). Gains in cytotoxicity were particularly evident in the ALL cell lines REH, MOLT4 and CEM-C7, in the osteosarcoma cell lines U-2 OS, MG-36, HOS, in the prostate carcinoma cell lines DU 145 and PC-3, and in the rhabdomyosarcoma cell line RH36 (FIG. 2C). The sole exception was the B-lineage ALL cell line OP-1, which remained relatively refractory to NK cells despite NKG2D-DAP10-CD3zeta receptor expression (FIG. 2A).

Figure 2D:
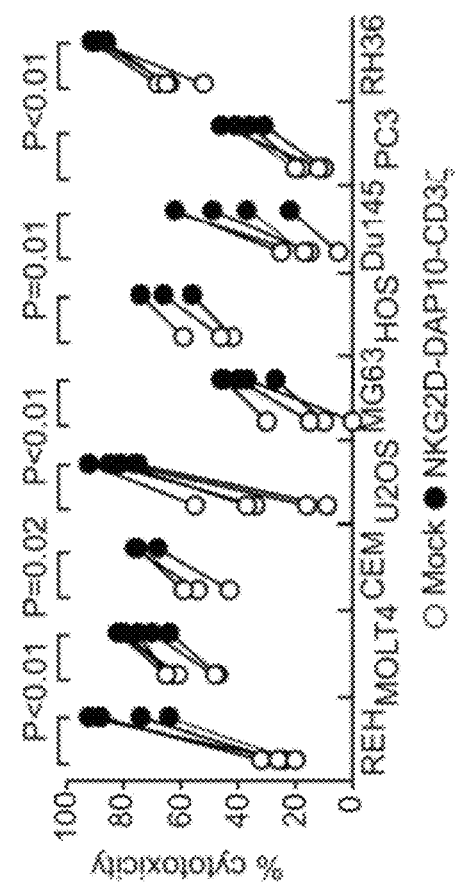

Whether expression of NKG2D-DAP10-CD3zeta receptors increased the cytotoxicity of expanded NK cells against non-transformed cells, such as allogeneic peripheral blood mononuclear cells and bone marrow-derived mesenchymal cells, was then investigated. As shown in FIG. 2D, cytotoxicity remained below 20% at 1:1 ratio, regardless of whether NK cells were transduced with the receptor or with GFP (FIG. 2D). These results indicate that expression of NKG2D-DAP10-CD3ζ☐receptors can markedly enhance NK cell cytotoxicity against cancer cells without significantly increasing their activity against non-tumor cells.

6.2.3 NK Cytotoxicity is Triggered by Ligation of NKG2D-DAP10-CD3zeta Receptors

Figure 3A:
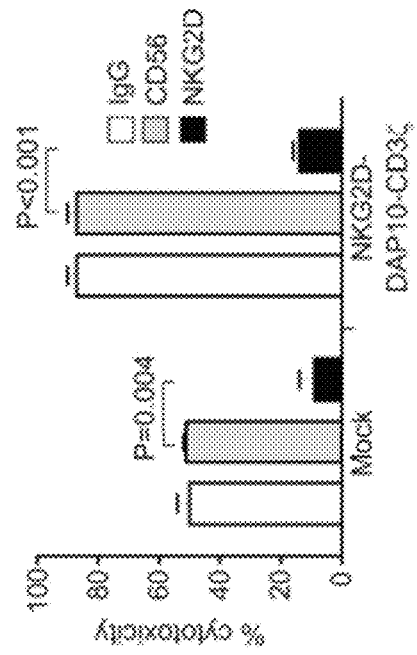

The relation between NKG2D-DAP10-CD3zeta mediated cytotoxicity and expression of NKG2D ligands on target cells was then analyzed. To this end, a human recombinant NKG2D/Ig Fc reagent was used to measure the collective expression of all NKG2D ligands. The cell line OP-1 did not show any labeling with NKG2D/Ig Fc, and also gave a negative staining with antibodies to MICA/B, ULBP-1, -2 and -3, which explained its resistance to NK cell killing regardless of whether these expressed NKG2D-DAP10-CD3zeta or not. All the remaining cell lines studied were labeled by NKG2D/Ig Fc, but no significant relation between level of overall NKG2D ligand expression and NKG2D-DAP10-CD3zeta receptor-mediated cytotoxicity was observed (FIG. 3A). Non-transformed bone marrow-derived mesenchymal cells and peripheral blood monocytes had a relatively weak staining with NKG2D/Ig Fc, and most peripheral blood lymphocytes had no staining at all.

Figure 3B:
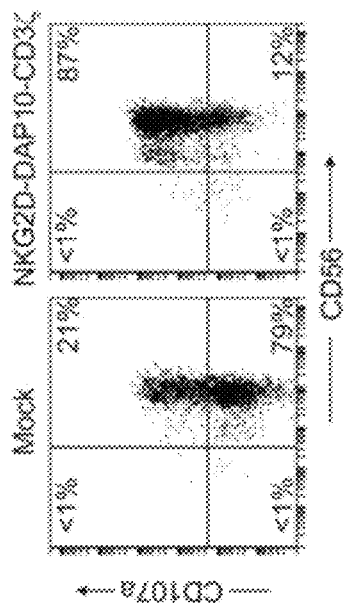
Figure 3C:
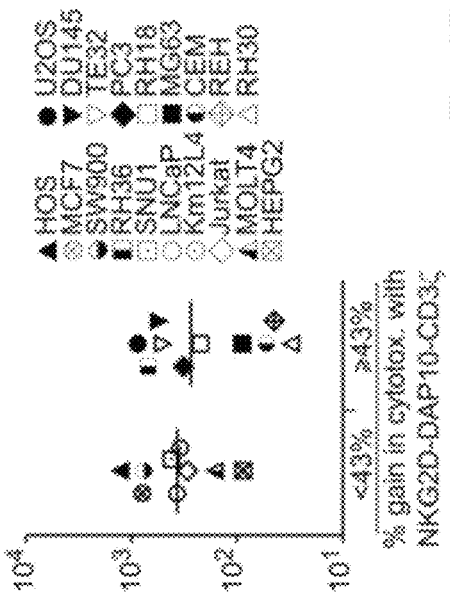
Figure 3D:
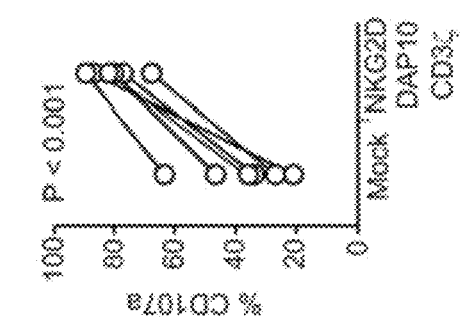

To ascertain whether the increase in cytotoxicity produced by transduction of the NKG2D-DAP10-CD3zeta receptor was directly related to receptor stimulation, an anti-NKG2D blocking antibody (clone 149810; Cho et al., 2010, Clin Cancer Res. 16:3901-3909) was used. In experiments with the U-2 OS osteosarcoma cell line, preincubation of NK cells with the antibody markedly inhibited NK cytotoxicity and abrogated the gains achieved by NKG2D-DAP10-CD3zeta receptor transduction (FIG. 3B). Conversely, direct stimulation of the receptor by an anti-NKG2D agonistic antibody (clone 1D11; Barber et al., 2011, Blood 117:6571-6581) provoked massive lysosomal granule exocytosis, as detected by CD107a expression (Betts et al., 2003, J. Immunol. Methods. 281:65-78), which was significantly higher than that achieved by NKG2D stimulation of mock-transduced NK cells ($P<0.001$; FIG. 3C, D).

6.2.4 Engagement of NKG2D-DAP10-CD3zeta Triggers Signal Transduction, Cytokine Secretion and Sustained Stimulation To further understand the signaling properties of NKG2D-DAP10-CD3zeta and the differences from the signals triggered by endogenous NKG2D, mock- and NKG2D-DAP10-CD3zeta-transduced activated NK cells were stimulated with the anti-NKG2D agonistic antibody for 1 hour, and cell lysates were analyzed with the Kinex antibody microarray, which contains 809 anti-phosphoprotein antibodies. As shown in FIG. 4A, the phosphoprotein profile of NKG2D-DAP10-CD3zeta-expressing NK cells was substantially different from that of mock-transduced NK cells. Particularly prominent after NKG2D-DAP10-CD3zeta stimulation was the phosphorylation of the CREB1 transcription factor, known to promote activation and proliferation of T and B cells (Wen et al., 2010, J. Immunol. 185:6413-6419), of TBK1, a serine-threonine protein kinase and NF-κB activator with pro-survival roles (Baldwin et al., 2012, Immunol. Rev. 246:327-345), and of ACK1, a tyrosine-protein and serine/threonine-protein kinase that regulates AKT (Mahajan et al., 2010, J. Cell Physiol. 224:327-333), a key effector of DAP10 signaling (Chang et al., 1999, J. Immunol. 163:4651-4654).

To determine whether NKG2D-DAP10-CD3zeta signaling resulted in an increased cytokine/chemokine secretion, mock or transduced NK cells from 3 donors were incubated with the biotin-labeled anti-NKG2D agonistic antibody and anti-biotin beads and measured cytokine/chemokine levels in the supernatants after 4, 8 and 16 hours. As shown in FIG. 4B and Supplementary FIG. 1, engagement of NKG2D-DAP10-CD3zeta caused a marked increase in IFNγ, GM-CSF, IL-13, MIP-1α, MIP-1β, CCL5 and TNFα production ($P<0.01$ by 2-way ANOVA for all comparisons). For these 7 factors, levels were also significantly higher when NKG2D-stimulated cells (either mock- or NKG2D-DAP10-CD3zeta-transduced) were compared to the same cells cultured without antibody (Table 1). Levels of the other cytokines/chemokines measured (IL-1α, IL-1β, IL-1rα, IL-3, IL-4, IL-5, IL-6, IL-7, IL-8, IL-9, IL-10, IL-12 (p40), IL-12 (p70), IL-15, IL-17A, sCD40L, EGF, eotaxin, FGF-2, Flt-3 ligand, fractalkine, G-CSF, GRO, IFNα2, IP-10, MCP-1, MCP-3, MDC, PDGF-AA, PDGF-BB, TGFα, TNFβ, and VEGF) were not significantly different between mock- and NKG2D-DAP10-CD3ζ-transduced NK cells, regardless of NKG2D stimulation (see Table 1). For EGF, G-CSF, IL-10, IL-12p40, IL-12p70, IL-15, IL-17, IL-1α, IL-1β, IL-3, IL-4, IL-6, IL-7, IL-9, IP-10, MCP-3, MDC, PDGF-BB and TGF-α, all the measurements were <5 pg/mL.

TABLE 1

Cytokine/chemokine secretion (mean ± SD pg/mL) after stimulation of mock- or NKG2D-DAP10-CD3zeta-transduced NK cells with anti-NKG2D[a]

| Cytokine/Chemokine | No stimulation | | Stimulation | |
| --- | --- | --- | --- | --- |
| | Mock | NKG2D-DAP10-CD3zeta | Mock | NKG2D-DAP10-CD3zeta |
| GM-CSF | 20 ± 17 | 18 ± 16 | 71 ± 50 | 750 ± 310 |
| IFN-γ | 9 ± 8 | 12 ± 8 | 81 ± 62 | 717 ± 466 |
| IL-2 | 606 ± 15[b] | 580 ± 27[b] | 521 ± 48[b] | 375 ± 75[b] |
| IL-13 | <5 | <5 | 49 ± 42 | 198 ± 121 |
| MIP-1α | 126 ± 88 | 233 ± 147 | 482 ± 349 | 4952 ± 2151 |
| MIP-1β | 178 ± 67 | 346 ± 88 | 956 ± 198 | 9931 ± 827 |
| Rantes | 310 ± 47 | 500 ± 37 | 1267 ± 188 | 5354 ± 541 |
| TNF-α | 13 ± 11 | 12 ± 10 | 110 ± 80 | 974 ± 559 |
| Eotaxin | <5 | <5 | <5 | 7 ± 7 |
| FGF-2 | 12 ± 4 | 14 ± 10 | 15 ± 7 | 32 ± 29 |
| Flt-3L | <5 | 9 ± 1 | 10 ± 3 | 24 ± 22 |
| Fractalkine | 24 ± 17 | 9 ± 16 | 43 ± 7 | 55 ± 37 |
| GRO | 5 ± 9 | <5 | <5 | <5 |
| IFN-α2 | <5 | <5 | <5 | 10 ± 15 |
| IL-1rα | <5 | <5 | 8 ± 7 | <5 |
| IL-5 | <5 | <5 | <5 | 5 ± 4 |
| IL-8 | <5 | <5 | <5 | 10 ± 8 |
| MCP-1 | <5 | <5 | <5 | 7 ± 5 |
| PDGF-AA | <5 | <5 | <5 | 6 ± 2 |
| TNF-β | <5 | <5 | <5 | 15 ± 9 |
| VEGF | 12 ± 11 | 20 ± 18 | 12 ± 11 | 9 ± 16 |
| sCD40L | 10 ± 3 | 14 ± 13 | 17 ± 4 | 34 ± 34 |

[a]NK cells expanded from 3 donors, either transduced with NKG2D-DAP10-CD3zeta or mock-transduced, were incubated with anti-Biotin MACSiBeads (Miltenyi Biotec, Auburn, CA) coated with biotin-anti NKG2D (clone 1D11; eBioscience; San Diego, CA) antibody (ten beads for one NK cell). Supernatants were collected after 16 hours at 37° C. and analyzed using the Luminex human cytokine/chemokine panel I (41 human cytokines/chemokines) (Merck Millipore; Billerica, MA). Supernatants collected from cells cultured without anti-NKG2D beads were also studied.
[b]Exogenous IL-2 (50 IU/ml) was present in the tissue culture medium.

To further explore the mechanisms underlying the enhancement of cytotoxicity triggered by the NKG2D-DAP10-CD3zeta receptors, immunofluorescence imaging studies were performed using the U-2 OS cell line as a target. In experiments with NK cells from 3 donors, those expressing the NKG2D-DAP10-CD3zeta receptors produced clear increases in target cell apoptosis when compared to mock-transfected cells (11.7±2.9 versus 3.3±0.6 apoptotic cells/0.07 mm$^2$; P=0.033). These gains could not be attributed to an increase in cell speed movement or cell track displacement length, which were similar for receptor- and mock-transduced NK cells: 0.027±0.01 versus 0.027±0.01 μm/sec, and 18.1±10.1 versus 17.5±6.7 μm, respectively.

Continuous stimulation via NKG2D ligation may result in a hyporesponsive status (Vivier et al., 2011, Science 331: 44-49). To test the anergy-inducing potential of NKG2D-DAP10-CD3zeta signaling as compared to that of endogenous NKG2D, mock- and NKG2D-DAP10-CD3zeta-transduced NK cells with the anti-NKG2D agonistic antibody were cultured, and exocytosis of lytic granules with CD107a staining over 48 hours was monitored. Mock-transduced NK cells were unable to degranulate after 24 or 48 hours of stimulation. By contrast, a substantial proportion of NKG2D-DAP10-CD3zeta-transduced NK cells were CD107a-positive 24 and 48 hours after continuous NKG2D ligation (FIG. 4C). Hence, NK cells bearing the receptor are capable of exerting cytotoxicity even after prolonged engagement of NKG2D.

6.2.5 Cytotoxicity of NK Cells Expressing NKG2D-DAP10-CD3zeta in Xenografts

To test the anti-tumor capacity of NK cells expressing NKG2D-DAP10-CD3zeta in vivo, a xenograft model of osteosarcoma was generated by injecting luciferase-labeled U-2 OS cells ($2 \times 10^5$) intraperitoneally (i.p.) in 12 immunodeficient (NOD/scid-IL2Rgnull) mice (FIG. 5). In 4 mice without treatment, U-2 OS cells progressively expanded. Another four mice were injected with $2 \times 10^5$ U-2 OS i.p. and then a single i.p. injection of mock-transduced NK cells ($3 \times 10^6$) 7 days later, followed by four daily IL-2 i.p. injections; U-2 OS cells in this group also expanded. A third group of four mice was injected with an identical number of U-20S i.p. and a single i.p injection of NK cells transduced with the NKG2D-DAP10-CD3zeta construct ($3 \times 10^6$) followed by four daily IL-2 i.p. injections. Seven days after the NK cells were injected, the average signal intensity decreased dramatically and overall tumor burden remained significantly lower to that measured in mice treated with mock-transduced NK cells (P=0.0028 by 2-way ANOVA; FIG. 5).

6.2.6 Expression of NKG2D-DAP10-CD3zeta by Electroporation

Although effective, gene expression by retroviral transduction presents considerable practical constraints for large-scale clinical application. It was previously observed that electroporation of mRNA results in highly efficient expression of functional receptors in NK cells, and that this method can be adapted to a clinical-grade protocol for genetic engineering of large cell numbers (Shimasaki et al., 2012, Cytotherapy 14:830-840). To determine whether the NKG2D-DAP10-CD3zeta receptor could be expressed by this method, mRNA encoding NKG2D-CD3zeta and DAP10 was produced, electroporated into expanded NK cells, and NKG2D expression was determined 24 hours later. As shown in FIG. 6A, electroporation resulted in high NKG2D expression. NK cells electroporated with the receptor were markedly more cytotoxic against the U2-OS cell line than mock-electroporated NK cells (FIG. 6B).

6.3 Discussion

The NKG2D activating receptor is central to capacity of NK cells to sense cellular stress and lyse virally-infected and tumor cells (Vivier et al., 2011, Science 331:44-49; Champsaur et al., 2010, Immunol. Rev. 235:267-285; Smyth et al., 2005, J Exp. Med. 202:583-588, Routes et al., 2005, J Exp. Med. 202:1477-82; Karimi et al., 2005, J. Immunol. 175: 7819-7828; Guerra et al., 2008, Immunity 28:571-580; Cho et al., 2010, Clin. Cancer Res. 16:3901-3909; Raulet, 2003, Nat. Rev. Immunol. 3:781-790; Bryceson et al., 2008, Eur. J. Immunol. 38:2957-2961). This study demonstrated that expression of an activating receptor with the binding specificity of NKG2D and the combined signaling capacities of DAP10 and CD3zeta considerably enhances the cytotoxicity of activated NK cells against leukemias and solid tumors. The increase in NK-mediated anti-tumor activity were also evident in experiments with immunodeficient mice engrafted with osteosarcoma cells, where NK cells expressing NKG2D-DAP10-CD3zeta receptors produced marked tumor reductions while mock-transduced activated NK cells were ineffective. The cytotoxicity of NK cells expressing NKG2D-DAP10-CD3zeta receptors was directly triggered by engagement of NKG2D. In contrast, receptor expression did not significantly increase cytotoxicity against non-transformed cells with low or no NKG2D ligand expression, or against leukemic cells lacking NKG2D-ligands. While most of the experiments presented above relied on retroviral transfection of the receptor, a method to efficiently express the receptor by electroporation was developed, thus greatly facilitating its clinical application for cell therapy of cancer (Shimasaki et al., 2012, Cytotherapy 14:830-840).

The configuration of the NKG2D-DAP10-CD3zeta receptor, which allows for signal transduction by both DAP10 and CD3zeta, differs from the typical chimeric-antigen receptors ("CARs"), which contain either one signaling molecule, or a stimulatory plus a co-stimulatory molecule in tandem (Kohn et al., 2011, Molecular Therapy: The Journal of the American Society of Gene Therapy, 19:432-438). In keeping with previous reports indicating that DAP10 promotes NKG2D expression on the surface membrane (Wu et al., 1999, Science 285:730-732; Diefenbach et al., 2002, Nat. Immunol. 3:1142-1149; Garrity et al., 2005, Proc. Natl. Acad. Sci. USA. 102:7641-7646; Horng et al., 2007, Nat. Immunol. 8:1345-1352), expression of the NKG2D-CD3ζ construct was found to be significantly improved by concomitant expression of DAP10, regardless of whether expression was enforced by retroviral transduction or electroporation. It has been reported that a receptor coupling NKG2D and CD3ζ could be expressed in T lymphocytes and enhanced their cytotoxicity against lymphoma (Zhang et al., 2007, Cancer Res. 67:11029-11036), myeloma (Barber et al., 2008, Exp. Hematol., 36:1318-1328), ovarian cancer (Barber et al., 2009, J. Immunol. 183:6939-6947) and Ewing's sarcoma cells (Lehner et al., 2012, PloS. One 7:e31210).

NKG2D-DAP10-CD3ζ-receptor signaling augmented the cytotoxicity of activated NK cells against a wide spectrum of tumor cell targets. It has also been shown that the pattern of NKG2D ligand partitioning in the target cell membrane, and the degree of ligand shedding can play a role in triggering cytotoxicity (Martinez et al., 2011, J. Immunol. 186:5538-5542; Salih et al., 2002, J. Immunol. 169:4098-4102; Aguera-Gonzalez et al., 2011, Eur. J. Immunol. 41:3667-3676). Gains in cytotoxicity brought about by NKG2D-DAP10-CD3zeta receptor expression were dependent on its signaling, as an antagonist anti-NKG2D antibody abrogated them. The magnitude of the observed increase (more than twice as many cells killed within 4 hours in some cases) is particularly noteworthy considering that the NK cells included in these studies were activated and can exert cytotoxicities which are already significantly higher than those of primary and IL-2 activated NK cells (Fujisaki et al., 2009, Cancer Res. 69: 4010-4017). Thus, the cytotoxicity potential of activated NK cells is not maximal and can be further enhanced by boosting activating signals.

Persistent stimulation of NK cells may result in suppression of NK cell function (Coudert et al., 2005, Blood 106:1711-1717; Oppenheim et al., 2005, Nat. Immunol. 6:928-937). Indeed, mock-transduced NK cells were unable to degranulate after 24 hours of continuous stimulation. However, a considerable proportion of the same NK cells expressing NKG2D-DAP10-CD3ζ receptors were CD107a positive even after 48 hours of stimulation, indicating that the combined DAP10 and CD3 zeta signals do not accelerate the occurrence of hyporesponsiveness; on the contrary, they significantly prolong NK cell function. The NKG2D receptor has been shown to contribute to autoimmunity, but pathological responses against normal tissues could be attributed to the fraction of CD8 T lymphocytes expressing this receptor and not to NK cells (Markiewicz et al., 2012, Immunity 36:132-141). These studies showed that expression of the NKG2D-DAP10-CD3zeta receptor did not significantly increase cytotoxicity against non-transformed peripheral blood lymphocytes or bone marrow-derived mesenchymal cells. For clinical application, this potential problem should be prevented by careful depletion of T cells from the NK cell product together with transient expression of the receptor by electroporation.

It is well established that donor NK cell alloreactivity suppresses leukemia relapse after allogeneic hematopoietic stem cell transplantation (Ruggeri et al., 2002, Science 295:2097-2100; Cooley et al., 2010, Blood 116:2411-2419). Infusion of NK cells in a non-transplant setting has shown promise in some studies (Miller et al., 2005, Blood 105:3051-3057; Rubnitz et al., 2010, J Clin Oncol. 28:955-959), and hence this approach is being active pursued at several centers using either freshly purified or activated NK cells.

The method described herein offers a novel method for increasing the anti-tumor efficacy of NK cell therapy and widen its application. Stimulation via the NKG2D-DAP10-CD3zeta receptor also resulted in a marked increase in cytokine/chemokine secretion. Thus, NK-derived GM-CSF, IFNγ and TNFα promote monocyte differentiation, macrophage activation and dendritic cell maturation (Vivier et al., 2011, Science 331:44-49; Goldszmid et al, 2012, Immunity 36:1047-1059; Spear et al., 2012, J. Immunol. 188:6389-6398). These cellular effects should be important during immune-responses against pathogens, suggesting that infusion of NKG2D-DAP10-CD3zeta-NK cells should also be useful as therapeutics against infectious diseases.

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

What is claimed is:

1. A method of treating a cancer using immunotherapy, the method comprising:
   administering to a subject having the cancer a population of engineered, primary Natural Killer (NK) cells comprising a chimeric receptor, wherein:
   the chimeric receptor is a cell-surface receptor,
   the cell-surface receptor comprises at least two polypeptide domains not naturally found together on a single protein,
   the cell-surface receptor consists essentially of:
   an NKG2D receptor extracellular ligand binding domain, wherein the NKG2D receptor extracellular ligand binding domain has at least 98% sequence identity to amino acids 103 to 216 of a native human NKG2D receptor,
   a cytoplasmic signaling domain that is at least 90% identical to the amino acid sequence of SEQ ID NO: 10, and
   a transmembrane domain that operably couples the NKG2D receptor extracellular ligand binding domain to the cytoplasmic signaling domain.

2. The method of claim 1, wherein the proliferation of cancer cells contacted with the population of NK cells is inhibited or reduced by at least 25% as compared to cancer cells contacted with a native NK cell population.

3. The method of claim 1, wherein the cytoplasmic signaling domain is at least 98% identical to the amino acid sequence of SEQ ID NO: 10, wherein the population of NK cells exhibit a cytotoxic effect against cells of a tumor, and wherein the population of NK cells exhibit a cytotoxic effect of less than 20% against non-tumor cells.

4. The method of claim 1, wherein the cancer is a cancer of B-cell origin.

5. The method of claim 4, wherein the cancer is selected from the group consisting of B-lineage acute lymphoblastic leukemia, B-cell chronic lymphocytic leukemia and B-cell non-Hodgkin's lymphoma.

6. The method of claim 1, wherein the cancer is selected from the group consisting of lung cancer, melanoma, breast cancer, prostate cancer, colon cancer, renal cell carcinoma, ovarian cancer, neuroblastoma, rhabdomyosarcoma, leukemia and lymphoma, acute lymphoblastic leukemia, small cell lung cancer, Hodgkin's lymphoma, or childhood acute lymphoblastic leukemia.

7. The method of claim 1, wherein upon administration the population of NK cells enhances one or more immune functions or responses by at least 30% as compared to a native NK cell population.

8. The method of claim 7, wherein the immune functions or responses comprises:
   cytokine release, wherein the cytokine is one or more of interferon-gamma, IL-2, IL-5, IL-10, IL-12, or TGF-beta;
   NK cell proliferation;
   T cell proliferation;
   antibody production; or
   effector function, wherein the effector function comprises cytotoxicity.

9. The method of claim 1, wherein the population of NK cells administered comprises at least about 1×10⁶ NK cells.

10. The method of claim 1, wherein the population of NK cells is autologous to a subject being treated.

11. The method of claim 1, wherein the population of NK cells is allogeneic to a subject being treated.

12. The method of claim 1, wherein the NKG2D extracellular ligand binding domain is capable of binding to one or more one or more native ligands, wherein the one or more one or more native ligands are MICA, MICB, ULBP1, ULBP2, ULBP3, ULBP4, ULBP5, or ULBP6.

13. The method of claim 1, wherein the NKG2D extracellular ligand binding domain has a sequence according to amino acids 102-215 of SEQ ID NO: 12.

14. A method of treating a cancer using immunotherapy, the method comprising:
   administering to a subject having the cancer a population of engineered, primary Natural Killer (NK) cells comprising a chimeric receptor, wherein:
   the chimeric receptor is a cell-surface receptor,
   the cell-surface receptor comprises at least two polypeptide domains not naturally found together on a single protein,
   the cell-surface receptor consists essentially of:
   an NKG2D receptor extracellular ligand binding domain, wherein the NKG2D receptor extracellular ligand binding domain has at least 98% sequence identity to amino acids 103 to 216 of a native human NKG2D receptor,
   a cytoplasmic signaling domain that is at least 90% identical to the amino acid sequence of SEQ ID NO: 10, and
   a transmembrane domain that operably couples the NKG2D receptor extracellular ligand binding domain to the cytoplasmic signaling domain, and
   wherein upon administration to the subject, the population of NK cells enhances one or more immune functions or responses by at least 30% as compared to a native NK cell population.

15. The method of claim 14, wherein the proliferation of cancer cells contacted with the population of NK cells is inhibited or reduced by at least 25% as compared to cancer cells contacted with a native NK cell population.

16. The method of claim 14, wherein the cytoplasmic signaling domain is at least 98% identical to the amino acid sequence of SEQ ID NO: 10, wherein the population of NK cells exhibit a cytotoxic effect against cells of a tumor, and wherein the population of NK cells exhibit a cytotoxic effect of less than 20% against non-tumor cells.

17. The method of claim 14, wherein the cancer is a cancer of B-cell origin.

18. The method of claim 17, wherein the cancer is selected from the group consisting of B-lineage acute lymphoblastic leukemia, B-cell chronic lymphocytic leukemia and B-cell non-Hodgkin's lymphoma.

19. The method of claim 14, wherein the cancer is selected from the group consisting of lung cancer, melanoma, breast cancer, prostate cancer, colon cancer, renal cell carcinoma, ovarian cancer, neuroblastoma, rhabdomyosarcoma, leukemia and lymphoma, acute lymphoblastic leukemia, small cell lung cancer, Hodgkin's lymphoma, or childhood acute lymphoblastic leukemia.

20. The method of claim 14, wherein the population of NK cells administered comprises at least about 1×10⁶ NK cells.

21. The method of claim 14, wherein the population of NK cells is autologous to a subject being treated.

22. The method of claim 14, wherein the population of NK cells is allogeneic to a subject being treated.

23. The method of claim 14, wherein the NKG2D extracellular ligand binding domain is capable of binding to one or more one or more native ligands, wherein the one or more one or more native ligands are MICA, MICB, ULBP1, ULBP2, ULBP3, ULBP4, ULBP5, or ULBP6.

24. The method of claim 14, wherein the NKG2D extracellular ligand binding domain has a sequence according to amino acids 102-215 of SEQ ID NO: 12.

\* \* \* \* \*

EX PARTE REEXAMINATION CERTIFICATE (12241st)

United States Patent
Campana et al.

(10) Number: US 10,829,737 C1
(45) Certificate Issued: *Mar. 13, 2023

(54) CHIMERIC RECEPTOR WITH NKG2D SPECIFICITY FOR USE IN CELL THERAPY AGAINST CANCER AND INFECTIOUS DISEASE

(71) Applicants: ST. JUDE CHILDREN'S RESEARCH HOSPITAL, INC., Memphis, TN (US); NATIONAL UNIVERSITY OF SINGAPORE, Singapore (SG)

(72) Inventors: Dario Campana, Singapore (SG); Yu-Hsiang Chang, Kaohsiung (TW)

(73) Assignees: ST. JUDE CHILDREN'S RESEARCH HOSPITAL, INC., Memphis, TN (US); NATIONAL UNIVERSITY OF SINGAPORE, Singapore (SG)

Reexamination Request:
No. 90/014,883, Oct. 15, 2021

Reexamination Certificate for:
Patent No.: 10,829,737
Issued: Nov. 10, 2020
Appl. No.: 15/857,268
Filed: Dec. 28, 2017

(*) Notice: This patent is subject to a terminal disclaimer.

Related U.S. Application Data

(63) Continuation of application No. 15/337,854, filed on Oct. 28, 2016, now Pat. No. 10,538,739, which is a continuation of application No. 14/764,070, filed as application No. PCT/US2014/013292 on Jan. 28, 2014, now Pat. No. 9,511,092.

(60) Provisional application No. 61/757,481, filed on Jan. 28, 2013.

(51) Int. Cl.
| | |
|---|---|
| C12N 5/0783 | (2010.01) |
| A61K 35/17 | (2015.01) |
| A61K 38/00 | (2006.01) |
| C07K 14/705 | (2006.01) |
| C07K 14/725 | (2006.01) |
| C12N 5/00 | (2006.01) |

(52) U.S. Cl.
CPC ............ *C12N 5/0646* (2013.01); *A61K 35/17* (2013.01); *A61K 38/00* (2013.01); *C07K 14/705* (2013.01); *C07K 14/7051* (2013.01); *C07K 14/7056* (2013.01); *C12N 5/0087* (2013.01); *C07K 2319/00* (2013.01); *C07K 2319/70* (2013.01); *C12N 2510/00* (2013.01)

(58) Field of Classification Search
None
See application file for complete search history.

(56) References Cited

To view the complete listing of prior art documents cited during the proceeding for Reexamination Control Number 90/014,883, please refer to the USPTO's Patent Electronic System.

*Primary Examiner* — Padmashri Ponnaluri

(57) ABSTRACT

The invention provides a chimeric receptor comprising NKG2D, DAP10 and CD3 zeta. Also disclosed is a composition comprising this chimeric receptor and methods for making and using it to enhance the cytotoxicity and antitumor capacity of NK cells. The invention also encompasses methods for use of NKG2D-DAP10-CD3 zeta polypeptides, vectors and cells in methods for treating cancer and other proliferative disorders, as well as infectious diseases.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3, 7, 8, 10-16 and 21-24 are determined to be patentable as amended.

Claims 4-6, 9 and 17-20, dependent on an amended claim, are determined to be patentable.

1. A method of treating a cancer using immunotherapy, the method comprising,
    administering to a subject having the cancer a population of *activated, expanded, and* engineered[,] primary Natural Killer (NK) cells comprising a chimeric receptor, wherein:
    the chimeric receptor is a cell-surface receptor,
    the cell-surface receptor comprises at least two polypeptide domains not naturally found together on a single protein,
    the cell-surface receptor consists essentially of:
        [an NKG2D] (*a*) *a Natural Killer Group 2 member D (NKG2D)* receptor extracellular ligand binding domain, wherein the NKG2D receptor extracellular ligand binding domain has at least 98% sequence identity to amino acids 103 to 216 of a native human NKG2D receptor,
        (*b*) a cytoplasmic signaling domain that is at least 90% identical to the amino acid sequence of SEQ ID NO: 10, and
        (*c*) a [transmembrane domain] *DNAX-activating protein 10 (DAP10)* that operably couples the NKG2D receptor extracellular ligand binding domain to the cytoplasmic signaling domain.

2. The method of claim 1, wherein the proliferation of cancer cells contacted with the population of NK cells is inhibited or reduced by at least 25% as compared to cancer cells contacted with [a ] *an activated and expanded* native NK cell population.

7. The method of claim 1, wherein upon administration the population of NK cells enhances one or more immune functions or responses by at least 30% as compared to [a] *an activated and expanded* native NK cell population.

8. The method of claim 7, wherein the *one or more* immune functions or responses [comprises] *comprise*:
    cytokine release, wherein the cytokine is one or more of interferon-gamma, IL-2, IL-5, IL-10, IL-12, or TGF-beta;
    NK cell proliferation;
    T cell proliferation;
    antibody production; or
    effector function, wherein the effector function comprises cytotoxicity.

10. The method of claim 1, wherein the population of NK cells is autologous to [a] *the* subject being treated.

11. The method of claim 1, wherein the population of NK cells is allogeneic to [a] *the* subject being treated.

12. The method of claim 1, wherein the NKG2D *receptor* extracellular ligand binding domain is capable of binding to one or more [one or more] native ligands, wherein the one or more [one or more] native ligands are MICA, MICB, ULBP1, ULBP2, ULBP3, ULBP4, ULBP5, or ULBP6.

13. The method of claim 1, wherein the NKG2D *receptor* extracellular ligand binding domain has a sequence according to amino acids 102-215 of SEQ ID NO: 12.

14. A method of treating a cancer using immunotherapy, the method comprising:
    administering to a subject having the cancer a population of *activated, expanded, and* engineered[,] primary Natural Killer (NK) cells comprising a chimeric receptor, wherein:
    the chimeric receptor is a cell-surface receptor,
    the cell-surface receptor comprises at least two polypeptide domains not naturally found together on a single protein,
    the cell-surface receptor consists essentially of:
        [an NKG2D] (*a*) *a Natural Killer Group 2 member D (NKG2D)* receptor extracellular ligand binding domain, wherein the NKG2D receptor extracellular ligand binding domain has at least 98% sequence identity to amino acids 103 to 216 of a native human NKG2D receptor,
        (*b*) a cytoplasmic signaling domain that is at least 90% identical to the amino acid sequence of SEQ ID NO: 10, and
        (*c*) a [transmembrane domain] *DNAX-activating protein 10 (DAP10)* that operably couples the NKG2D receptor extracellular ligand binding domain to the cytoplasmic signaling domain, and
    wherein upon administration to the subject, the population of NK cells enhances one or more immune functions or responses by at least 30% as compared to [a] *an activated and expanded* native NK cell population.

15. The method of claim 14, wherein the proliferation of cancer cells contacted with the population of NK cells is inhibited or reduced by at least 25% as compared to cancer cells contacted with [a] *an activated and expanded* native NK cell population.

21. The method of claim 14, wherein the population of NK cells is autologous to [a] *the* subject being treated.

22. The method of claim 14, wherein the population of NK cells is allogeneic to [a] *the* subject being treated.

23. The method of claim 14, wherein the NKG2D *receptor* extracellular ligand binding domain is capable of binding to one or more [one or more] native ligands, wherein the one or more [one or more] native ligands are MICA, MICB, ULBP1, ULBP2, ULBP3, ULBP4, ULBP5, or ULBP6.

24. The method of claim 14, wherein the NKG2D *receptor* extracellular ligand binding domain has a sequence according to amino acids 102-215 of SEQ ID NO: 12.

* * * * *